US009492518B2

(12) United States Patent
Dranoff et al.

(10) Patent No.: US 9,492,518 B2
(45) Date of Patent: Nov. 15, 2016

(54) TUMOR IMMUNITY

(75) Inventors: Glenn Dranoff, Lexington, MA (US);
Masahisa Jinushi, Tokyo (JP)

(73) Assignee: Dana-Farber Cancer Institute, Inc.,
Boston, MA (US)

( * ) Notice: Subject to any disclaimer, the term of this patent is extended or adjusted under 35 U.S.C. 154(b) by 1363 days.

(21) Appl. No.: 12/444,047

(22) PCT Filed: Oct. 4, 2007

(86) PCT No.: PCT/US2007/080446
§ 371 (c)(1),
(2), (4) Date: Mar. 4, 2010

(87) PCT Pub. No.: WO2008/043018
PCT Pub. Date: Apr. 10, 2008

(65) Prior Publication Data
US 2010/0189711 A1    Jul. 29, 2010

Related U.S. Application Data

(60) Provisional application No. 60/828,177, filed on Oct. 4, 2006.

(51) Int. Cl.
*A61K 39/395* (2006.01)
*A61K 38/17* (2006.01)
*A61K 39/00* (2006.01)
*C07K 16/28* (2006.01)

(52) U.S. Cl.
CPC .... *A61K 39/0011* (2013.01); *A61K 2039/5152* (2013.01); *A61K 2039/5156* (2013.01); *A61K 2039/55516* (2013.01); *A61K 2039/55522* (2013.01)

(58) Field of Classification Search
CPC ............. A61K 39/0011; A61K 39/30; A61K 2039/51; A61K 2039/5152; A61K 2039/505; A61K 2039/572; A61K 38/177
USPC ......... 424/130.1, 141.1, 145.1, 152.1, 156.1, 424/184.1, 192.1, 193.1, 277.1, 278.1, 93.1, 424/93.2, 93.7, 185.1; 514/395, 402, 403
See application file for complete search history.

(56) References Cited

U.S. PATENT DOCUMENTS

2006/0013817 A1   1/2006   Sahin et al.
2006/0035852 A1   2/2006   Sahin et al.

FOREIGN PATENT DOCUMENTS

EP      1004664 A1 *    5/2000
WO      WO 95/15171 A1   6/1995
WO      WO 00/02584 A2   1/2000
WO      WO 01/68709 A1   9/2001
WO      WO03-043649      5/2003
WO      WO2004/089284    10/2004

OTHER PUBLICATIONS

Lode, H.N., et al., Proc. Natl. Acad. Sci, USA, 96: 1591-1596, 1999.*
Silvestre, J.-S., et al., Nature Medicine, 11(5): 499-506, May 2005.*
Stach, C.M., et al. Cell death and Differentiation 7: 911-915, 2000.*
Prins, R.M, et al. Cancer Immunol. Immunother 51: 190-199, 2002.*
Jinushi, M., et al. Cancer Res. 68(21): 8889-8898, 2008.*
Asano, K., et al, J. Exp. Med., 200(4): 459-467, 2004.*
Bondanza, A., et al, J. Exp. med., 200(9): 1157-1165, 2004.*
van Elsas, A, et al., J. Exp. Med., 194(4): 481-489, 2001.*
Dranoff G. et al., "Vaccination with irradiated tumor cells engineered to secrete murine granulocyte-macrophage colony-stimulating factor stimulates potent, specific, and long-lasting anti-tumor immunity," PNAS 90:3539-3543 (1993).
Hanayama R. et al., "Identification of a factor that links apoptotic cells to phagocytes," Nature: 417:182-187 (2002).
Masahisa Jinushi et al., "Enhancing the clinical activity of granulocyte-macrophage colony-stimulating factor-secreting tumor cell vaccines," Immunological Reviews 222:287-298 (2008).
Taylor M.R. et al., Lactadherin (Formerly BA46), a Membrane-Associated Glycoprotein Expressed in Human Milk and Breast Carcinomas, Promotes Arg-Gly-Asp (RGD)-Dependent Cell Adhesion, DNA and Cell Biology, 16:861-869 (1997).
Giorgio Parmiani et al., "Immunotheraphy of melanoma," *Seminars in Cancer Biology*, vol. 13, No. 6, Dec. 1, 2003, pp. 391-400.
Machiels J-P. et al., "Peptide-Based Cancer Vaccines," *Seminars in Oncology Nursing*, W.B. Saunders, Amsterdam, NL, vol. 29, No. 5, Oct. 1, 2002, pp. 494-502.
Van Elsas A. et al., "Combination Immunotherapy of B16 Melanoma Using Anti-Cytoxic T Lymphocyte-Associated Antigen 4 (CTL-4) and Granulocyte/Macrophage Colony-Stimulating Factor (GM-CSF)-producing Vaccines Induces Rejection of Subcutaneous and Metastatic Tumors," *The Journal of Experimental Medicine*, Rockefeller University Press, US, vol. 190, No. 3, Aug. 2, 1999, pp. 355-366.
Davila E. et al., "Generation of Antitumor Immunity by Cyotoxic T Lymphocyte Epitope Peptide Vaccination, CpG-oligodeoxynucleotide Adjuvant, and CTLA-4 Blockade," *Cancer Research*, American Association for Cancer Research, US, vol. 63, Jun. 15, 2003, pp. 3281-3288.
Masahisa Jinushi et al., "MFG-E8-mediated uptake of apoptopic cells by APCs links the pro- and anti-inflammatory activities of GM-CSF," *The Journal of Clinical Investigation*, vol. 117, No. 7, Jul. 2, 2007, pp. 1902-1913.

* cited by examiner

*Primary Examiner* — Misook Yu
*Assistant Examiner* — Anne Holleran
(74) *Attorney, Agent, or Firm* — Cooley LLP; Ivor Elrifi; Cynthia Kozakiewicz

(57) ABSTRACT

Disclosed herein are materials and methods for treating cancer. In particular, compositions for stimulating tumor immunity through modulation of MFG-E8 are provided.

13 Claims, 16 Drawing Sheets

```
        10         20         30         40         50
MPRPRLLAAL CGALLCAPSL LVALDICSKN PCHNGGLCEE ISQEVRGDVF
        60         70         80         90        100
PSYTCTCLKG YAGNHCETKC VPLGMENGN IANSQIAASS VRVTFLGLQH
       110        120        130        140        150
WVPELARLNR AGMVNAWTPS SNDDNPWIQV NLLRRMWVTG VVTQGASRLA
       160        170        180        190        200
SHEYLKAFKV AYSINGHEFD FIHDVNKKHK EFVGNWNKNA VHVNLFETPV
       210        220        230        240        250
EAQYVRLYPT SCHTACTLRF ELLGCELNGC ANFLGLKNNS IPDKQITASS
       260        270        280        290        300
SYKTWGLHLF SWNPSYARLD KQGNFNAWVA GSYGNDQWLQ VDLGSSKEVT
       310        320        330        340        350
GIITQGARNF GSVQFVASYK VAYSNDSANW TEYQDPRTGS SKIFPGNWDN
       360        370        380    387
HSHKKNLFET PILARYVRIL PVAWHNRIAL RLELLGC
```

The RGD motif is shown in boldface at amino acids 46-48.
The EGF domain is underlined and extends from amino acid 21- 66.
The C1 domain is shown in boldface and extends from amino acid 61-125.
The C2 domain is shown in boldface and extends from amino acid 230-387.

FIGURE 12

SEQUENCE LISTING

```
<160> NUMBER OF SEQ ID NOS: 8

<210> SEQ ID NO 1
<211> LENGTH: 1392
<212> TYPE: DNA
<213> ORGANISM: Mus musculus

<400> SEQUENCE: 1
atgcaggtct cccgtgtgct ggccgcgctg tgcggcatgc tactctgcgc ctctggcctc      60
ttcgccgcgt ctggtgactt ctgtgactcc agcctgtgcc tgaacggtgg cacctgcttg     120
acgggccaag acaatgacat ctactgcctc tgccctgaag gcttcacagg ccttgtgtgc     180
aatgagactg agagaggacc atgctcccca aacccttgct acaatgatgc caatgtctg     240 gtgactttgg acacacagcg tggggacatc ttcaccgaat acatctgcca gtgccctgtg     300
ggctactcgg gcatccactg tgaaaccgag accaactact caacctgga tggagaatac     360 atgttcacca cagccgtccc caatactgcc gtccccaccc cggccccac cccgatctt     420 tccaacaacc tagcctcccg ttgttctaca cagctgggca tggaaggggg cgccattgct     480
gattcacaga tttccgcctc gtctgtgtat atgggtttca tgggcttgca gcgctggggc     540
```

```
ccggagctgg ctcgtctgta ccgcacaggg atcgtcaatg cctggacagc cagcaactat    600
gatagcaagc cctggatcca ggtgaacctt ctgcggaaga tgcgggtatc aggtgtgatg    660
acgcagggtg ccagccgtgc cgggagggcg gagtacctga agaccttcaa ggtggcttac    720
agcctcgacg gacgcaagtt tgagttcatc caggatgaaa gcggtggaga caaggagttt    780
ttgggtaacc tggacaacaa cagcctgaag gttaacatgt caacccgac tctggaggca    840 cagtacataa agctgtaccc tgtttcgtgc caccgcggct gcaccctccg cttcgagctc    900
ctgggctgtg agttgcacgg atgttctgag cccctgggcc tgaagaataa cacaattcct    960
gacagccaga tgtcagcctc cagcagctac aagacatgga acctgcgtgc ttttggctgg    1020
tacccccact tgggaaggct ggataatcag ggcaagatca tgcctggac ggctcagagc    1080 aacagtgcca aggaatggct gcaggttgac ctgggcactc agaggcaagt gacaggaatc    1140
atcacccagg gggcccgtga ctttggccac atccagtatg tggcgtccta caaggtagcc    1200
cacagtgatg atggtgtgca gtggactgta tatgaggagc aaggaagcag caaggtcttc    1260
cagggcaact tggacaacaa ctcccacaag aagaacatct tcgagaaacc cttcatggct    1320
cgctacgtgc gtgtccttcc agtgtcctgg cataaccgca tcaccctgcg cctggagctg    1380
ctgggctgtt aa                                                        1392
```

<210> SEQ ID NO 2
<211> LENGTH: 463
<212> TYPE: PRT
<213> ORGANISM: Mus musculus

<400> SEQUENCE: 2

```
Met Gln Val Ser Arg Val Leu Ala Ala Leu Cys Gly Met Leu Leu Cys
  1               5                  10                  15

Ala Ser Gly Leu Phe Ala Ala Ser Gly Asp Phe Cys Asp Ser Ser Leu
             20                  25                  30

Cys Leu Asn Gly Gly Thr Cys Leu Thr Gly Gln Asp Asn Asp Ile Tyr
         35                  40                  45

Cys Leu Cys Pro Glu Gly Phe Thr Gly Leu Val Cys Asn Glu Thr Glu
     50                  55                  60

Arg Gly Pro Cys Ser Pro Asn Pro Cys Tyr Asn Asp Ala Lys Cys Leu
 65                  70                  75                  80

Val Thr Leu Asp Thr Gln Arg Gly Asp Ile Phe Thr Glu Tyr Ile Cys
                 85                  90                  95

Gln Cys Pro Val Gly Tyr Ser Gly Ile His Cys Glu Thr Glu Thr Asn
            100                 105                 110

Tyr Tyr Asn Leu Asp Gly Glu Tyr Met Phe Thr Thr Ala Val Pro Asn
        115                 120                 125

Thr Ala Val Pro Thr Pro Ala Pro Thr Pro Asp Leu Ser Asn Asn Leu
    130                 135                 140

Ala Ser Arg Cys Ser Thr Gln Leu Gly Met Glu Gly Gly Ala Ile Ala
145                 150                 155                 160

Asp Ser Gln Ile Ser Ala Ser Ser Val Tyr Met Gly Phe Met Gly Leu
                165                 170                 175

Gln Arg Trp Gly Pro Glu Leu Ala Arg Leu Tyr Arg Thr Gly Ile Val
            180                 185                 190

Asn Ala Trp Thr Ala Ser Asn Tyr Asp Ser Lys Pro Trp Ile Gln Val
        195                 200                 205

Asn Leu Leu Arg Lys Met Arg Val Ser Gly Val Met Thr Gln Gly Ala
    210                 215                 220
```

Ser Arg Ala Gly Arg Ala Glu Tyr Leu Lys Thr Phe Lys Val Ala Tyr
225                 230                 235                 240

Ser Leu Asp Gly Arg Lys Phe Glu Phe Ile Gln Asp Glu Ser Gly Gly
            245                 250                 255

Asp Lys Glu Phe Leu Gly Asn Leu Asp Asn Asn Ser Leu Lys Val Asn
        260                 265                 270

Met Phe Asn Pro Thr Leu Glu Ala Gln Tyr Ile Lys Leu Tyr Pro Val
    275                 280                 285

Ser Cys His Arg Gly Cys Thr Leu Arg Phe Glu Leu Leu Gly Cys Glu
290                 295                 300

Leu His Gly Cys Ser Glu Pro Leu Gly Leu Lys Asn Asn Thr Ile Pro
305                 310                 315                 320

Asp Ser Gln Met Ser Ala Ser Ser Tyr Lys Thr Trp Asn Leu Arg
            325                 330                 335

Ala Phe Gly Trp Tyr Pro His Leu Gly Arg Leu Asp Asn Gln Gly Lys
                340                 345                 350

Ile Asn Ala Trp Thr Ala Gln Ser Asn Ser Ala Lys Glu Trp Leu Gln
            355                 360                 365

Val Asp Leu Gly Thr Gln Arg Gln Val Thr Gly Ile Ile Thr Gln Gly
370                 375                 380

Ala Arg Asp Phe Gly His Ile Gln Tyr Val Ala Ser Tyr Lys Val Ala
385                 390                 395                 400

His Ser Asp Asp Gly Val Gln Trp Thr Val Tyr Glu Glu Gln Gly Ser
                405                 410                 415

Ser Lys Val Phe Gln Gly Asn Leu Asp Asn Asn Ser His Lys Lys Asn
            420                 425                 430

Ile Phe Glu Lys Pro Phe Met Ala Arg Tyr Val Arg Val Leu Pro Val
        435                 440                 445

Ser Trp His Asn Arg Ile Thr Leu Arg Leu Glu Leu Leu Gly Cys
    450                 455                 460

<210> SEQ ID NO 3
<211> LENGTH: 1392
<212> TYPE: DNA
<213> ORGANISM: Mus musculus

<400> SEQUENCE: 3
atgcaggtct cccgtgtgct ggccgcgctg tgcggcatgc tactctgcgc ctctggcctc      60
ttcgccgcgt ctggtgactt ctgtgactcc agcctgtgcc tgaacggtgg cacctgcttg     120
acgggccaag acaatgacat ctactgcctc tgccctgaag gcttcacagg ccttgtgtgc     180
aatgagactg agagaggacc atgctcccca aacccttgct acaatgatgc caaatgtctg     240
gtgactttgg acacacagcg tggggaaatc ttcaccgaat acatctgcca gtgccctgtg     300
ggctactcgg gcatccactg tgaaaccgag accaactact acaacctgga tggagaatac     360
atgttcacca cagccgtccc caatactgcc gtccccaccc cggcccccac ccccgatctt     420
tccaacaacc tagcctcccg ttgttctaca cagctgggca tggaagggcg gccattgct     480 gattcacaga tttccgcctc gtctgtgtat atgggttca tgggcttgca gcgctggggc     540
ccggagctgg ctcgtctgta ccgcacaggg atcgtcaatg cctggacagc agcaactat     600 gatagcaagc cctggatcca ggtgaacctt ctgcggaaga tgcgggtatc aggtgtgatg     660
acgcagggtg ccagccgtgc cgggagggcg gagtacctga agacccttcaa ggtggcttac     720 agcctcgacg gacgcaagtt tgagttcatc caggatgaaa gcggtggaga caaggagttt     780

```
ttgggtaacc tggacaacaa cagcctgaag gttaacatgt tcaacccgac tctggaggca    840
cagtacataa agctgtaccc tgtttcgtgc caccgcggct gcaccctccg cttcgagctc    900
ctgggctgtg agttgcacgg atgttctgag cccctgggcc tgaagaataa cacaattcct    960
gacagccaga tgtcagcctc cagcagctac aagacatgga acctgcgtgc ttttggctgg   1020
tacccccact tgggaaggct ggataatcag ggcaagatca atgcctggac ggctcagagc   1080
aacagtgcca aggaatggct gcaggttgac ctgggcactc agaggcaagt gacaggaatc   1140
atcacccagg gggcccgtga ctttggccac atccagtatg tggcgtccta caaggtagcc   1200
cacagtgatg atggtgtgca gtggactgta tatgaggagc aaggaagcag caaggtcttc   1260
cagggcaact tggacaacaa ctcccacaag aagaacatct tcgagaaacc cttcatggct   1320
cgctacgtgc cgtgtccttcc agtgtcctgg cataaccgca tcaccctgcg cctggagctg   1380
ctgggctgtt aa                                                       1392
```

<210> SEQ ID NO 4
<211> LENGTH: 462
<212> TYPE: PRT
<213> ORGANISM: Mus musculus

<400> SEQUENCE: 4

```
Met Gln Val Ser Arg Val Leu Ala Ala Leu Cys Gly Met Leu Leu Cys
 1               5                   10                  15

Ala Ser Gly Leu Phe Ala Ala Ser Gly Asp Phe Cys Asp Ser Ser Leu
             20                  25                  30

Cys Leu Asn Gly Gly Thr Cys Leu Thr Gly Gln Asp Asn Asp Ile Tyr
         35                  40                  45

Cys Leu Cys Pro Glu Gly Phe Thr Gly Leu Val Cys Asn Glu Thr Glu
     50                  55                  60

Arg Gly Pro Cys Ser Pro Asn Pro Cys Tyr Asn Asp Ala Lys Cys Leu
 65                  70                  75                  80

Val Thr Leu Asp Thr Gln Arg Gly Ile Phe Thr Glu Tyr Ile Cys Gln
                 85                  90                  95

Cys Pro Val Gly Tyr Ser Gly Ile His Cys Glu Thr Glu Thr Asn Tyr
            100                 105                 110

Tyr Asn Leu Asp Gly Glu Tyr Met Phe Thr Thr Ala Val Pro Asn Thr
        115                 120                 125

Ala Val Pro Thr Pro Ala Pro Thr Pro Asp Leu Ser Asn Asn Leu Ala
    130                 135                 140

Ser Arg Cys Ser Thr Gln Leu Gly Met Glu Gly Gly Ala Ile Ala Asp
145                 150                 155                 160

Ser Gln Ile Ser Ala Ser Ser Val Tyr Met Gly Phe Met Gly Leu Gln
                165                 170                 175

Arg Trp Gly Pro Glu Leu Ala Arg Leu Tyr Arg Thr Gly Ile Val Asn
            180                 185                 190

Ala Trp Thr Ala Ser Asn Tyr Asp Ser Lys Pro Trp Ile Gln Val Asn
        195                 200                 205

Leu Leu Arg Lys Met Arg Val Ser Gly Val Met Thr Gln Gly Ala Ser
    210                 215                 220

Arg Ala Gly Arg Ala Glu Tyr Leu Lys Thr Phe Lys Val Ala Tyr Ser
225                 230                 235                 240

Leu Asp Gly Arg Lys Phe Glu Phe Ile Gln Asp Glu Ser Gly Gly Asp
                245                 250                 255
```

-continued

Lys Glu Phe Leu Gly Asn Leu Asp Asn Asn Ser Leu Lys Val Asn Met
             260                 265                 270

Phe Asn Pro Thr Leu Glu Ala Gln Tyr Ile Lys Leu Tyr Pro Val Ser
        275                 280                 285

Cys His Arg Gly Cys Thr Leu Arg Phe Glu Leu Leu Gly Cys Glu Leu
    290                 295                 300

His Gly Cys Ser Glu Pro Leu Gly Leu Lys Asn Asn Thr Ile Pro Asp
305                 310                 315                 320

Ser Gln Met Ser Ala Ser Ser Tyr Lys Thr Trp Asn Leu Arg Ala
                325                 330                 335

Phe Gly Trp Tyr Pro His Leu Gly Arg Leu Asp Asn Gln Gly Lys Ile
            340                 345                 350

Asn Ala Trp Thr Ala Gln Ser Asn Ser Ala Lys Glu Trp Leu Gln Val
        355                 360                 365

Asp Leu Gly Thr Gln Arg Gln Val Thr Gly Ile Ile Thr Gln Gly Ala
    370                 375                 380

Arg Asp Phe Gly His Ile Gln Tyr Val Ala Ser Tyr Lys Val Ala His
385                 390                 395                 400

Ser Asp Asp Gly Val Gln Trp Thr Val Tyr Glu Glu Gln Gly Ser Ser
                405                 410                 415

Lys Val Phe Gln Gly Asn Leu Asp Asn Asn Ser His Lys Lys Asn Ile
            420                 425                 430

Phe Glu Lys Pro Phe Met Ala Arg Tyr Val Arg Val Leu Pro Val Ser
        435                 440                 445

Trp His Asn Arg Ile Thr Leu Arg Leu Glu Leu Leu Gly Cys
    450                 455                 460

<210> SEQ ID NO 5
<211> LENGTH: 1164
<212> TYPE: DNA
<213> ORGANISM: Homo sapiens

<400> SEQUENCE: 5
atgccgcgcc cccgcctgct ggccgcgctg tgcggcgcgc tgctctgcgc ccccagcctc      60
ctcgtcgccc tggatatctg ttccaaaaac ccctgccaca acggtggttt atgcgaggag     120
atttcccaag aagtgcgagg agatgtcttc ccctcgtaca cctgcacgtg ccttaagggc     180
tacgcgggca accactgtga cgaaaatgt gtcgagccac tgggcatgga gaatgggaac     240
attgccaact cacagatcgc cgcctcatct gtgcgtgtga ccttcttggg tttgcagcat     300
tgggtcccgg agctggcccg cctgaaccgc gcaggcatgg tcaatgcctg gacacccagc     360
agcaatgacg ataaccctg atccaggtg aacctgctgc ggaggatgtg ggtaacaggt     420
gtggtgacgc agggtgccag ccgcttggcc agtcatgagt acctgaaggc cttcaaggtg     480
gcctacagcc ttaatggaca cgaattcgat ttcatccatg atgttaataa aaaacacaag     540
gagtttgtgg gtaactggaa caaaaacgcg gtgcatgtca acctgtttga cccctgtg     600
gaggctcagt acgtgagatt gtaccccacg agctgccaca cggcctgcac tctgcgcttt     660
gagctactgg gctgtgagct gaacggatgc gccaatcccc tgggcctgaa gaataacagc     720
atccctgaca gcagatcac ggcctccagc agctacaaga cctggggctt gcatctcttc     780
agctggaacc cctcctatgc acggctggac aagcagggca acttcaacgc ctgggttgcg     840
ggagctacg gtaacgatca gtggctgcag gtggacctgg ctcctcgaa ggaggtgaca     900
ggcatcatca cccaggggc ccgtaacttt ggctctgtcc agtttgtggc atcctacaag     960

```
gttgcctaca gtaatgacag tgcgaactgg actgagtacc aggaccccag gactggcagc    1020
agtaagatct tccctggcaa ctgggacaac cactcccaca agaagaactt gtttgagacg    1080
cccatcctgg ctcgctatgt gcgcatcctg cctgtagcct ggcacaaccg catcgccctg    1140
cgcctggagc tgctgggctg ttag                                          1164
```

<210> SEQ ID NO 6
<211> LENGTH: 387
<212> TYPE: PRT
<213> ORGANISM: Homo sapiens

<400> SEQUENCE: 6

```
Met Pro Arg Pro Arg Leu Leu Ala Ala Leu Cys Gly Ala Leu Leu Cys
 1               5                  10                  15

Ala Pro Ser Leu Leu Val Ala Leu Asp Ile Cys Ser Lys Asn Pro Cys
             20                  25                  30

His Asn Gly Gly Leu Cys Glu Glu Ile Ser Gln Glu Val Arg Gly Asp
         35                  40                  45

Val Phe Pro Ser Tyr Thr Cys Thr Cys Leu Lys Gly Tyr Ala Gly Asn
     50                  55                  60

His Cys Glu Thr Lys Cys Val Glu Pro Leu Gly Met Glu Asn Gly Asn
 65                  70                  75                  80

Ile Ala Asn Ser Gln Ile Ala Ala Ser Ser Val Arg Val Thr Phe Leu
                 85                  90                  95

Gly Leu Gln His Trp Val Pro Glu Leu Ala Arg Leu Asn Arg Ala Gly
            100                 105                 110

Met Val Asn Ala Trp Thr Pro Ser Ser Asn Asp Asp Asn Pro Trp Ile
        115                 120                 125

Gln Val Asn Leu Leu Arg Arg Met Trp Val Thr Gly Val Val Thr Gln
    130                 135                 140

Gly Ala Ser Arg Leu Ala Ser His Glu Tyr Leu Lys Ala Phe Lys Val
145                 150                 155                 160

Ala Tyr Ser Leu Asn Gly His Glu Phe Asp Phe Ile His Asp Val Asn
                165                 170                 175

Lys Lys His Lys Glu Phe Val Gly Asn Trp Asn Lys Asn Ala Val His
            180                 185                 190

Val Asn Leu Phe Glu Thr Pro Val Glu Ala Gln Tyr Val Arg Leu Tyr
        195                 200                 205

Pro Thr Ser Cys His Thr Ala Cys Thr Leu Arg Phe Glu Leu Leu Gly
    210                 215                 220

Cys Glu Leu Asn Gly Cys Ala Asn Pro Leu Gly Leu Lys Asn Asn Ser
225                 230                 235                 240

Ile Pro Asp Lys Gln Ile Thr Ala Ser Ser Tyr Lys Thr Trp Gly
                245                 250                 255

Leu His Leu Phe Ser Trp Asn Pro Ser Tyr Ala Arg Leu Asp Lys Gln
            260                 265                 270

Gly Asn Phe Asn Ala Trp Val Ala Gly Ser Tyr Gly Asn Asp Gln Trp
        275                 280                 285

Leu Gln Val Asp Leu Gly Ser Ser Lys Glu Val Thr Gly Ile Ile Thr
    290                 295                 300

Gln Gly Ala Arg Asn Phe Gly Ser Val Gln Phe Val Ala Ser Tyr Lys
305                 310                 315                 320

Val Ala Tyr Ser Asn Asp Ser Ala Asn Trp Thr Glu Tyr Gln Asp Pro
                325                 330                 335
```

```
Arg Thr Gly Ser Ser Lys Ile Phe Pro Gly Asn Trp Asp Asn His Ser
            340                 345                 350

His Lys Lys Asn Leu Phe Glu Thr Pro Ile Leu Ala Arg Tyr Val Arg
        355                 360                 365

Ile Leu Pro Val Ala Trp His Asn Arg Ile Ala Leu Arg Leu Glu Leu
        370                 375                 380

Leu Gly Cys
385

<210> SEQ ID NO 7
<211> LENGTH: 1164
<212> TYPE: DNA
<213> ORGANISM: Homo sapiens

<400> SEQUENCE: 7
atgccgcgcc ccgcctgct ggccgcgctg tgcggcgcgc tgctctgcgc cccagcctc       60 ctcgtcgccc tggatatctg ttccaaaaac ccctgccaca acgtggttt atgcgaggag     120 atttcccaag aagtgcgagg agaagtcttc ccctcgtaca cctgcacgtg ccttaagggc    180
tacgcgggca accactgtga gacgaaatgt gtcgagccac tgggcatgga gatgggaac    240 attgccaact cacagatcgc cgcctcatct gtgcgtgtga ccttcttggg tttgcagcat    300
tgggtcccgg agctggcccg cctgaaccgc gcaggcatgg tcaatgcctg gacacccagc    360
agcaatgacg ataaccctg atccaggtg aacctgctgc ggaggatgtg ggtaacaggt     420
gtggtgacgc agggtgccag ccgcttggcc agtcatgagt acctgaaggc cttcaaggtg    480
gcctacagcc ttaatggaca cgaattcgat ttcatccatg atgttaataa aaaacacaag    540
gagtttgtgg gtaactggaa caaaaacgcg gtgcatgtca acctgtttga ccccctgtg    600 gaggctcagt acgtgagatt gtaccccacg agctgccaca cggcctgcac tctgcgcttt    660
gagctactgg gctgtgagct gaacggatgc gccaatcccc tgggcctgaa gaataacagc    720
atccctgaca gcagatcac ggcctccagc agctacaaga cctggggctt gcatctcttc    780
agctggaacc cctcctatgc acggctggac aagcagggca acttcaacgc ctgggttgcg    840
gggagctacg gtaacgatca gtggctgcag gtggacctgg gctcctcgaa ggaggtgaca    900
ggcatcatca cccagggggc ccgtaacttt ggctctgtcc agtttgtggc atcctacaag    960
gttgcctaca gtaatgacag tgcgaactgg actgagtacc aggaccccag gactggcagc   1020
agtaagatct tccctggcaa ctgggacaac cactcccaca gaagaacttt gtttgagacg   1080
cccatcctgg ctcgctatgt gcgcatcctg cctgtagcct ggcacaaccg catcgccctg   1140
cgcctggagc tgctgggctg ttag                                          1164

<210> SEQ ID NO 8
<211> LENGTH: 386
<212> TYPE: PRT
<213> ORGANISM: Homo sapiens

<400> SEQUENCE: 8

Met Pro Arg Pro Arg Leu Leu Ala Ala Leu Cys Gly Ala Leu Leu Cys
1               5                   10                  15

Ala Pro Ser Leu Leu Val Ala Leu Asp Ile Cys Ser Lys Asn Pro Cys
            20                  25                  30

His Asn Gly Gly Leu Cys Glu Glu Ile Ser Gln Glu Val Arg Gly Val
        35                  40                  45

Phe Pro Ser Tyr Thr Cys Thr Cys Leu Lys Gly Tyr Ala Gly Asn His
    50                  55                  60
```

```
Cys Glu Thr Lys Cys Val Glu Pro Leu Gly Met Glu Asn Gly Asn Ile
 65              70                  75                  80

Ala Asn Ser Gln Ile Ala Ala Ser Ser Val Arg Val Thr Phe Leu Gly
             85                  90                  95

Leu Gln His Trp Val Pro Glu Leu Ala Arg Leu Asn Arg Ala Gly Met
            100                 105                 110

Val Asn Ala Trp Thr Pro Ser Ser Asn Asp Asp Asn Pro Trp Ile Gln
            115                 120                 125

Val Asn Leu Leu Arg Arg Met Trp Val Thr Gly Val Val Thr Gln Gly
    130                 135                 140

Ala Ser Arg Leu Ala Ser His Glu Tyr Leu Lys Ala Phe Lys Val Ala
145                 150                 155                 160

Tyr Ser Leu Asn Gly His Glu Phe Asp Phe Ile His Asp Val Asn Lys
                165                 170                 175

Lys His Lys Glu Phe Val Gly Asn Trp Asn Lys Asn Ala Val His Val
                180                 185                 190

Asn Leu Phe Glu Thr Pro Val Glu Ala Gln Tyr Val Arg Leu Tyr Pro
        195                 200                 205

Thr Ser Cys His Thr Ala Cys Thr Leu Arg Phe Glu Leu Leu Gly Cys
    210                 215                 220

Glu Leu Asn Gly Cys Ala Asn Pro Leu Gly Leu Lys Asn Asn Ser Ile
225                 230                 235                 240

Pro Asp Lys Gln Ile Thr Ala Ser Ser Ser Tyr Lys Thr Trp Gly Leu
                245                 250                 255

His Leu Phe Ser Trp Asn Pro Ser Tyr Ala Arg Leu Asp Lys Gln Gly
            260                 265                 270

Asn Phe Asn Ala Trp Val Ala Gly Ser Tyr Gly Asn Asp Gln Trp Leu
        275                 280                 285

Gln Val Asp Leu Gly Ser Ser Lys Glu Val Thr Gly Ile Ile Thr Gln
    290                 295                 300

Gly Ala Arg Asn Phe Gly Ser Val Gln Phe Val Ala Ser Tyr Lys Val
305                 310                 315                 320

Ala Tyr Ser Asn Asp Ser Ala Asn Trp Thr Glu Tyr Gln Asp Pro Arg
                325                 330                 335

Thr Gly Ser Ser Lys Ile Phe Pro Gly Asn Trp Asp Asn His Ser His
            340                 345                 350

Lys Lys Asn Leu Phe Glu Thr Pro Ile Leu Ala Arg Tyr Val Arg Ile
        355                 360                 365

Leu Pro Val Ala Trp His Asn Arg Ile Ala Leu Arg Leu Glu Leu Leu
    370                 375                 380

Gly Cys
385
```

TUMOR IMMUNITY

CROSS REFERENCE TO RELATED APPLICATIONS

This application is the U.S. National Phase of International Patent Application Serial No. PCT/US07/80446, filed Oct. 4, 2007, which claims priority to U.S. Provisional Patent Application No. 60/828,177, filed Oct. 4, 2006, both of which are incorporated herein by reference in their entireties.

TECHNICAL FIELD

This invention relates to oncology, and more particularly to methods and compositions for treating cancer.

BACKGROUND

The design of therapeutic strategies to stimulate potent, specific and long-lasting anti-tumor immune responses is a central objective of cancer immunology. Genetic and biochemical characterization of tumor antigens has led to the discovery that most cancer patients mount some form of immune response to developing neoplasms. However, the formation and progression of clinically evident disease implies that endogenous reactions are typically ineffectual. Two features of tumor cell biology contribute to the relatively weak anti-tumor response. First, since tumor cells are derived from normal cells, the immune system may not recognize the tumor cell as dangerous or foreign. Second, tumor cells tend to express a reduced complement of the receptors and molecules that the body relies upon to activate immune responses. Analysis of the mechanisms underlying tumor escape from immune surveillance has underscored inefficient dendritic cell-mediated tumor antigen presentation and negative immune regulation as critical factors that restrain the potency of host responses.

Approaches to stimulating and potentiating anti-tumor immunity that are under active clinical evaluation include cancer vaccines against specific tumor cell antigens or whole tumor cells, monoclonal antibodies, recombinant cytokines and adaptive cellular infusions. Phase I, II and III clinical trials to evaluate these strategies are summarized in Hodi and Dranoff (2006); Laheru and Jaffee (2005); and Finn (2003). Ongoing Phase III clinical trials to evaluate anti-cancer immunotherapy are also described on the National Cancer Institute's clinical trials database at http://cancer.gov/clinicaltrials.

The use of a patient's own tumor cells (autologous cells) to stimulate anti-tumor immunity has been the subject of active investigation for many years. Recent efforts have focused on the development of strategies to augment the efficacy of autologous tumor cell vaccines. A series of papers has uncovered the therapeutic potential of manipulating the cytokine balance within the tumor microenvironment (See, for example, Forni et al., 1988, Cancer and Met. Reviews 7: 289-309; Watanabe et al., 1989, Proc. Natl. Acad. Sci. USA, 86: 9456-9460; Gansbacher et al., 1990, Cancer Res. 50: 7820-7825; Tepper et al., 1990, Cell 60: 503-512; Fearon et al., 1990 Cell 60: 397-403; Colombo et al., 1991, J. Exptl. Med., 173: 889-897; Hock et al., 1991, J. Exptl. Med., 174: 1291-1298; Rollins et al., 1991, Mol. Cell Biol., 11: 3125-3131; Teng et al., 1991, Proc. Natl. Acad. Sci. USA, 88: 3535-3539). Seminal research involving a comparative analysis of the relative abilities of multiple immunostimulatory molecules to enhance host responses following gene transfer into tumor cells identified GM-CSF as the most potent of 33 products tested (Dranoff et al., Proc. Natl. Acad. Sci. USA 90: 3539-3543; U.S. Pat. No. 5,904,920; Dranoff, 2002, Immunol. Rev. 188: 147-154).

The ability of autologous tumor cells that have been engineered to express GM-CSF to stimulate an anti-tumor response human cancer patients has been the subject of a number of clinical trials. A variety of clinical indicators of an anti-tumor response, for example, increased survival time, tumor necrosis, tumor regression, tumor infiltration by $CD4^+$ and $CD8^+$ T lymphocytes, the presence of high titer antibodies against tumor antigens in post-immunization sera, and targeted destruction of tumor vasculature have been reported in clinical trials in patients suffering from metastatic melanoma (Soiffer et al., 1997, Hum. Gene Ther. 8: 111-123; Soiffer et al., 1998, Proc. Natl. Acad. Sci. USA. 95: 13141-13146; Soiffer et al., 2003, J. Clin. Oncol. 21: 3343-3350); non-small cell lung carcinoma (Salgia et al., 2003, J. Clin. Oncol., 21: 624-630; Nemunaitis et al., 2004, J. Natl. Cancer Inst., 96: 326-331); renal cell carcinoma (Simons et al., 1997, Cancer Res., 57: 1537-1546; Tani et al., 2004, Mol. Ther. 10: 799-816.); and prostate carcinoma (Simons et al., 1999, Cancer Res. 59: 5160-5168). The clinical trial results established that autologous tumor cell vaccination consistently improved antitumor immunity in patients with advanced cancers. Nevertheless, because the majority of patients still succumbed to progressive disease, there is a continuing need for effective and potent anti-tumor vaccines.

SUMMARY

Methods and compositions for cancer therapy are provided. In particular, the methods and compositions described herein stimulate immune-mediated tumor destruction. The present invention is based, in part, on the discovery that conditions that result in the downregulation of MFG-E8 can potentiate GM-CSF stimulated tumor destruction to provoke a clinical anti-tumor response.

MFG-E8 is expressed in a range of tissues including mammary gland, aortic smooth muscle, blood and hematopoetic cells, brain, heart, lung, kidney, spleen, pancreas, ovary and skin. Elevated levels of MFG-E8 have been found in the sera of metastatic breast cancer patients and in breast carcinoma and glioma cell lines.

MFG-E8 is intimately involved in apoptosis, the body's principal mechanism for eliminating unwanted or potentially harmful cells. Apoptotic, or programmed cell death, is essential for tissue remodeling, the selection of immune cells, and the killing of virus-infected or tumor cells. Swift removal of apoptotic cells by phagocytes, e.g., macrophages and immature dendritic cells prevents the release of potentially toxic or immunogenic intracellular material from dead cell corpses. MFG-E8 promotes phagocytic engulfment of apoptotic cells by functioning as a bridging molecule between the dying cell and the phagocyte.

Accordingly, a method of treating a cancer or cancer symptom in a subject is provided. In one embodiment, the method can include administering to the subject an effective amount of one or more tumor cell antigens that elicit an immune response against a tumor and an MFG-E8 inhibitor. The method can further include administering a composition comprising an effective amount of one or more tumor cell antigens that elicit an immune response against a tumor and an MFG-E8 inhibitor. In another aspect, the method can include administering a first composition comprising an effective amount of one or more tumor cell antigens that elicit an immune response against a tumor and administering a second composition comprising an effective amount of an MFG-E8 inhibitor. The step of administering an effective amount of one or more tumor cell antigens can include administering autologous tumor cells. The autologous tumor cells express can GM-CSF. The autologous tumor cells can harbor recombinant DNA encoding GM-CSF. The autologous tumor cells can be proliferation incompetent. The autologous tumor cells can have been irradiated. The effective amount of one or more tumor cell antigens that elicit an immune response against a tumor and an MFG-E8 inhibitor can administered by injection, infusion or inhalation.

In another embodiment, the MFG-E8 inhibitor is selected from the group consisting of an anti-MFG-E8 antibody, an anti-phosphatidyl serine antibody, an MFG-E8 polypeptide that lacks the ability to bind integrins; and an MFG-E8 polypeptide that lacks the ability to bind phosphatidyl serine. The antibody can be a monoclonal antibody, a polyclonal antibody, an Fab fragment, a chimeric antibody, a humanized antibody or a single chain antibody. Regardless of the precise molecular form of the antibody, the antibody is a pharmaceutically pure antibody.

In another aspect, the method includes administering a GM-CSF expressing cell to the subject. The GM-CSF expressing cell can secrete GM-CSF. The GM-CSF expressing cell can be a cell line engineered to express GM-CSF. The GM-CSF expressing cell can harbor recombinant DNA encoding GM-CSF. The GM-CSF expressing cell line can be K562. The GM-CSF expressing cell can be proliferation incompetent. The GM-CSF expressing cell can have been irradiated. In another embodiment, the method can include administering GM-CSF to the subject. In another aspect the method can include administering an anti-CTLA-4 antibody to the subject.

The cancer may or may not express elevated levels of MFG-E8 and can be selected from the group consisting of melanoma, breast cancer, lung cancer, kidney cancer, ovarian cancer, colon cancer and leukemia.

In another embodiment, the methods and compositions further include administering a conventional cancer therapeutic to the subject. The conventional cancer therapeutic is at least one of chemotherapy, immunotherapy, hormone ablation or surgery. In one aspect, the conventional cancer therapeutic can be an angiogenesis inhibitor. Examples of angiogenesis inhibitors include agents that block the function of vascular endothelial growth factor (VEGF) such as Bevacizumab (Avastin®, Genentech, Inc.). Other examples include, without limitation, Dalteparin (Fragmin®), Suramin ABT-510, Combretastatin A4 Phosphate, Lenalidomide, LY317615 (Enzastaurin), Soy Isoflavone (Genistein; Soy Protein Isolate) AMG-706, Anti-VEGF antibody, AZD2171, Bay 43-9006 (Sorafenib tosylate), PI-88, PTK787/ZK 222584 (Vatalanib), SU11248 (Sunitinib malate), VEGF-Trap, XL184, ZD6474, Thalidomide, ATN-161, EMD 121974 (Cilenigtide) and Celecoxib (Celebrex®).

Also provided are compositions comprising one or more tumor cell antigens that elicit an immune response against a tumor and an MFG-E8 inhibitor. The composition can include autologous tumor cells expressing one or more tumor cell antigens. The autologous tumor cells can express GM-CSF. The autologous tumor cells can harbor recombinant DNA encoding GM-CSF. The autologous tumor cells can be proliferation incompetent. The autologous tumor cells can have been irradiated.

In another aspect, the MFG-E8 inhibitor is selected from the group consisting of an anti-MFG-E8 antibody, an anti-phosphatidyl serine antibody, an MFG-E8 polypeptide that lacks the ability to bind integrins; and an MFG-E8 polypeptide that lacks the ability to bind phosphatidyl serine. The composition can include a GM-CSF expressing cell. The GM-CSF expressing cell can secrete GM-CSF. The GM-CSF expressing cell can be a cell line engineered to express GM-CSF. The GM-CSF expressing cell can harbor recombinant DNA encoding GM-CSF. The cell line can be K562. The GM-CSF expressing cell can be proliferation incompetent. The GM-CSF expressing cell can have been irradiated. In another aspect, the composition can include GM-CSF. The composition can include a pharmaceutically acceptable carrier.

In another aspect, the composition can include a conventional cancer therapeutic. The conventional cancer therapeutic can be an angiogenesis inhibitor. The angiogenesis inhibitor can inhibit vascular endothelial growth factor (VEGF) activity.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 12 depicts the human MFG-E8 amino acid sequence (SEQ ID NO:6, Genbank number NM_005928, GI:5174556) showing the locations of the EGF and C domains and the RGD motif.

DETAILED DESCRIPTION

Figure 1:
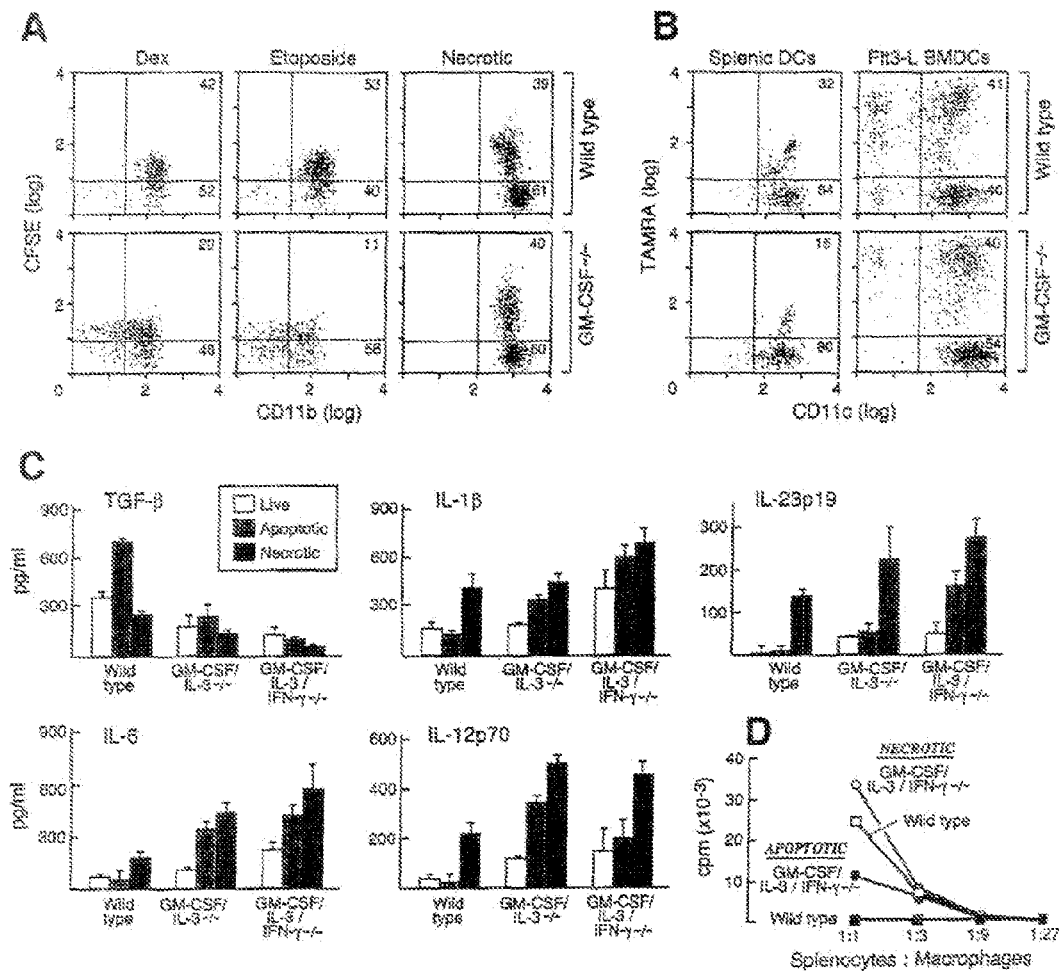
FIG. 1 depicts the results of an experiment demonstrating that GM-CSF regulates the phagocytosis of apoptotic cells. (A) Labeled cells rendered apoptotic with dexamethasone or etoposide or necrotic by freeze-thaw were added to $CD11b^+$ wild type or GM-CSF deficient peritoneal macrophages and the efficiency of ingestion measured by flow cytometry. (B) Wild type or GM-CSF deficient $CD11c^+$ dendritic cells isolated from the spleen or generated from culture of bone marrow precursors with Flt3-L were exposed to labeled apoptotic thymocytes and phagocytosis determined by flow cytometry. (C) Wild type, GM-CSF/IL-3 or GM-CSF/IL-3/IFN-$\gamma$ deficient peritoneal macrophages (three mice per group) were exposed to apoptotic or necrotic thymocytes for two hours and culture supernatants measured for TGF-$\beta$, IL-1, IL-6, IL-12p70, and IL-23p19 by ELISA. No significant differences in IL-10 or TNF-$\alpha$ production were observed (not shown). (D) Wild type or GM-CSF/IL-3/IFN-$\gamma$ deficient peritoneal macrophages were loaded with apoptotic or necrotic thymocytes for two hours and then co-cultured with wild type Balb/c splenocytes for 72 hours. Proliferation was determined by $^3$H-thymidine uptake. Results are representative of two or three independent experiments.

The mixture of cytokines produced in the tumor microenvironment plays a decisive role in determining the outcome of the host anti-tumor reaction. The cytokine granulocyte-macrophage colony stimulating factor (GM-CSF) enhances protection against tumors. The experiments described in the examples indicate that GM-CSF is required for the expression of milk fat globule EGF 8 (MFG-E8) in antigen presenting cells and that MFG-E8 mediated phagocytosis of apoptotic cells is a key determinant of GM-CSF triggered tolerance and immunity. The experiments described below demonstrate that conditions that inhibit MFG-E8 activity potentiate GM-CSF stimulated tumor destruction.

Disclosed herein are materials and methods relating to the production and use of MFG-E8-modulating compositions for the treatment, inhibition, and management of diseases and disorders associated with cancer as well as the treatment, inhibition, and management of symptoms of such diseases and disorders. In some embodiments, the MFG-E8-modulating composition includes one or more mutant forms of MFG-E8 that lack the ability to bind one or more MFG-E8 ligands. In some embodiments, the MFG-E8-modulating compositions can be administered along with, after or prior to other immunotherapies, for example, vaccination with autologous tumor cells. In some embodiments, the autologous tumor cells express GM-CSF. Alternatively, or in addition, the MFG-E8 modulating composition can include an additional GM-CSF expressing cell. Such methods may be used to enhance both clinical immunotherapy and conventional cancer therapies.

MFG-E8 Modulating Compositions

Provided herein are MFG-E8-modulating compositions. As used herein, the term "modulating" refers to an increase or decrease in the level of MFG-E8 activity to the activity of MFG-E8 in a biological sample that has not been exposed to the MFG-E8-modulator. The change in activity can be caused by an alteration in the level of MFG-E8 polypeptide or by an alteration in one or more biological activities of MFG-E8. For example, as described in greater detail below, an MFG-E8 inhibitor can be an agent that interferes with the binding of MFG-E8 to an integrin (e.g., αvβ3 and/or αvβ5) or interferes with the binding of MFG-E8 to phosphotidylserine expressed on the surface of a cell.

MFG-E8 (also known as breast epithelial antigen BA46, lactadherin, HMFG, MFGM, Medin, EDIL1, OAcGD3S, HsT19888, and SED1) is a glycoprotein found in both peripheral membrane associated and secreted forms. MFG-E8 is expressed in a range of tissues including mammary gland, aortic smooth muscle, blood and hematopoetic cells, brain, heart, lung, kidney, spleen, pancreas, ovary and skin. Elevated levels of MFG-E8 have been found in the sera of metastatic breast cancer patients and in breast carcinoma and glioma cell lines. The cDNA and amino acid sequences encoding a representative human MFG-E8 polypeptide (Genbank number NM_005928, GI:5174556) are shown in Examples 14 and 15, respectively. Other representative forms of MFG-E8 have an amino acid sequence that has 1, 2, 3, 4, 5, 10 or more amino acid changes compared to the amino acid sequence of Genbank number NM_005928, GI:5174556). Other amino acid sequences that have been identified for MFG-E8 include for example, without limitation, NP_005919, GI:5174557; Q08431 GI:2506380; AAC50549, GI:1381162; and AAH03610, GI:13177648.

The MFG-E8 polypeptide includes two repeated EGF-like domains on the N-terminal side and two repeated C (discoidin-like) domains homologous to the C1 and C2 domains of blood coagulation factors V and VIII. The second EGF-like domain of MFG-E8 contains an integrin-binding Arg-Gly-Asp (RGD) sequence motif, which is conserved in all known MFG-E8 sequences. The MFG-E8 RGD motif binds strongly to αvβ3 and αvβ5 integrins. MFG-E8 proteins also bind anionic phospholipids, especially phosphatidylserine (PS). MFG-E8 PS-binding appears to be mediated through the second C-domain (C2-domain), in the same manner as that of blood coagulation factors V and VIII. Locations of the EGF and C-domains and the RGD motif are shown in FIG. 12.

MFG-E8 is intimately involved in apoptosis, the body's principal mechanism for eliminating unwanted or potentially harmful cells. Apoptotic, or programmed cell death, is essential for tissue remodeling, the selection of immune cells, and the killing of virus-infected or tumor cells. Swift removal of apoptotic cells by phagocytes, e.g., macrophages and immature dendritic cells prevents the release of potentially toxic or immunogenic intracellular material from dead cell corpses. MFG-E8 promotes phagocytic engulfment of apoptotic cells by functioning as a bridging molecule between the dying cell and the phagocyte. Through its C2 domain, MFG-E8 specifically binds phosphatidylserine (PS) on surface of the dying cell; through its N-terminal RGD motif, MFG-E8 specifically binds αvβ3 and αvβ5 integrins on the surface of the phagocyte and thus delivers the dying cell to the phagocyte for destruction.

An MFG-E8 modulating composition can include any agent that specifically disrupts the ability of MFG-E8 to act as a bridging molecule between the apoptotic cell and the phagocyte, i.e., any agent that alters the binding to MFG-E8 to its ligands, αvβ3 integrins and PS.

MFG-E8 Polypeptides

An MFG-E8 modulator can be a mutant form of MFG-E8 that lacks or substantially lacks MFG-E8 ligand binding activity. For example, an MFG-E8 modulator can be a mutant form of the MFG-E8 polypeptide that lacks or substantially lacks the ability to bind phagocyte integrins αvβ3 and αvβ5, while retaining the ability to bind PS. Such a mutant form of MFG-E8 functions as a dominant negative mutant. i.e., a mutant that adversely affects the function of the normal, wild-type gene product within the same cell. Thus, an MFG-E8 polypeptide containing a mutation that abrogates integrin binding can efficiently opsonize apoptotic cells, but cannot deliver them to the phagocyte. Moreover, if administered in the sufficient amounts, the mutant form can occupy all or nearly all of the available PS on the apoptotic cells and thereby preclude any binding by the wild-type form. MFG-E8 activity will be reduced, thus impairing phagocytic clearance of apoptotic cells.

Any mutation that decreases the specific binding between MFG-E8 and phagocyte integrins without disrupting the binding of MFG-E8 to PS can be used. Mutations that disrupt binding to αvβ3 and αvβ5 integrins are well know in the art. (See for example, Integrins in drug targeting-RGD templates in toxins. Lu et al. Curr Pharm Des. 2006; 12(22):2749-69; Targeting RGD recognizing integrins: drug development, biomaterial research, tumor imaging and targeting. Meyer et al. Curr Pharm Des. 2006; 12(22):2723-47) A highly suitable mutation is one that converts the N-terminal RGD sequence of MFG-E8 to an RGE sequence, although any combination of 1, 2, 3, 4, 5, or 6 and more mutations in the amino acid sequence can be used as long as the resulting mutant MFG-E8 polypeptide retains PS-binding activity. The integrin-binding activity in a mutant MFG-E8 can be reduced by at least 10 percent, e.g., 10, 15, 20, 25, 30, 35, 40, 45, 50, 55, 60, 65, 70, 75, 80, 85, 90 or more than 90 percent, as compared to the integrin-binding ability in the wild-type MFG-E8 polypeptide.

Alternatively, an MFG-E8 modulating composition can be a mutant form of the MFG-E8 polypeptide that lacks or substantially lacks the ability to bind PS, while retaining the ability to bind phagocyte integrins. Such mutant forms can efficiently bind to phagocytes, but are unable to opsonize apoptotic cells. If administered at a sufficient level, the mutant form can occupy all or nearly all of the available αvβ3 and αvβ5 integrin on the relevant apoptotic cells and thereby substantially preclude binding by the wild-type form. MFG-E8 activity will be reduced, thus impairing phagocytic clearance of apoptotic cells. Mutations that disrupt PS-binding without altering the binding to integrins include, but are not limited to those in the C-2 domain. The PS-binding activity in a mutant MFG-E8 can be reduced by at least 10 percent, e.g., 10, 15, 20, 25, 30, 35, 40, 45, 50, 55, 60, 65, 70, 75, 80, 85, 90 or more than 90 percent, as compared to the PS-binding ability in the wild-type MFG-E8 polypeptide.

Mutant MFG-E8 polypeptides can be generated by any standard method of mutagenesis known in the art or they can be naturally occurring variants of MFG-E8 polypeptides that lack the integrin-binding ability or the PS-binding ability of wild-type MFG-E8. Mutations in the MFG-E8 amino acid sequence can include deletions, additions, substitutions or any combination of deletions, additions, substitutions.

Standard methods of mutagenesis typically target nucleic acids encoding the protein of interest. The terms "nucleic acid" and "polynucleotide" are used interchangeably herein, and refer to both RNA and DNA, including cDNA, genomic DNA, synthetic DNA, and DNA (or RNA) containing nucleic acid analogs. Polynucleotides can have any three-dimensional structure. A nucleic acid can be double-stranded or single-stranded (i.e., a sense strand or an antisense strand). Non-limiting examples of polynucleotides include genes, gene fragments, exons, introns, messenger RNA (mRNA), transfer RNA, ribosomal RNA, siRNA, micro-RNA, ribozymes, cDNA, recombinant polynucleotides, branched polynucleotides, plasmids, vectors, isolated DNA of any sequence, isolated RNA of any sequence, nucleic acid probes, and primers, as well as nucleic acid analogs. The nucleic acid molecules can be synthesized (for example, by phosphoramidite based synthesis) or obtained from a biological cell, such as the cell of a mammal.

Figure 13:
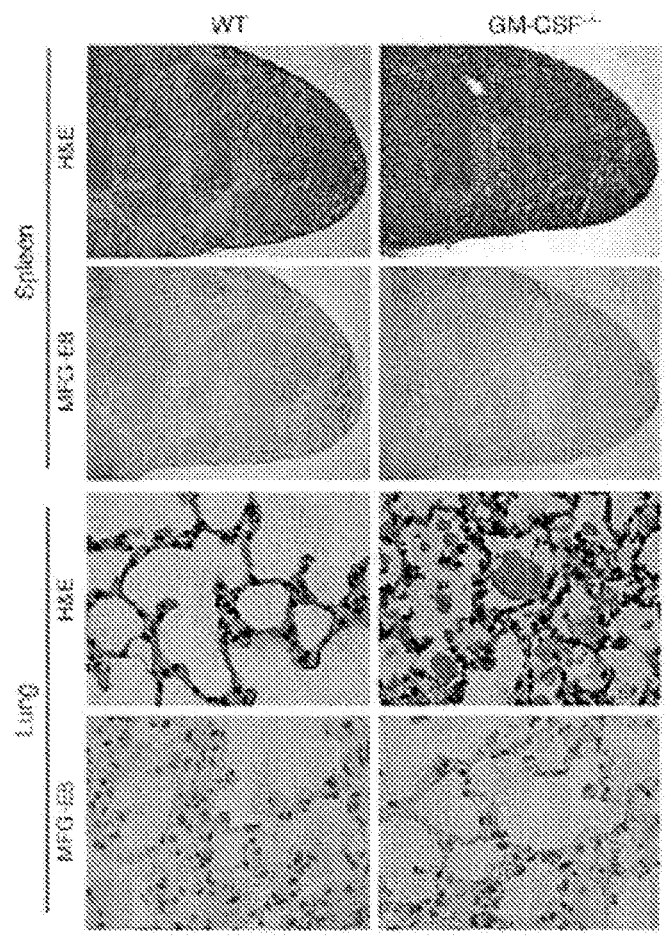
FIG. 13 depicts the results of studies showing that GM-CSF regulates steady-state MFG-E8 expression in antigen presenting cells in vivo. Anti-MFG-E8 staining was detected in germinal center macrophages and pulmonary alveolar macrophages of wild type, but not GM-CSF deficient mice. The eosinophilic material in the alveoli of GM-CSF deficient mice is pulmonary surfactant. Original magnification ×25 for spleens, ×250 for lungs.
Figure 14:
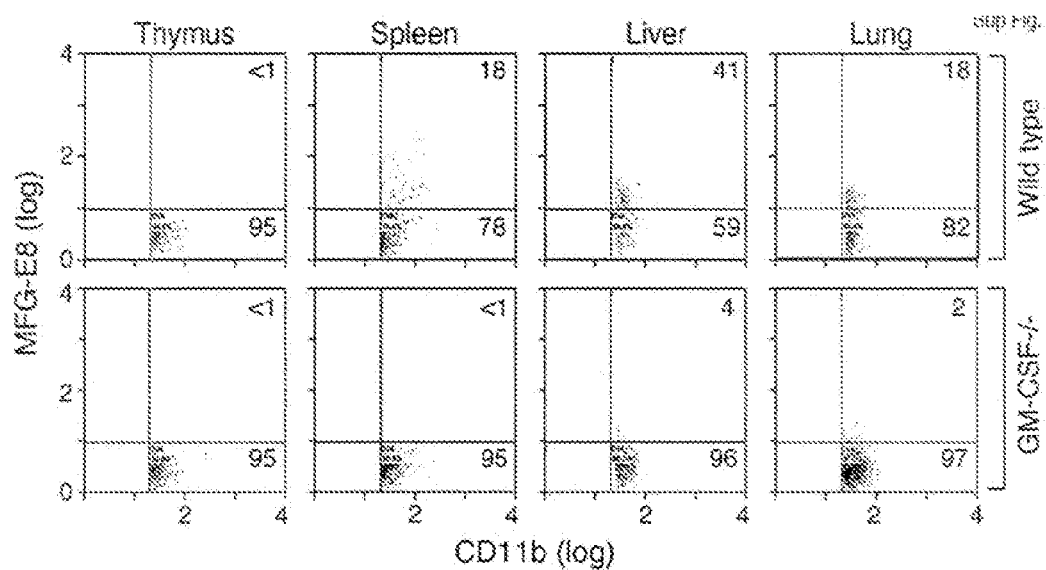
FIG. 14 depicts the results of a study showing that GM-CSF regulates MFG-E8 expression in macrophages from multiple tissues. Macrophages from thymus, spleen, liver, and lung were purified, and MFG-E8 expression was determined by flow cytometry.
Figure 15:
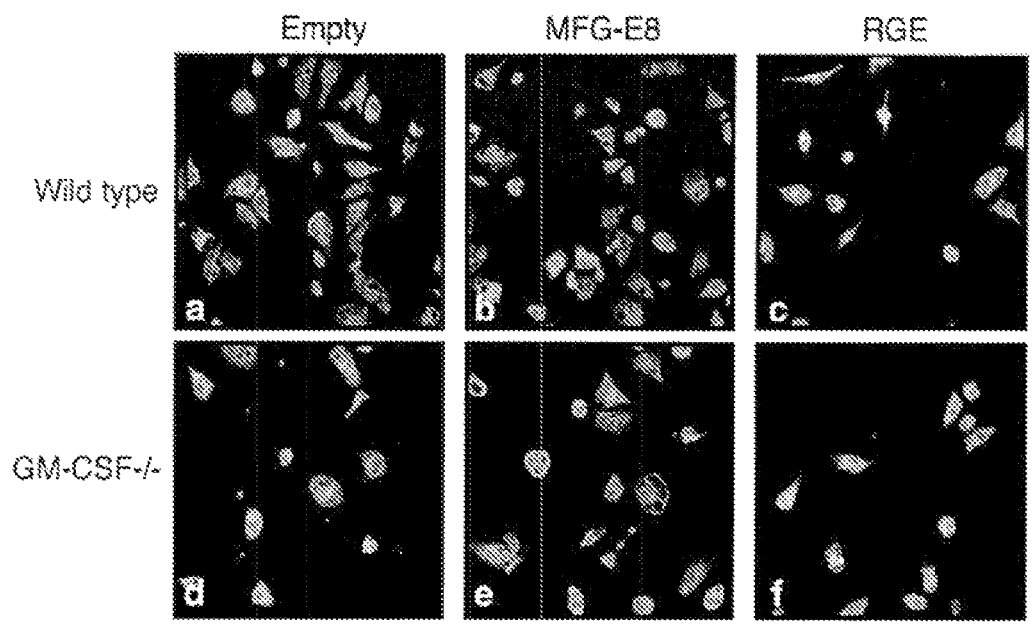
FIG. 15 depicts the results of a study showing that MFG-E8 regulates ingestion of apoptotic cells by macrophages in a GM-CSF dependent fashion. Green fluorescent-labeled peritoneal macrophages were co-cultured with red fluorescence-labeled apoptotic wild type thymocytes (dexamethasone treated). The engulfment of apoptotic cells was visualized with fluorescence microscopy, magnification ×200.

An example of an MFG-E8 wild-type cDNA sequence is shown in FIG. 12; the corresponding MFG-E8 wild-type cDNA amino acid sequence is shown in FIG. 13. An example of an MFG-E8 mutant cDNA sequence is shown in FIG. 14; the corresponding MFG-E8 mutant cDNA amino acid sequence is shown in FIG. 15. As used herein, the term "isolated" as used in reference to a nucleic acid refers to nucleic acid that is separated from other nucleic acid that is present in a genome, including nucleic acids that normally flank one or both sides of the nucleic acid in a genome (The term "isolated" as used herein with respect to nucleic acids also includes any non-naturally-occurring nucleic acid sequence since such non-naturally-occurring sequences are not found in nature and do not have immediately contiguous sequences in a naturally-occurring genome.

An isolated nucleic acid can be, for example, a DNA molecule, provided one of the nucleic acid sequences normally found immediately flanking that DNA molecule in a naturally-occurring genome is removed or absent. Thus, an isolated nucleic acid includes, without limitation, a DNA molecule that exists as a separate molecule (e.g., a chemically synthesized nucleic acid, cDNA, or genomic DNA fragment produced by PCR or restriction endonuclease treatment) independent of other sequences as well as DNA that is incorporated into a vector, an autonomously replicating plasmid, a virus (e.g., a retrovirus, lentivirus, adenovirus, or herpes virus), or into the genomic DNA of a prokaryote or eukaryote. In addition, an isolated nucleic acid can include an engineered nucleic acid such as a recombinant DNA molecule that is part of a hybrid or fusion nucleic acid. A nucleic acid existing among hundreds to millions of other nucleic acids within, for example, cDNA libraries or genomic libraries, or gel slices containing a genomic DNA restriction digest, is not to be considered an isolated nucleic acid.

The nucleic acids provided herein can be at least about 8 nucleotides in length. For example, a nucleic acid can be about 8, 9, 10-20 (e.g., 11, 12, 13, 14, 15, 16, 17, 18, 19, or 20 nucleotides in length), 20-50, 50-100 or greater than 100 nucleotides in length (e.g., greater than 150, 200, 250, 300, 350, 400, 450, 500, 750, 1000, 2000, 3000, or 4000 nucleotides in length). In some embodiments, a nucleic acid can be in a sense or antisense orientation, can be complementary to a reference sequence encoding an MFG-E8 polypeptide (e.g., FIG. 12), and can be DNA, RNA, or nucleic acid analogs. Nucleic acid analogs can be modified at the base moiety, sugar moiety, or phosphate backbone to improve, for example, stability, hybridization, or solubility of the nucleic acid.

Types of mutations that a nucleic acid encoding an MFG-E8 polypeptide can carry include, without limitation, insertions, deletions, transitions, transversions and inversions. A nucleic acid encoding an MFG-E8 polypeptide can include more than one mutation and more than one type of mutation. Such mutations, if present within the coding sequence, can result in insertions or deletions of one or more amino acids of an MFG-E8 polypeptide, conservative or non-conservative amino acid substitutions within an MFG-E8 polypeptide, or premature termination of an MFG-E8 polypeptide. Insertion or deletion of amino acids can, for example, disrupt the conformation of a functional domain. Non-conservative amino acid substitutions can result in a substantial change in the bulk of the residue side chain, and ultimately can make a substantial change in the charge, hydrophobicity, or structure of a polypeptide. Premature termination also can cause disruptions in secondary and tertiary polypeptide structure. In addition, non-coding sequence mutations (e.g., mutations in a promoter, regulatory element, or untranslated region) can alter the expression pattern properties (e.g., temporal, spatial, or developmental) of an MFG-E8 polypeptide, by, for example, changing the binding characteristics of a cis-acting transcription factor.

In some embodiments, a nucleic acid molecule provided herein can have at least 95% (e.g., 96%, 97%, 98%, 99%, 99.5%, 99.6%, 99.7%, 99.8%, 99.9%, or 100%) sequence identity with a region of a reference sequence (e.g., FIG. 12), provided that the region includes one or more mutations. Such mutations are those, for example, described herein. The region is at least ten nucleotides in length (e.g., 10, 15, 20, 50, 60, 70, 75, 100, 150, 200, 250, 300, 350, 400, 450, 500, or more than 500 nucleotides in length).

In calculating percent sequence identity, two sequences are aligned and the number of identical matches of nucleotides or amino acid residues between the two sequences is determined. The number of identical matches is divided by the length of the aligned region (i.e., the number of aligned nucleotides or amino acid residues) and multiplied by 100 to arrive at a percent sequence identity value. It will be appreciated that the length of the aligned region can be a portion of one or both sequences up to the full-length size of the shortest sequence. It also will be appreciated that a single sequence can align with more than one other sequence and hence, can have different percent sequence identity values over each aligned region. It is noted that the percent identity value is usually rounded to the nearest integer. For example, 78.1%, 78.2%, 78.3%, and 78.4% are rounded down to 78%, while 78.5%, 78.6%, 78.7%, 78.8%, and 78.9% are rounded up to 79%. It is also noted that the length of the aligned region is always an integer.

As used herein, the term "percent sequence identity" refers to the degree of identity between any given query sequence and a subject sequence. A percent identity for any query nucleic acid or amino acid sequence, e.g., a transcription factor, relative to another subject nucleic acid or amino acid sequence can be determined as follows.

A query nucleic acid or amino acid sequence is aligned to one or more subject nucleic acid or amino acid sequences using the computer program ClustalW (version 1.82) which allows alignments of nucleic acid or protein sequences to be carried out across their entire length (global alignment). ClustalW calculates the best match between a query and one or more subject sequences, and aligns them so that identities, similarities and differences can be determined. Gaps of one or more residues can be inserted into a query sequence, a subject sequence, or both, to maximize sequence alignments. For multiple alignment of nucleic acid sequences, the following parameters can be used: gap opening penalty: 15.0; gap extension penalty: 6.66; and weight transitions: yes. For fast pairwise alignment of protein sequences, the following parameters were used: word size: 1; window size: 5; scoring method: percentage; number of top diagonals: 5; gap penalty: 3. The output is a sequence alignment that reflects the relationship between sequences. ClustalW can be run, for example, at the Baylor College of Medicine Search Launcher site searchlauncher.bcm.tmc.edu/multi-align/multi-align.html and at the European Bioinformatics Institute site ebi.ac.uk/clustalw. To determine a percent identity between a query sequence and a subject sequence, the number of matching bases or amino acids in the alignment is divided by the total number of matched and mis-matched bases or amino acids excluding gaps, followed by multiplying the result by 100. The output is the percent identity of the subject sequence with respect to the query sequence.

Nucleic acid segments encoding the MFG-E8 polypeptide are readily available in the public domain. Examples of MFG-E8 sequences include, without imitation, Genbank number NM_005928, GI:5174556; BD249734, GI:33059504; S56151, GI:235396; and BC003610, GI:34785035. Alternatively, the isolated nucleic acids provided herein can be produced by standard techniques, including, without limitation, common molecular cloning and chemical nucleic acid synthesis techniques. For example, polymerase chain reaction (PCR) techniques can be used to obtain an isolated nucleic acid containing a mutation. PCR refers to a procedure or technique in which target nucleic acids are enzymatically amplified. Sequence information from the ends of the region of interest or beyond typically is employed to design oligonucleotide primers that are identical in sequence to opposite strands of the template to be amplified. PCR can be used to amplify specific sequences from DNA as well as RNA, including sequences from total genomic DNA or total cellular RNA. Primers are typically 14 to 40 nucleotides in length, but can range from 10 nucleotides to hundreds of nucleotides in length. General PCR techniques are described, for example in PCR Primer: A Laboratory Manual, ed. by Dieffenbach and Dveksler, Cold Spring Harbor Laboratory Press, 1995. When using RNA as a source of template, reverse transcriptase can be used to synthesize cDNA strands. Ligase chain reaction, strand displacement amplification, self-sustained sequence replication, or nucleic acid sequence-based amplification also can be used to obtain isolated nucleic acids. See, for example, Lewis, Genetic Engineering News, 12(9):1 (1992); Guatelli et al., Proc. Natl. Acad. Sci. USA, 87:1874-1878 (1990); and Weiss, Science, 254:1292 (1991).

The isolated nucleic acids provided herein also can be chemically synthesized, either as a single nucleic acid molecule (e.g., using automated DNA synthesis in the 3' to 5' direction using phosphoramidite technology) or as a series of oligonucleotides. For example, one or more pairs of long oligonucleotides (e.g., >100 nucleotides) can be synthesized that contain the desired sequence, with each pair containing a short segment of complementarity (e.g., about 15 nucleotides) such that a duplex is formed when the oligonucleotide pair is annealed. A DNA polymerase can be used to extend the oligonucleotides, resulting in a single, double-stranded nucleic acid molecule per oligonucleotide pair, which then can be ligated into a vector.

Mutagenesis methods can include both random and targeted approaches. Random mutagenesis approaches include, but are not limited to, exposure of cells to mutagenizing chemicals or agents, such as ultraviolet light, error-prone PCR, rolling circle amplification and the use of bacterial mutator strains. Targeted approached involving site-directed mutagenesis can rely upon either PCR or non-PCR based techniques. It will be appreciated that a number of nucleic acids can encode a polypeptide having a particular amino acid sequence. The degeneracy of the genetic code is well known to the art; i.e., for many amino acids, there is more than one nucleotide triplet that serves as the codon for the amino acid.

Standard molecular biology methods can be used to confirm the presence of a mutation in an MFG-E8 nucleotide sequence. Nucleic acids encoding mutant forms of MFG-E8 can be cloned into a variety of vectors for further analysis. A vector generally is a replicon, such as a plasmid, phage, or cosmid, into which another DNA segment may be inserted so as to bring about the replication of the inserted segment. Usually, a vector is capable of replication when associated with the proper control elements. Suitable vector backbones include, for example, those routinely used in the art such as plasmids, viruses, artificial chromosomes, BACs, YACs, or PACs. The term "vector" includes cloning and expression vectors, as well as viral vectors and integrating vectors. An "expression vector" is a vector that includes a regulatory region. Suitable expression vectors include, without limitation, plasmids and viral vectors derived from, for example, bacteriophage, baculoviruses, and retroviruses. Numerous vectors and expression systems are commercially available from such corporations as Novagen (Madison, Wis.), Clontech (Palo Alto, Calif.), Stratagene (La Jolla, Calif.), and Invitrogen/Life Technologies (Carlsbad, Calif.).

Vectors typically contain one or more regulatory regions. The term "regulatory region" refers to nucleotide sequences that influence transcription or translation initiation and rate, and stability and/or mobility of a transcription or translation product. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, and introns.

As used herein, the term "operably linked" refers to positioning of a regulatory region and a sequence to be transcribed in a nucleic acid so as to influence transcription or translation of such a sequence. For example, to bring a coding sequence under the control of a promoter, the translation initiation site of the translational reading frame of the polypeptide is typically positioned between one and about fifty nucleotides downstream of the promoter. A promoter can, however, be positioned as much as about 5,000 nucleotides upstream of the translation initiation site, or about 2,000 nucleotides upstream of the transcription start site. A promoter typically comprises at least a core (basal) promoter. A promoter also may include at least one control element, such as an enhancer sequence, an upstream element or an upstream activation region (UAR). The choice of promoters to be included depends upon several factors, including, but not limited to, efficiency, selectability, inducibility, desired expression level, and cell- or tissue-preferential expression. It is a routine matter for one of skill in the art to modulate the expression of a coding sequence by appropriately selecting and positioning promoters and other regulatory regions relative to the coding sequence.

The vectors also can include, for example, origins of replication, scaffold attachment regions (SARs), and/or markers. A marker gene can confer a selectable phenotype, e.g., antibiotic resistance, on a cell. In addition, an expression vector can include a tag sequence designed to facilitate manipulation or detection (e.g., purification or localization) of the expressed polypeptide. Tag sequences, such as green fluorescent protein (GFP), glutathione S-transferase (GST), polyhistidine, c-myc, hemagglutinin, or Flag™ tag (Kodak, New Haven, Conn.) sequences typically are expressed as a fusion with the encoded polypeptide. Such tags can be inserted anywhere within the polypeptide, including at either the carboxyl or amino terminus.

The expression vectors disclosed herein containing the above described coding can be used, for example, to transfect or transduce either prokaryotic (e.g., bacteria) cells or eukaryotic cells (e.g., yeast, insect, or mammalian) cells. Such cells can then be used, for example, for large or small scale in vitro production of the mutant MFG-E8 polypeptide by methods known in the art. In essence, such methods involve culturing the cells under conditions which maximize production of the mutant MFG-E8 polypeptide and isolating the mutant MFG-E8 polypeptide from the cells or from the culture medium.

Once the mutant MFG-E8 polypeptides have been generated, the effect of the mutation on MFG-E8 biological activity can be confirmed. For example, the wild type and mutant forms can be compared for their ability to bind isolated RGD fragments, full length integrins, or PS in vitro and to induce phagocytosis in cell-based assay systems.

Antibodies

An MFG-E8 inhibitor can be an antibody. In one embodiment, the antibody can be an anti-MFG-E8 antibody. In another embodiment, the antibody can be an anti-PS antibody. Anti-PS antibodies and ligands for binding PS are described in U.S. Pat. Nos. 6,406,693, 6,818,213, 6,312,694, and 6,783,760 and in Beck et al. 2006 Int J Cancer 118: 2639-43. Anti-PS antibodies e.g., Bavituximab (Peregrine Pharmaceuticals), are also described on the National Cancer Institute's clinical trials database at http//canger.gov/clinical trials. In another embodiment, the antibody can be an antibody that specifically recognizes and blocks the activity of a molecule that functions in the uptake of PS. Examples of PS-uptake targets include Del-1 (see for example, without limitation, NP_005702, GI:313 17224), Gas6 (see for example, without limitation, NP_000811, GI:4557617), Mer (see for example, without limitation, NP_006334, GI:66932918) and members of the Tyro family (see for example, without limitation, NP_006284, GI:27597078.) As used herein, useful antibodies can include: monoclonal and polyclonal antibodies, single chain antibodies, chimeric antibodies, bifunctional/bispecific antibodies, humanized antibodies, human antibodies, and complementary determining region (CDR)-grafted antibodies, that are specific for the target protein or fragments thereof, and also include antibody fragments, including Fab, Fab', F(ab')2, scFv, Fv, camelbodies, or microantibodies.

Monoclonal antibodies are homogeneous antibodies of identical antigenic specificity produced by a single clone of antibody-producing cells. Polyclonal antibodies generally can recognize different epitopes on the same antigen and that are produced by more than one clone of antibody producing cells. Each monoclonal antibody is directed against a single determinant on the antigen. In addition to their specificity, the monoclonal antibodies are advantageous in that they may be synthesized uncontaminated by other antibodies. The modifier, monoclonal, indicates the character of the antibody as being obtained from a substantially homogeneous population of antibodies, and is not to be construed as requiring production of the antibody by any particular method. For example, the monoclonal antibodies may be made by the hybridoma method first described by Kohler et al., Nature, 256:495 (1975), or may be made by recombinant DNA methods (see, e.g., U.S. Pat. No. 4,816,567). The monoclonal antibodies may also be isolated from phage antibody libraries using the techniques described in Clackson et al., Nature, 352:624-628 (1991) and Marks et al., J. Mol. Biol., 222:581-597 (1991), for example.

The monoclonal antibodies herein can include chimeric antibodies, i.e., antibodies that typically have a portion of the heavy and/or light chain identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., Proc. Natl. Acad. Sci. USA, 81:6851-6855 (1984)). Chimeric antibodies of interest include primatized antibodies comprising variable domain antigen-binding sequences derived from a non-human primate (e.g. apes, Old World monkeys, New World monkeys, prosimians) and human constant region sequences.

Antibody fragments generally include a portion of an intact antibody. In some embodiments, the portion of an intact antibody can be the antigen-binding or variable region of the corresponding intact antibody. Examples of antibody fragments include Fab, Fab', F(ab')2, and Fv fragments; diabodies; linear antibodies (Zapata et al., Protein Eng. 8(10): 1057-1062 [1995]); single-chain antibody molecules; and multispecific antibodies formed from antibody fragment(s).

An intact antibody is one that comprises an antigen-binding variable region as well as a light chain constant domain ($C_L$) and heavy chain constant domains, $C_{H1}$, $C_{H2}$ and $C_{H3}$. The constant domains may be native sequence constant domains (e.g. human native sequence constant domains) or amino acid sequence variants thereof. In some embodiments the intact antibody has one or more effector functions.

A wide variety of antibody/immunoglobulin frameworks or scaffolds can be employed so long as the resulting polypeptide includes at least one binding region that is specific for the target protein. Such frameworks or scaffolds include the five main idiotypes of human immunoglobulins, or fragments thereof (such as those disclosed elsewhere herein), and include immunoglobulins of other animal species, preferably having humanized aspects. Single heavy-chain antibodies such as those identified in camelids are of particular interest in this regard. Novel frameworks, scaffolds and fragments continue to be discovered and developed by those skilled in the art.

One can generate non-immunoglobulin based antibodies using non-immunoglobulin scaffolds onto which CDRs of the anti-MFG-E8 or anti-PS antibody can be grafted. Any non-immunoglobulin framework and scaffold know to those in the art may be used, as long as the framework or scaffold includes a binding region specific for the target. Examples of non-immunoglobulin frameworks or scaffolds include, but are not limited to, Adnectins (fibronectin) (Compound Therapeutics, Inc., Waltham, Mass.), ankyrin (Molecular Partners AG, Zurich, Switzerland), domain antibodies (Domantis, Ltd (Cambridge, Mass.) and Ablynx nv (Zwijnaarde, Belgium)), lipocalin (Anticalin) (Pieris Proteolab AG, Freising, Germany), small modular immuno-pharmaceuticals (Trubion Pharmaceuticals Inc., Seattle, Wash.), maxybodies (Avidia, Inc. (Mountain View, Calif.)), Protein A (Affibody AG, Sweden) and affilin (gamma-crystallin or ubiquitin) (Scil Proteins GmbH, Halle, Germany).

The term polypeptide as used herein refers to a compound of two or more subunit amino acids, amino acid analogs, or other peptidomimetics, regardless of post-translational modification, e.g., phosphorylation or glycosylation. The subunits may be linked by peptide bonds or other bonds such as, for example, ester or ether bonds. The term "amino acid" refers to natural and/or unnatural or synthetic amino acids, including D/L optical isomers. Full-length proteins, analogs, mutants, and fragments thereof are encompassed by this definition.

The anti-MICA and/or the anti-PS antibody can be a monoclonal antibody, a polyclonal antibody, a chimeric antibody, a human antibody, a humanized antibody, a single-chain antibody, or an Fab fragment. In some embodiments the antibody has a binding affinity less than about $1\times10^5$ Ka for an antigen other than MFG-E8 or PS. In some embodiments, the anti-MFG-E8 antibody is a monoclonal antibody which binds to MFG-E8 with an affinity of at least $1\times10^8$ Ka. In some embodiments, the anti-PS antibody is a monoclonal antibody which binds to PS with an affinity of at least $1\times10^8$ Ka.

Monoclonal antibodies can be prepared using the method of Kohler et al. (1975) Nature 256:495-496, or a modification thereof. Typically, a mouse is immunized with a solution containing an antigen. Immunization can be performed by mixing or emulsifying the antigen-containing solution in saline, in some embodiments in an adjuvant such as Freund's complete adjuvant, and injecting the mixture or emulsion parenterally. Any method of immunization known in the art may be used to obtain the monoclonal antibodies. After immunization of the animal, the spleen (and optionally, several large lymph nodes) are removed and dissociated into single cells. The spleen cells may be screened by applying a cell suspension to a plate or well coated with the antigen of interest. The B cells expressing membrane bound immunoglobulin specific for the antigen bind to the plate and are not rinsed away. Resulting B cells, or all dissociated spleen cells, are then induced to fuse with myeloma cells to form hybridomas, and are cultured in a selective medium. The resulting cells are plated by serial or limiting dilution and are assayed for the production of antibodies that specifically bind the antigen of interest (and that do not bind to unrelated antigens). The selected monoclonal antibody (mAb)-secreting hybridomas are then cultured either in vitro (e.g., in tissue culture bottles or hollow fiber reactors), or in vivo (as ascites in mice).

In some embodiments the anti-MFG-E8 and/or the anti-PS antibody is a humanized antibody. Human antibodies can be produced using techniques known in the art, including phage display libraries (Hoogenboom and Winter, J. Mol. Biol., 227:381 (1991); Marks et al., J. Mol. Biol., 222:581 (1991)). The techniques of Cole et al. and Boerner et al. are also available for the preparation of human monoclonal antibodies (Cole et al., Monoclonal Antibodies and Cancer Therapy, Alan R. Liss, p. 77 (1985) and Boerner et al., J. Immunol., 147(1):86 95 (1991)).

Humanized antibodies may be engineered by a variety of methods including, for example: (1) grafting the non-human complementarity determining regions (CDRs) onto a human framework and constant region (a process referred to in the art as humanizing), or, alternatively, (2) transplanting the entire non-human variable domains, but providing them with a human-like surface by replacement of surface residues (a process referred to in the art as veneering). Humanized antibodies can include both humanized and veneered antibodies. Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., Bio/Technology 10, 779-783 (1992); Lonberg et al., Nature 368 856-859 (1994); Morrison, Nature 368, 812-13 (1994); Fishwild et al., Nature Biotechnology 14, 845-51 (1996); Neuberger, Nature Biotechnology 14, 826 (1996); Lonberg and Huszar, Intern. Rev. Immunol. 13 65-93 (1995); Jones et al., Nature 321:522-525 (1986); Morrison et al., Proc. Natl. Acad. Sci, U.S.A., 81:6851-6855 (1984); Morrison and Oi, Adv. Immunol., 44:65-92 (1988); Verhoeyer et al., Science 239:1534-1536 (1988); Padlan, Molec. Immun. 28:489-498 (1991); Padlan, Molec. Immunol. 31(3):169-217 (1994); and Kettleborough, C. A. et al., Protein Eng. 4(7):773-83 (1991) each of which is incorporated herein by reference.

In addition to chimeric and humanized antibodies, fully human antibodies can be derived from transgenic mice having human immunoglobulin genes (see, e.g., U.S. Pat. Nos. 6,075,181, 6,091,001, and 6,114,598, all of which are incorporated herein by reference), or from phage display libraries of human immunoglobulin genes (see, e.g. McCafferty et al., Nature, 348:552-554 (1990). Clackson et al., Nature, 352:624-628 (1991), and Marks et al., J. Mol. Biol., 222:581-597 (1991)). In some embodiments, antibodies may be produced and identified by scFv-phage display libraries. Antibody phage display technology is available from commercial sources such as from Morphosys.

As an alternative to the use of hybridomas for expression, antibodies can be produced in a cell line such as a CHO or myeloma cell line, as disclosed in U.S. Pat. Nos. 5,545,403; 5,545,405; and 5,998,144; each incorporated herein by reference. Briefly the cell line is transfected with vectors capable of expressing a light chain and a heavy chain, respectively. By transfecting the two proteins on separate vectors, chimeric antibodies can be produced. Immunol. 147:8; Banchereau et al. (1991) Clin. Immunol. Spectrum 3:8; and Banchereau et al. (1991) Science 251:70; all of which are herein incorporated by reference.

A complementarity determining region of an antibody typically includes amino acid sequences that together define the binding affinity and specificity of the natural Fv region of a native immunoglobulin binding site. See, e.g., Chothia et al., J. Mol. Biol. 196:901-917 (1987); Kabat et at, U.S. Dept. of Health and Human Services NIH Publication No. 91-3242 (1991). A constant region of an antibody typically includes the portion of the antibody molecule that confers effector functions, including for example, the portion that binds to the Fc receptor on dendritic cells. In some embodiments, mouse constant regions can be substituted by human constant regions. For example, the constant regions of humanized antibodies are derived from human immunoglobulins. The heavy chain constant region can be selected from any of the five isotypes: alpha, delta, epsilon, gamma or mu. One method of humanizing antibodies comprises aligning the non-human heavy and light chain sequences to human heavy and light chain sequences, selecting and replacing the non-human framework with a human framework based on such alignment, molecular modeling to predict the conformation of the humanized sequence and comparing to the conformation of the parent antibody. This process is followed by repeated back mutation of residues in the CDR region that disturb the structure of the CDRs until the predicted conformation of the humanized sequence model closely approximates the conformation of the non-human CDRs of the parent non-human antibody. Such humanized antibodies may be further derivatized to facilitate uptake and clearance, e.g., via Ashwell receptors. See, e.g., U.S. Pat. Nos. 5,530,101 and 5,585,089 which are incorporated herein by reference.

Human antibodies can also be produced using transgenic animals that are engineered to contain human immunoglobulin loci. For example, WO 98/24893 discloses transgenic animals having a human Ig locus wherein the animals do not produce functional endogenous immunoglobulins due to the inactivation of endogenous heavy and light chain loci. WO 91/10741 also discloses transgenic non-primate mammalian hosts capable of mounting an immune response to an immunogen, wherein the antibodies have primate constant and/or variable regions, and wherein the endogenous immunoglobulin-encoding loci are substituted or inactivated. WO 96/30498 discloses the use of the Cre/Lox system to modify the immunoglobulin locus in a mammal, such as to replace all or a portion of the constant or variable region to form a modified antibody molecule. WO 94/02602 discloses non-human mammalian hosts having inactivated endogenous Ig loci and functional human Ig loci. U.S. Pat. No. 5,939,598 discloses methods of making transgenic mice in which the mice lack endogenous heavy chains, and express an exogenous immunoglobulin locus comprising one or more xenogeneic constant regions. Antibodies can also be produced using human engineering techniques as discussed in U.S. Pat. No. 5,766,886, which is incorporated herein by reference.

Using a transgenic animal described above, an immune response can be produced to a selected antigenic molecule, and antibody-producing cells can be removed from the animal and used to produce hybridomas that secrete human monoclonal antibodies. Immunization protocols, adjuvants, and the like are known in the art, and are used in immunization of, for example, a transgenic mouse as described in WO 96/33735. The monoclonal antibodies can be tested for the ability to inhibit or neutralize the biological activity or physiological effect of the corresponding protein.

Fragments of antibodies are suitable for use in the methods provided so long as they retain the desired affinity and specificity of the full-length antibody. Thus, a fragment of an anti-MFG-E8 and/or the anti-PS antibody will retain an ability to bind to MFG-E8 or PS in the Fv portion and the ability to bind the Fc receptor on dendritic cells in the FC portion. Such fragments are characterized by properties similar to the corresponding full-length antibody, that is, the fragments will specifically bind a human MFG-E8 or PS antigen expressed on the surface of a human cell.

Also provided are antibodies that are SMIPs or binding domain immunoglobulin fusion proteins specific for target protein. These constructs are single-chain polypeptides comprising antigen binding domains fused to immunoglobulin domains necessary to carry out antibody effector functions. See e.g., WO03/041600, U.S. Patent publication 20030133939 and US Patent Publication 20030118592.

Any form of MFG-E8 or PS can be used to generate the anti-MFG-E8 and/or the anti-PS antibody respectively, including, in the case of MFG-E8, the full length polypeptide or epitope-bearing fragments thereof. Highly suitable anti-MFG-E8 and anti-PS antibodies are those of sufficient affinity and specificity to recognize and bind to their respective targets in vivo. As used herein, the term epitope refers to an antigenic determinant of a polypeptide. In some embodiments an epitope may comprise 3 or more amino acids in a spatial conformation which is unique to the epitope. In some embodiments epitopes are linear or conformational epitopes. Generally an epitope consists of at least 4, at least 6, at least 8, at least 10, and at least 12 such amino acids, and more usually, consists of at least 8-10 such amino acids. Methods of determining the spatial conformation of amino acids are known in the art, and include, for example, x-ray crystallography and 2-dimensional nuclear magnetic resonance.

In some embodiments, the antibodies specifically bind to one or more epitopes in an extracellular domain of MFG-E8. Suitable antibodies can recognize linear or conformational epitopes, or combinations thereof. It is to be understood that these peptides may not necessarily precisely map to one epitope, but may also contain an MFG-E8 sequence that is not immunogenic.

Methods of predicting other potential epitopes to which an antibody can bind are well-known to those of skill in the art and include without limitation, Kyte-Doolittle Analysis (Kyte, J. and Dolittle, R. F., J. Mol. Biol. (1982) 157:105-132), Hopp and Woods Analysis (Hopp, T. P. and Woods, K. R., Proc. Natl. Acad. Sci. USA (1981) 78:3824-3828; Hopp, T. J. and Woods, K. R., Mol. Immunol. (1983) 20:483-489; Hopp, T. J., J. Immunol. Methods (1986) 88:1-18.), Jameson-Wolf Analysis (Jameson, B. A. and Wolf, H., Comput. Appl. Biosci. (1988) 4:181-186.), and Emini Analysis (Emini, E. A., Schlief, W. A., Colonno, R. J. and Wimmer, E., Virology (1985) 140:13-20.). In some embodiments, potential epitopes are identified by determining theoretical extracellular domains. Analysis algorithms such as TMpred (see K. Hofmann & W. Stoffel (1993) TMbase—A database of membrane spanning proteins segments Biol. Chem. Hoppe-Seyler 374,166) or TMHMM (A. Krogh, B. Larsson, G. von Heijne, and E. L. L. Sonnhammer. Predicting transmembrane protein topology with a hidden Markov model: Application to complete genomes. Journal of Molecular Biology, 305(3):567-580, January 2001) can be used to make such predictions. Other algorithms, such as SignalP 3.0 (Bednsten et al, (2004) J Mol Biol. 2004 Jul. 16; 340(4):783-95) can be used to predict the presence of signal peptides and to predict where those peptides would be cleaved from the full-length protein. The portions of the proteins on the outside of the cell can serve as targets for antibody interaction.

Specifically binding antibodies are can be antibodies that 1) exhibit a threshold level of binding activity; and/or 2) do not significantly cross-react with known related polypeptide molecules. The binding affinity of an antibody can be readily determined by one of ordinary skill in the art, for example, by Scatchard analysis (Scatchard, Ann. NY Acad. Sci. 51: 660-672, 1949). In some embodiments the antibodies can bind to their target epitopes or mimetic decoys at least 1.5-fold, 2-fold, 5-fold 10-fold, 100-fold, $10^3$-fold, $10^4$-fold, $10^5$-fold, $10^6$-fold or greater for the target cancer-associated polypeptide than to other proteins predicted to have some homology to MFG-E8.

In some embodiments the antibodies bind with high affinity of $10^{-4}$M or less, $10^{-7}$M or less, $10^{-9}$M or less or with subnanomolar affinity (0.9, 0.8, 0.7, 0.6, 0.5, 0.4, 0.3, 0.2, 0.1 nM or even less). In some embodiments the binding affinity of the antibodies for MICA is at least $1\times10^6$ Ka. In some embodiments the binding affinity of the antibodies for MICA is at least $5\times10^6$ Ka, at least $1\times10^7$ Ka, at least $2\times10^7$ Ka, at least $1\times10^8$ Ka, or greater. Antibodies may also be described or specified in terms of their binding affinity to an MFG-E8 polypeptide or PS. In some embodiments binding affinities include those with a $K_d$ less than $5\times10^{-2}$ M, $10^{-2}$ M, $5\times10^{-3}$ M, $10^{-3}$ M, $5\times10^{-4}$ M, $10^{-4}$ M, $5\times10^{-5}$ M, $10^{-5}$ M, $5\times10^{-6}$ M, $10^{-6}$ M, $5\times10^{-7}$ M, $10^{-7}$ M, $5\times10^{-8}$ M, $10^{-8}$ M, $5\times10^{-9}$ M, $5\times10^{-10}$ M, $10^{-10}$ M, $5\times10^{-11}$ M, $10^{-11}$M, $5\times10^{-12}$M, $10^{-12}$ M, $5\times10^{-13}$ M, $10^{-13}$ M, $5\times10^{-14}$ M, $10^{-14}$ M, $5\times10^{-15}$ M, or $10^{-15}$ M, or less.

In some embodiments, the antibodies do not bind to known related polypeptide molecules; for example, they bind MFG-E8 polypeptide but not known related polypeptides using a standard immunoblot analysis (Ausubel et al., Current Protocols in Molecular Biology, 1994).

In some embodiments, antibodies may be screened against known related polypeptides to isolate an antibody population that specifically binds to MFG-E8 polypeptides or to PS. For example, antibodies specific to human MFG-E8 polypeptides will flow through a column comprising MFG-E8-related proteins (with the exception of MFG-E8) adhered to insoluble matrix under appropriate buffer conditions. Such screening allows isolation of polyclonal and monoclonal antibodies non-crossreactive to closely related polypeptides (Antibodies: A Laboratory Manual, Harlow and Lane (eds.), Cold Spring Harbor Laboratory Press, 1988; Current so Protocols in Immunology, Cooligan et al. (eds.), National Institutes of Health, John Wiley and Sons, Inc., 1995). Screening and isolation of specific antibodies is well known in the art (see, Fundamental Immunology, Paul (eds.), Raven Press, 1993; Getzoff et al., Adv. in Immunol. 43: 1-98, 1988; Monoclonal Antibodies: Principles and Practice, Goding, J. W. (eds.), Academic Press Ltd., 1996; Benjamin et al., Ann. Rev. Immunol. 2: 67-101, 1984). Representative examples of such assays include: concurrent immunoelectrophoresis, radioimmunoassay (RIA), radioimmunoprecipitation, enzyme-linked immunosorbent assay (ELISA), dot blot or Western blot assay, inhibition or competition assay, and sandwich assay.

Antibodies can be purified by chromatographic methods known to those of skill in the art, including ion exchange and gel filtration chromatography (for example, Caine et al., Protein Expr. Purif. (1996) 8(2):159-166). Alternatively or in addition, antibodies can be purchased from commercial sources, for example, Invitrogen (Carlsbad, Calif.); MP Biomedicals (Solon, Ohio); Nventa Biopharmaceuticals (San Diego, Calif.) (formerly Stressgen); Serologicals Corp. (Norcross, Ga.).

The MFG-E8-inhibitor can include a monoclonal antibody that recognizes a single MFG-E8 epitope or can be any combination of monoclonal or polyclonal antibodies recognizing one of more different MFG-E8 epitopes. Thus the MFG-E8-inhibitor can include antibodies recognize 2, 3, 4, 5, 6, 7, 8, 10, 20 or more different MFG-E8 epitopes.

In some embodiments, antibodies may act as MFG-E8 antagonists. For example, in some embodiments the antibodies can disrupt the interactions between MFG-E8 and the αvβ3 and/or αvβ5 integrins either partially or fully. In some embodiments the antibodies can disrupt the interactions between MFG-E8 and P/S either partially or fully. In some embodiments, antibodies are provided that modulate ligand activity or receptor activity by at least 95%, at least 90%, at least 85%, at least 80%, at least 75%, at least 70%, at least 60%, or at least 50% compared to the activity in the absence of the antibody.

In some embodiments neutralizing antibodies are provided. In some embodiments the neutralizing antibodies act as receptor antagonists, i.e., inhibiting either all or a subset of the biological activities of the ligand-mediated receptor activation. In some embodiments the antibodies may be specified as agonists, antagonists or inverse agonists for biological activities comprising the specific biological activities of the peptides disclosed herein.

In some embodiments, the MFG-E8-inhibiting composition can include a combination of anti-MFG-E8 antibodies and antibodies against cytotoxic lymphocyte antigen-4 (CTLA-4). CTLA-4 is a cytotoxic T-lymphocyte-associated granule serine protease that appears to be involved in T-cell activation. Amino acid sequences of representative human CTLA-4 polypeptides include for example, without limitation, GenBank numbers NM_005214, and NM_001037631. Binding of CTLA-4 to ligands B7-1 (CD80) and B7-2 (CD86) induces cell cycle arrest and diminished cytokine production. Transient blocking CTLA-4 activity with anti-CTLA-4 antibodies ("CTLA-4 blockade") enhances antigen specific T-cell responses with limited toxicity.

The anti-CTLA-4 antibody can be a monoclonal antibody, a chimeric antibody, a human antibody, a humanized antibody, a single-chain antibody, or an Fab fragment. Anti-CTLA-4 antibodies can be prepared as described above. Any CTLA-4 epitope can be used to generate the antibodies, provided that the resulting antibody binds to CTLA-4 in vivo in such a way that it blocks the binding of the CTLA-4 ligands, B7-1 and B7-2. Blocking antibodies can be identified based on their ability to compete with labeled ligands B7-1 and B7-2 for binding to CTLA-4 using standard screening methods.

Tumor Antigens

Also provided herein are compositions that include one or more tumor antigens that elicit an immune response against a tumor. Typically, such tumor antigens are used to treat cancer by stimulating the immune system to recognize and attack human cancer cells without harming normal cells. A tumor antigen is a molecule (e.g., a polypeptide, carbohydrate or lipid) that is expressed by a tumor cell and either (a) differs qualitatively from its counterpart expressed in normal cells, or (b) is expressed at a higher level in tumor cells than in normal cells. Thus, a tumor antigen can differ (e.g., by one or more amino acid residues where the molecule is a protein) from, or it can be identical to, its counterpart expressed in normal cells. It is preferably not expressed by normal cells. Alternatively, it is expressed at a level at least two-fold higher (e.g., a two-fold, three-fold, five-fold, ten-fold, 20-fold, 40-fold, 100-fold, 500-fold, 1,000-fold, 5,000-fold, or 15,000-fold higher) in a tumor cell than in the tumor cell's normal counterpart.

Tumor antigens can also include purified or partially purified proteins. Examples of tumor antigens include, without limitation, carcinoembryonic antigen (CEA), RAGE, MART (melanoma antigen), MAGE (melanoma antigen) 1-4, 6 and 12, MUC (mucin) (e.g., MUC-1, MUC-2, etc.), tyrosinase, Pmel 17 (gp100), GnT-V intron V sequence (N-acetylglucoaminyltransferase V intron V sequence), Prostate cancer psm, PRAME (melanoma antigen), β-catenin, MUM-1-B (melanoma ubiquitous mutated gene product), GAGE (melanoma antigen) 1, BAGE (melanoma antigen) 2-10, c-ERB2 (Her2/neu), EBNA (Epstein-Barr Virus nuclear antigen) 1-6, gp75, human papilloma virus (HPV) E6 and E7, p53, lung resistance protein (LRP) Bcl-2, prostate specific antigen (PSA), and Ki-67.

Tumor antigens can be intact tumor cells. The tumor cells are typically rendered proliferation incompetent by irradiation before being administered to the patient. Methods of irradiation are known to those in the art and can include exposure to γ-, x-, e-beam, and/or ultra-violet (wavelength of 10 nm to 320 nm, e.g., 50 nm to 320 nm, 100 nm to 320 nm, 150 nm to 320 nm, 180 nm to 320 nm, or 200 nm to 300 nm) radiation. Those of skill in the art will be able to identify a dose of radiation sufficient to render the cells replication incompetent, while still preserving the tumor cell structure.

The tumor cells can be the patient's own cells (autologous) tumor cells or allogeneic cancer cell lines. A useful method for eliciting an immune response against a tumor in a patient can include immunization with irradiated autologous GM-CSF-secreting tumor cells. In this method, a killed sample of the patient's own tumor cells that have been genetically engineered to express the immuno-stimulating cytokine, GM-CSF, is used to stimulate an immune response against a patient's tumor. Recombinant DNA encoding GM-CSF can be introduced into the tumor cells by standard methods, for example retroviral mediated or adenoviral mediated gene transfer. Methods for the production of irradiated autologous GM-CSF-secreting tumor cells and the use of irradiated autologous GM-CSF-secreting tumor cells to stimulate an immune response against cancer have been described in Soiffer R, Lynch T, Mihm M, Jung K, Rhuda C, Schmollinger J C, Hodi F S, Liebster L, Lam P, Mentzer S, Singer S, Tanabe K K, Cosimi A B, Duda R, Sober A, Bhan A, Daley J, Neuberg D, Parry G, Rokovich J, Richards L, Drayer J, Berns A, Clift S, Cohen L K, Mulligan R C, Dranoff G. "Vaccination with irradiated, autologous melanoma cells engineered to secrete human granulocyte-macrophage colony stimulating factor generates potent anti-tumor immunity in patients with metastatic melanoma". *Proc. Natl. Acad. Sci. USA* 1998; 95:13141-13146 and in Soiffer R J, Hodi F S, Haluska F, Jung K, Gillessen S, Singer S, Tanabe K, Duda R, Mentzer S, Jaklitsch M, Bueno R, Clift S, Hardy S, Neuberg D, Mulligan R C, Webb I, Mihm M, Dranoff G. "Vaccination with irradiated, autologous melanoma cells engineered to secrete granulocyte-macrophage colony stimulating factor by adenoviral mediated gene transfer augments anti-tumor immunity in patients with metastatic melanoma." *J. Clin. Oncol.* 2003; 21:3343-3350.

Alternatively or in addition, GM-CSF can be provided by the use of another GM-CSF expressing cell. The GM-CSF expressing cell can be another human cell type or line that has been stably transfected with nucleic acid encoding GM-CSF. One useful cell line is K562, a CML cell line that has low level of class I and class II expression that is not inducible with IFNγ and therefore is associated with a low likelihood of allogeneic response. K562 cells can be stably transfected with a plasmid encoding GM-CSF and a puromycin resistance gene. The cell line can be grown in suspension culture, and thus is amenable to large-scale manufacturing. GM-K562 cells can secrete relatively high levels of GM-CSF in vitro (9-13 μg of GM-CSF per $10^6$ cells over 24 hours, during the first 24 hours after thawing). Typically, 100% growth arrest occurs at radiation doses of 10,000 cGy, but GM-CSF secretion persists for at least 7 days.

In some embodiments, GM-GSF can be administered as a purified or partially purified polypeptide. The GM-CSF can be purified from natural sources or produced as a recombinant protein. GM-CSF is also available from commercial sources, including for example, OncoVEX GM-CSF (Biovex, Oxford, U.K.) Molgramostim (Leucomax, Schering & Plough, Madison, N.J., USA) and Sagramostim (Leukine®, Berlex Oncology).

Methods of Treating/Preventing Cancer

Provided herein are methods for treating and/or preventing cancer or symptoms of cancer in a subject comprising administering to the subject a therapeutically effective amount of one or more tumor cell antigens and an MFG-E8 inhibitor. The methods disclosed herein are generally useful for generating immune responses and as prophylactic vaccines or immune response-stimulating therapeutics. As used herein, "prophylaxis" can mean complete prevention of the symptoms of a disease, a delay in onset of the symptoms of a disease, or a lessening in the severity of subsequently developed disease symptoms. As used herein, "therapy" can mean a complete abolishment of the symptoms of a disease or a decrease in the severity of the symptoms of the disease. Type of cancer are well known to those in the art and can include, without limitation, cancers of the skin e.g., melanoma and basal cell carcinoma, lung, breast, kidney, ovarian, endometrial, prostate, gastric, colon, colorectal, kidney, bladder, pancreatic, testicular, stomach, esophageal, thyroid, bone, brain, neurologic, head and neck, germ cell or hematological cancer, e.g., leukemia and lymphoma, rhabdomyosarcoma (arising from muscle), retinoblastoma, osteosarcoma, Ewing's sarcoma, Wilms' tumor, and. In some embodiments the cancer is a cancer associated with over-expression of MFG-E8. In some embodiments, the cancer is melanoma, lung, breast, kidney, ovarian and colon carcinoma as well as certain leukemias. In some embodiments the subject has been diagnosed as having a cancer or as being predisposed to cancer.

Symptoms of cancer are well-known to those of skill in the art and include, without limitation, unusual mole features, a change in the appearance of a mole, including asymmetry, border, color and/or diameter, a newly pigmented skin area, an abnormal mole, darkened area under nail, breast lumps, nipple changes, breast cysts, breast pain, death, weight loss, weakness, excessive fatigue, difficulty eating, loss of appetite, chronic cough, worsening breathlessness, coughing up blood, blood in the urine, blood in stool, nausea, vomiting, liver metastases, lung metastases, bone metastases, abdominal fullness, bloating, fluid in peritoneal cavity, vaginal bleeding, constipation, abdominal distension, perforation of colon, acute peritonitis (infection, fever, pain), pain, vomiting blood, heavy sweating, fever, high blood pressure, anemia, diarrhea, jaundice, dizziness, chills, muscle spasms, colon metastases, lung metastases, bladder metastases, liver metastases, bone metastases, kidney metastases, and pancreatic metastases, difficulty swallowing, and the like.

The compositions can be administered directly to a subject. Generally, the one or more tumor cell antigens and an MFG-E8 inhibitor can be suspended in a pharmaceutically-acceptable carrier (e.g., physiological saline). A composition can be made by combining any of the MFG-E8-modulating compositions provided herein with a pharmaceutically acceptable carrier. Such carriers can include, without limitation, sterile aqueous or non-aqueous solutions, suspensions, and emulsions. Examples of non-aqueous solvents include mineral oil, propylene glycol, polyethylene glycol, vegetable oils, and injectable organic esters, for example. Aqueous carriers include, without limitation, water, alcohol, saline, and buffered solutions. Preservatives, flavorings, and other additives such as, for example, antimicrobials, antioxidants, chelating agents, inert gases, and the like also may be present. It will be appreciated that any material described herein that is to be administered to a mammal can contain one or more pharmaceutically acceptable carriers.

Any composition described herein can be administered to any part of the host's body. A composition can be delivered to, without limitation, the joints, nasal mucosa, blood, lungs, intestines, muscle tissues, skin, or peritoneal cavity of a mammal. In addition, a composition can be administered by intravenous, intraperitoneal, intramuscular, subcutaneous, intramuscular, intrarectal, intravaginal, intrathecal, intratracheal, intradermal, or transdermal injection, by oral or nasal administration, by inhalation, or by gradual perfusion over time. In a further example, an aerosol preparation of a composition can be given to a host by inhalation.

The dosage required depends on the route of administration, the nature of the formulation, the nature of the patient's illness, the subject's size, weight, surface area, age, and sex, other drugs being administered, and the judgment of the attending physician. Suitable dosages are in the range of 0.01-1,000 µg/kg. Wide variations in the needed dosage are to be expected in view of the variety of tumor cell antigens and an MFG-E8-modulating compositions available and the differing efficiencies of various routes of administration. Variations in these dosage levels can be adjusted using standard empirical routines for optimization as is well understood in the art. Administrations can be single or multiple (e.g., 2- or 3-, 4-, 6-, 8-, 10-, 20-, 50-, 100-, 150-, or more fold). Encapsulation of the composition in a suitable delivery vehicle (e.g., polymeric microparticles or implantable devices) may increase the efficiency of delivery.

The duration of treatment with any composition provided herein can be any length of time from as short as one day to as long as the life span of the host (e.g., many years). For example, tumor cell antigens and MFG-E8-modulating compositions can be administered once a month for three months or once a year for a period of ten years. It is also noted that the frequency of treatment can be variable. For example, tumor cell antigens and MFG-E8-modulating compositions can be administered once (or twice, three times, etc.) daily, weekly, monthly, or yearly. Tumor cell antigens and MFG-E8-modulating compositions can be administered together, i.e., at the same point in time or sequentially. For example, a patient can receive an irradiated autologous tumor cell, followed by a GM-CSF expressing cell, followed by a MFG-E8-modulating composition, separated by intervals of hours, days, months or years.

Alternatively or in addition the compositions can be administered along with an adjuvant. An "adjuvant" is an immunological compound that can enhance an immune response against a particular antigen such as a polypeptide. Examples of adjuvants include alum and other aluminum-based compounds (e.g., $Al_2O_3$). Aluminum-based compounds can be obtained from various commercial suppliers. Other adjuvants include immuno-stimulating complexes (ISCOMs) that can contain such components as cholesterol and saponins; one or more additional immunostimulatory components, including, without limitation, muramyldipeptide (e.g., N-acetylmuramyl-L-alanyl-D-isoglutamine; MDP), monophosphoryl-lipid A (MPL), and formyl-methionine containing tripeptides such as N-formyl-Met-Leu-Phe. Such compounds are commercially available from Sigma Chemical Co. (St. Louis, Mo.) and RIBI ImmunoChem Research, Inc. (Hamilton, Mont.), for example. Other adjuvants can include CpG oligodeoxynucleotides (Coley Pharmaceuticals), QS21 (Cambridge Biotech) and MF59 (Chiron). Adjuvants that enhance dendritic cell function can also be used; examples include GM-CSF, Flt3-ligand, and interferons.

The compositions provided herein can contain any ratio of adjuvant to antibody. The adjuvant:antibody ratio can be 50:50 (vol:vol), for example. Alternatively, the adjuvant:antibody ratio can be, without limitation, 90:10, 80:20, 70:30, 64:36, 60:40, 55:45, 40:60, 30:70, 20:80, or 90:10.

An effective amount of any composition provided herein can be administered to a host. The term "effective" as used herein refers to any amount that induces a desired immune response while not inducing significant toxicity in the host. Such an amount can be determined by assessing a host's immune response after administration of a known amount of a particular composition. In addition, the level of toxicity, if any, can be determined by assessing a host's clinical symptoms before and after administering a known amount of a particular composition. It is noted that the effective amount of a particular composition administered to a host can be adjusted according to a desired outcome as well as the host's response and level of toxicity. Significant toxicity can vary for each particular host and depends on multiple factors including, without limitation, the host's disease state, age, and tolerance to pain.

Antibodies can also be administered to a subject via in vivo therapeutic antibody gene transfer as discussed by Fang et al. (2005), Nat. Biotechnol. 23, 584-590. For example recombinant vectors can be generated to deliver a multicistronic expression cassette comprising a peptide that mediates enzyme independent, cotranslational self cleavage of polypeptides placed between MAb heavy and light chain encoding sequences. Expression leads to stoichiometric amounts of both MAb chains. In some embodiments the peptide that mediates enzyme independent, cotranslational self cleavage is the foot-and-mouth-disease derived 2A peptide.

Any method known in the art can be used to determine if a particular immune response is induced. Useful measures include tumor infiltration by CD4+ and CD8+ T lymphocytes, the presence of high titer antibodies against tumor antigens in post-immunization sera, and targeted destruction of tumor vasculature. In addition, clinical methods that can assess the degree of a particular disease state can be used to determine if a desired immune response is induced. For example, in a cancer patient, a reduction in tumor burden or a delay in the recurrence or metastasis can indicate a desired immune response in a patient treated with tumor cell antigens and MFG-E8-modulating compositions.

Methods to prophylactically treat a patient who is predisposed to develop cancer, a cancer metastasis or who has had a metastasis and is therefore susceptible to a relapse or recurrence are disclosed. The methods are particularly useful in high-risk individuals who, for example, have a family history of cancer or of metastasizing tumors, or show a genetic predisposition for a cancer metastasis. In some embodiments the tumors are MFG-E8-related tumors. Additionally, the methods are useful to prevent patients from having recurrences of MFG-E8-related tumors who have had MFG-E8-related tumors removed by surgical resection or treated with a conventional cancer treatment. Also provided are methods of inhibiting cancer progression and/or causing cancer regression comprising administering to the patient a therapeutically effective amount of tumor cell antigens and MFG-E8-modulating compositions.

In some embodiments, the patient in need of anti-cancer treatment can be treated with the tumor cell antigens and MFG-E8-modulating compositions described herein in conjunction with one or more antibodies directed at targets other than MFG-E8. Suitable targets can include cancer cell surface molecules, e.g., the EGF receptor, VEGF, HER-2, CD20, coMet, ErbB3, angiopoietins, and gangliosides such as GM2.

In some embodiments, the patient in need of anti-cancer treatment is treated with the tumor cell antigens and MFG-E8-modulating compositions described herein in conjunction with chemotherapy and/or radiation therapy. For example, following administration of the tumor cell antigens and MFG-E8-modulating compositions, the patient may also be treated with a therapeutically effective amount of anti-cancer radiation. In some embodiments chemotherapeutic treatment is provided in combination with tumor cell antigens and MFG-E8-modulating compositions. In some embodiments tumor cell antigens and MFG-E8-modulating compositions are administered in combination with chemotherapy and radiation therapy.

Methods of treatment comprise administering single or multiple doses of one or more tumor cell antigens and MFG-E8-modulating compositions to the patient. In some embodiments the tumor cell antigens and MFG-E8-modulating compositions are administered as injectable pharmaceutical compositions that are sterile, pyrogen free and comprise the tumor cell antigens and MFG-E8-modulating compositions in combination with a pharmaceutically acceptable carrier or diluent.

In some embodiments, the therapeutic regimens described herein are used with conventional treatment regimens for cancer including, without limitation, surgery, radiation therapy, hormone ablation and/or chemotherapy. Administration of the tumor cell antigens and MFG-E8-modulating compositions described herein may take place prior to, simultaneously with, or after conventional cancer treatment. In some embodiments, two or more different tumor cell antigens and MFG-E8-modulating compositions are administered to the patient.

Combination Therapy

In some embodiments compositions comprising two or more tumor cell antigens and MFG-E8-modulating compositions are provided. In some embodiments tumor cell antigens are autologous GM-CSF expressing tumor cells. The MFG-E8-modulating compositions can be mutant forms of MFG-E8 that lack or substantially lack the ability to bind $\alpha v \beta 3$ and $\alpha v \beta 5$ integrins. The MFG-E8-modulating compositions can also be anti-MFG-E8 antibodies and/or anti-PS antibodies. The compositions can further include a GM-CSF-expressing cell or cell line. Compositions comprising two or more MFG-E8-modulating compositions may be administered to persons or mammals suffering from, or predisposed to suffer from cancer. One or more antibodies may also be administered with another therapeutic agent, such as a cytotoxic agent, or cancer chemotherapeutic. Concurrent administration of two or more therapeutic agents does not require that the agents be administered at the same time or by the same route, as long as there is an overlap in the time period during which the agents are exerting their therapeutic effect. Simultaneous or sequential administration is contemplated, as is administration on different days or weeks.

In some embodiments the methods provided contemplate the administration of combinations, or "cocktails", of different antibodies. Such antibody cocktails may have certain advantages inasmuch as they contain antibodies which exploit different effector mechanisms or combine directly cytotoxic antibodies with antibodies that rely on immune effector functionality. Such antibodies in combination may exhibit synergistic therapeutic effects. Useful antibodies can include antibodies that target the EGF receptor, e.g., Cetuximab (Erbitux™), antibodies that target VEGF, e.g., Bevacizumab (Avastin™) and antibodies that target Her-2, e.g., trastuzimab (Herceptin™)

A cytotoxic agent refers to a substance that inhibits or prevents the function of cells and/or causes destruction of cells. The term is intended to include radioactive isotopes (e.g., $^{131}I$, $^{125}I$, $^{90}Y$ and $^{186}Re$), chemotherapeutic agents, and toxins such as enzymatically active toxins of bacterial, fungal, plant or animal origin or synthetic toxins, or fragments thereof. A non-cytotoxic agent refers to a substance that does not inhibit or prevent the function of cells and/or does not cause destruction of cells. A non-cytotoxic agent may include an agent that can be activated to be cytotoxic. A non-cytotoxic agent may include a bead, liposome, matrix or particle (see, e.g., U.S. Patent Publications 2003/0028071 and 2003/0032995 which are incorporated by reference herein). Such agents may be conjugated, coupled, linked or associated with an antibody disclosed herein.

In some embodiments, conventional cancer medicaments are administered with the compositions disclosed herein. Highly suitable agents include agents anti-angiogenic agents. Anti-angiogenic agents block the ability of tumors to stimulate new blood vessel growth necessary for their survival. Any anti-angiogenic agent known to those in the art can be used, including agents such as Bevacizumab (Avastin®, Genentech, Inc.) that block the function of vascular endothelial growth factor (VEGF). Other examples include, without limitation, Dalteparin (Fragmin®), Suramin ABT- 510, Combretastatin A4 Phosphate, Lenalidomide, LY317615 (Enzastaurin), Soy Isoflavone (Genistein; Soy Protein Isolate) AMG-706, Anti-VEGF antibody, AZD2171, Bay 43-9006 (Sorafenib tosylate), PI-88, PTK787/ZK 222584 (Vatalanib), SU11248 (Sunitinib malate), VEGF-Trap, XL184, ZD6474, Thalidomide, ATN-161, EMD 121974 (Cilenigtide) and Celecoxib (Celebrex®).

Other useful agents include those agents that promote DNA-damage, e.g., double stranded breaks in cellular DNA, in cancer cells. Any form of DNA-damaging agent know to those of skill in the art can be used. DNA damage can typically be produced by radiation therapy and/or chemotherapy. Examples of radiation therapy include, without limitation, external radiation therapy and internal radiation therapy (also called brachytherapy). Energy sources for external radiation therapy include x-rays, gamma rays and particle beams; energy sources used in internal radiation include radioactive iodine (iodine$^{125}$ or iodine$^{131}$), and from strontium$^{89}$, or radioisotopes of phosphorous, palladium, cesium, iridium, phosphate, or cobalt. Methods of administering radiation therapy are well know to those of skill in the art.

Examples of DNA-damaging chemotherapeutic agents include, without limitation, Busulfan (Myleran), Carboplatin (Paraplatin), Carmustine (BCNU), Chlorambucil (Leukeran), Cisplatin (Platinol), Cyclophosphamide (Cytoxan, Neosar), Dacarbazine (DTIC-Dome), Ifosfamide (Ifex), Lomustine (CCNU), Mechlorethamine (nitrogen mustard, Mustargen), Melphalan (Alkeran), and Procarbazine (Matulane)

Other cancer chemotherapeutic agents include, without limitation, alkylating agents, such as carboplatin and cisplatin; nitrogen mustard alkylating agents; nitrosourea alkylating agents, such as carmustine (BCNU); antimetabolites, such as methotrexate; folinic acid; purine analog antimetabolites, mercaptopurine; pyrimidine analog antimetabolites, such as fluorouracil (5-FU) and gemcitabine (Gemzar®); hormonal antineoplastics, such as goserelin, leuprolide, and tamoxifen; natural antineoplastics, such as aldesleukin, interleukin-2, docetaxel, etoposide (VP-16), interferon alfa, paclitaxel (Taxol®), and tretinoin (ATRA); antibiotic natural antineoplastics, such as bleomycin, dactinomycin, daunorubicin, doxorubicin, daunomycin and mitomycins including mitomycin C; and vinca alkaloid natural antineoplastics, such as vinblastine, vincristine, vindesine; hydroxyurea; aceglatone, adriamycin, ifosfamide, enocitabine, epitiostanol, aclarubicin, ancitabine, nimustine, procarbazine hydrochloride, carboquone, carboplatin, carmofur, chromomycin A3, antitumor polysaccharides, antitumor platelet factors, cyclophosphamide (Cytoxin®), Schizophyllan, cytarabine (cytosine arabinoside), dacarbazine, thioinosine, thiotepa, tegafur, dolastatins, dolastatin analogs such as auristatin, CPT-11 (irinotecan), mitozantrone, vinorelbine, teniposide, aminopterin, carminomycin, esperamicins (See, e.g., U.S. Pat. No. 4,675,187), neocarzinostatin, OK-432, bleomycin, furtulon, broxuridine, busulfan, honvan, peplomycin, bestatin (Ubenimex®), interferon-β, mepitiostane, mitobronitol, melphalan, laminin peptides, lentinan, Coriolus versicolor extract, tegafur/uracil, estramustine (estrogen/mechlorethamine).

Additional agents which may be used as therapy for cancer patients include EPO, G-CSF, ganciclovir; antibiotics, leuprolide; meperidine; zidovudine (AZT); interleukins 1 through 18, including mutants and analogues; interferons or cytokines, such as interferons α, β, and γ hormones, such as luteinizing hormone releasing hormone (LHRH) and analogues and, gonadotropin releasing hormone (GnRH); growth factors, such as transforming growth factor-β (TGF-β), fibroblast growth factor (FGF), nerve growth factor (NGF), growth hormone releasing factor (GHRF), epidermal growth factor (EGF), fibroblast growth factor homologous factor (FGFHF), hepatocyte growth factor (HGF), and insulin growth factor (IGF); tumor necrosis factor-α & β (TNF-α & β); invasion inhibiting factor-2 (IIF-2); bone morphogenetic proteins 1-7 (BMP 1-7); somatostatin; thymosin-α-1; γ-globulin; superoxide dismutase (SOD); complement factors; and anti-angiogenesis factors.

Prodrug refers to a precursor or derivative form of a pharmaceutically active substance that is less cytotoxic or non-cytotoxic to tumor cells compared to the parent drug and is capable of being enzymatically activated or converted into an active or the more active parent form. See, e.g., Wilman, "Prodrugs in Cancer Chemotherapy" Biochemical Society Transactions, 14, pp. 375-382, 615th Meeting Belfast (1986) and Stella et al., "Prodrugs: A Chemical Approach to Targeted Drug Delivery," Directed Drug Delivery, Borchardt et al., (ed.), pp. 247-267, Humana Press (1985). Prodrugs include, but are not limited to, phosphate-containing prodrugs, thiophosphate-containing prodrugs, sulfate-containing prodrugs, peptide-containing prodrugs, D-amino acid-modified prodrugs, glycosylated prodrugs, b-lactam-containing prodrugs, optionally substituted phenoxyacetamide-containing prodrugs or optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use herein include, but are not limited to, those chemotherapeutic agents described above.

EXAMPLES

Example 1

Materials and Methods

Mice.

GM-CSF-, GM-CSF/IL-3-, IFN-γ- (Dalton et al., 1993), and GM-CSF/IL-3/IFN-γ-deficient mice were backcrossed at least nine generations onto the C57Bl/6 strain and housed under specific pathogen-free conditions. Genotypes were confirmed by PCR (Enzler et al., 2003), and the experiments were conducted under a protocol approved by the AAALAC-accredited Dana-Farber Cancer Institute IACUC.

Phagocytosis Assays

Apoptotic cells were generated by exposing thymocytes to 10 μM dexamethasone at 37° for 6 hours, splenocytes to 40 Gy γ-irradiation, and Jurkat T cells to 5 mg/ml etoposide (Sigma-Aldrich) at 37° for 16 hours. Necrotic cells were induced by five cycles of freeze-thaw or culture in 20% ethanol for 60 minutes. The percentage of apoptotic and necrotic cells was quantified with annexin-V and propidium iodide staining, according to the manufacturer's instructions (Sigma-Aldrich). Apoptotic or necrotic cells were labeled with 5- (and 6-) carboxytetramethylrhodamine, succinimidyl ester (5[6]-TAMRA, SE, Molecular Probes) or carboxyfluorescein diacetate succinimidyl ester (CFSE, Molecular Probes) at 37° for 15 mins.

Macrophages were recovered by lavage from the peritoneal cavity 48 hours after thioglycollate instillation (2 mg/ml: Sigma-Aldrich) or with CD11b microbeads (Miltenyi Biotech) from the spleen, liver, and bronchoalveolar lavage, and cultured with RPMI 1640 supplemented with 10% heat inactivated fetal calf serum, L-glutamine, and penicillin/streptomycin. Dendritic cells were isolated from spleens using CD11c microbeads (Miltenyi Biotech) or generated from bone marrow cells ($2 \times 10^6$/well) by culture for seven days using conditioned media (days 0, 2, 4) from B16 cells secreting GM-CSF or Flt3-L (Mach et al., 2000). Macrophages or dendritic cells ($1 \times 10^5$) were exposed for two hours to labeled apoptotic or necrotic cells ($1 \times 10^6$), washed, stained with mAbs to CD11b or CD11c (BD Pharmingen), and evaluated for phagocytosis efficiency by flow cytometry.

Cytokine Assays

TGF-β, IL-6, IL-1, IL-12p70, IL-23p19, IL-10, and TNF-α were measured in culture supernatants with an ELISA, according to the manufacturer's directions (Pierce-Endogen, R&D Systems, eBioscience). For intra-cellular cytokine staining, T cells were stimulated with 1 mg/ml PMA and 50 ng/ml ionomycin for four hours and GolgiPlug (BD-Pharmingen) added for 2 hours at 37°. The cells were stained with anti-CD3, CD4, or CD8 mAbs, fixed and permeabilized with Cytofix/Cytoperm (BD-Pharmingen), stained again with anti-IFN-γ, anti-IL-17 and isotype control mAbs (BD Pharmingen), and analyzed by flow cytometry.

Cell Proliferation Assays

Peritoneal macrophages were exposed to apoptotic or necrotic cells for 2 hours, washed, co-cultured in 96 well flat-bottomed wells with Balb/c splenocytes for 72 hours, and $^3$H thymidine uptake determined. For suppression assays, $CD4^+CD25^+$ T cells were obtained using a regulatory T cell isolation kit (Miltenyi Biotech), according to the manufacturer's protocol. The ability of Tregs to inhibit $CD4^+CD25^-$ effector T cell proliferation and IL-2 production was evaluated using standard procedures.

Chemotaxis Assays

Supernatants of macrophages exposed to apoptotic cells were diluted 1:10 in culture media and added to the bottom wells of a microchamber containing an 8 μm pore polycarbonate filter (Coster-Corning). $CD4^+CD25^+$ or $CD4^+CD25^-$ T cells ($1 \times 10^4$ cells/well) were applied to the upper chamber in the presence or absence of anti-human CCL22/MDC neutralizing Ab or isotype control (R&D systems). After incubation at 37° for two hours, the cells migrating to the bottom chamber were collected and counted.

Flow Cytometry

Macrophages were pretreated with 1 ml/ml GolgiPlug (BD-Pharmingen) for 4 hr at 37°, stained with anti-CD11b mAb (BD-Pharmingen), fixed and permeabilized with Cytofix/Cytoperm buffer (BD-Pharmingen), and stained again with unconjugated MFG-E8 mAb (Alexia) or Gas6 mAb (R&D Systems) followed by PE-labeled goat anti-IgG2 Ab (BD-Pharmingen). For FoxP3 staining, lymphoid cells were labeled with anti-CD3 and CD4 mAbs (BD Pharmingen), washed, and then stained with PE-labeled anti-FoxP3 Ab using the FoxP3 staining set according to the manufacturer's protocol (eBioscience). Cell acquisition was performed with a FW501 flow cytometer (Beckman-Coulter) and analyzed by FlowJo software (Tree Star).

Retroviral Mediated Gene Transfer

Full-length sequences encoding the open reading frames of MFG-E8 or the RGE mutant (mutant MFG-E8 in which the RGD sequence in the second EGF domain is replaced with RGE) were introduced into the pMFG retroviral vector, and high titer VSV-G pseudotyped replication defective viral stocks prepared with 293-GPG cells, as previously described (Mach et al., 2000). Replicating peritoneal macrophages were transduced in the presence of 10 ng/ml M-CSF (R&D Systems).

After 48 hours of pre-conditioning with 5-FU (150 mg/kg), bone marrow cells were isolated from 8-10 week old wild type and GM-CSF/IL-3/IFN-γ deficient mice and cultured overnight with X-VIVO (Cambrex) supplemented with stem cell factor (100 ng/ml) and thrombopoietin (50 ng/ml). The cells were transduced with retroviral supernatants for 48 hours and then $1 \times 10^6$ cells were injected into lethally irradiated recipients (two doses of 560 rads, 6 hours apart, using a $^{137}$Cs source). Eight weeks after transplant, mice were sacrificed and analyzed for MFG-E8 expression, phagocytic capacity, and $CD4^+$ T cell subsets as above.

B16 Melanoma Experiments

For tumor prevention studies, 8-12 week old female C57Bl/6 mice were injected subcutaneously in the flank with $1 \times 10^6$ irradiated (150 Gy) wild type or retrovirally transduced (GM-CSF, MFG-E8, and/or RGE) B16 cells and seven days later challenged subcutaneously on the back with $1 \times 10^6$ live B16 cells. For the therapy model, mice were injected on day 0 or 3 with $5 \times 10^5$ live B16 cells and treated on days 0, 7, and 14 with $1 \times 10^6$ irradiated, engineered B16 cells. Tumor growth was monitored and the product of tumor diameters was recorded.

Tumor infiltrating lymphocytes were obtained from B16 challenge sites using a Nocoprep (Axis-Shield) cell gradient separation followed by $CD3^+$ T cell purification with anti-CD3 labeled magnetic beads (Miltenyi). The cells were analyzed by flow cytometry using mAbs against CD4, CD8, CD69, and FoxP3. Antigen specific $CD8^+$ responses against $H-2^6$ restricted peptides (DFCI Molecular Biology Core) derived from TRP-2 (180-188: SVYDFFVWL) or E1A (234-243: SGPSNTPPEI) were determined by incubating lymphocytes for 72 hours with $1 \times 10^5$ B16 cells and 25 U/ml IL-2 and measuring IFN-γ production by ELISPOT using peptide pulsed splenocytes as targets.

Example 2

GM-CSF Regulates the Phagocytosis of Apoptotic Cells

Labeled cells were rendered apoptotic with dexamethasone or etoposide or necrotic by freeze-thaw were added to $CD11b^+$ wild type or GM-CSF deficient peritoneal macrophages and the efficiency of ingestion measured by flow cytometry. Impaired uptake by GM-CSF deficient peritoneal macrophages was observed in with the case of etoposide treated Jurkat T cells and gamma-irradiated splenocytes, whereas the uptake of cells rendered necrotic by repeated freeze-thaw cycles or 20% ethanol treatment was intact (FIG. 1A and not shown). GM-CSF/IL-3 and GM-CSF/IL-3/IFN-γ deficient macrophages displayed comparable phagocytosis profiles, revealing a selective requirement for GM-CSF in the uptake of apoptotic cells (not shown). CD11C expressing dendritic cells purified from the spleens of GM-CSF deficient mice manifested a similar impairment, although dendritic cells generated by culture of bone marrow precursors with Flt3-ligand (Flt3-L) exhibited efficient ingestion of apoptotic material (FIG. 1B). These latter results are in accord with a recent report indicating that Flt3-L stimulated dendritic cells employ a nibbling process to ingest dying cells, in contrast to the engulfment triggered with GM-CSF (Janssen et al., 2006). However, our findings suggest that, under steady-state conditions, GM-CSF may be a more important signal than Flt3-L for regulating dendritic cell phagocytosis of apoptotic cells.

Consistent with previous studies, wild type macrophages induced substantial amounts of TGF-β but minimal IL-1, IL-6, IL-12p70, and IL-23p19 in response to apoptotic cells (Fadok et al., 1998; Huynh et al., 2002; Kim et al., 2004; Stark et al., 2005), whereas necrotic cells induced the opposite profile (FIG. 1C). In contrast, GM-CSF (not shown), GM-CSF/IL-3, and GM-CSF/IL-3/IFN-γ deficient macrophages produced significantly less TGF-β, but more IL-1, IL-6, IL-12p70, and IL-23p19 following exposure to either apoptotic or necrotic cells. GM-CSF/IL-3 deficient macrophages generated the highest levels of IL-12p70, whereas GM-CSF/IL-3/IFN-γ deficient macrophages generated the highest levels of IL-23p19, suggesting that IFN-γ also contributes to cytokine regulation. Little differences were observed for IL-10 or TNF-α production across the set of mice (not shown).

To examine the functional relevance of the impaired phagocytosis of apoptotic cells, we performed mixed leukocyte reactions with peritoneal macrophages from cytokine deficient mice and splenocytes from wild type allogeneic Balb/c mice (FIG. 1D). Whereas both wild type and GM-CSF/IL-3/IFN-γ deficient phagocytes loaded with necrotic cells stimulated robust allogeneic T cell responses, the ingestion of apoptotic cells by wild type macrophages suppressed proliferative responses more efficiently than GM-CSF/IL-3/IFN-γ deficient macrophages.

Example 3

GM-CSF Regulates MFG-E8 Expression

Figure 2:
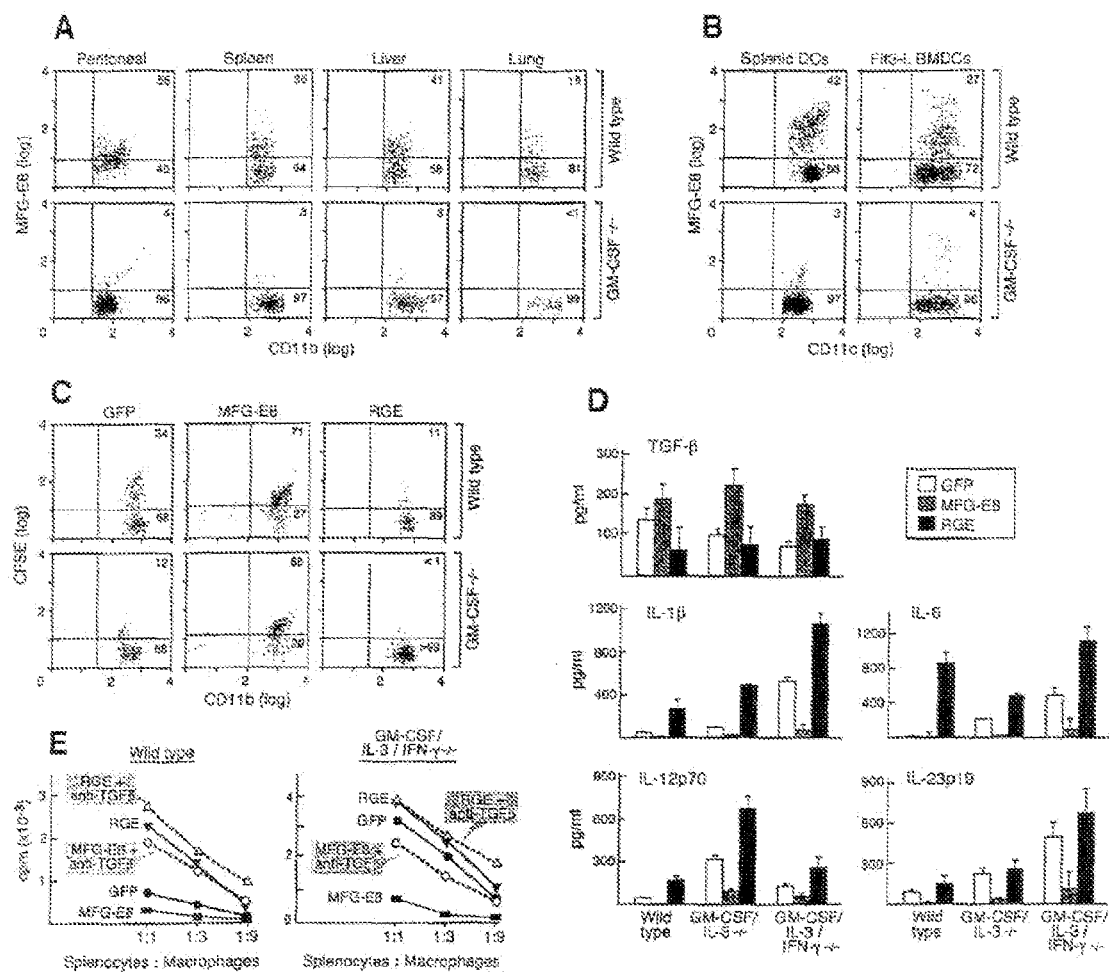
FIG. 2 depicts the results of an experiment demonstrating that GM-CSF regulates MFG-E8 mediated uptake of apoptotic cells. (A) Wild type or GM-CSF deficient macrophages were isolated from the peritoneal cavity, liver, spleen, and bronchoalveolar lavage, exposed to apoptotic cells overnight and MFG-E8 expression determined by flow cytometry. (B) Wild type or GM-CSF deficient splenic or Flt3-L generated bone marrow derived dendritic cells were exposed to apoptotic cells overnight and stained for MFG-E8. (C) Wild type or GM-CSF deficient peritoneal macrophages were transduced with retroviral vectors encoding MFG-E8, the RGE mutant, or GFP and evaluated for the phagocytosis of labeled apoptotic thymocytes. (D) Wild type, GM-CSF/IL-3, or GM-CSF/IL-3/IFN-$\gamma$ deficient peritoneal macrophages engineered to express MFG-E8, the RGE mutant, or GFP (four mice per group) were exposed to apoptotic thymocytes and culture supernatants analyzed for cytokine production by ELISA. (E) Wild type or GM-CSF/IL-3/IFN-$\gamma$ deficient peritoneal macrophages engineered to express MFG-E8, the RGE mutant or GFP were exposed to apoptotic thymocytes for two hours and then co-cultured for 72 hours with wild type Balb/c splenocytes, with or without neutralizing antibodies to TGF-β. Proliferation was determined by $^3$H-thymidine uptake. Results are representative of two to four independent experiments.
Figure 8:
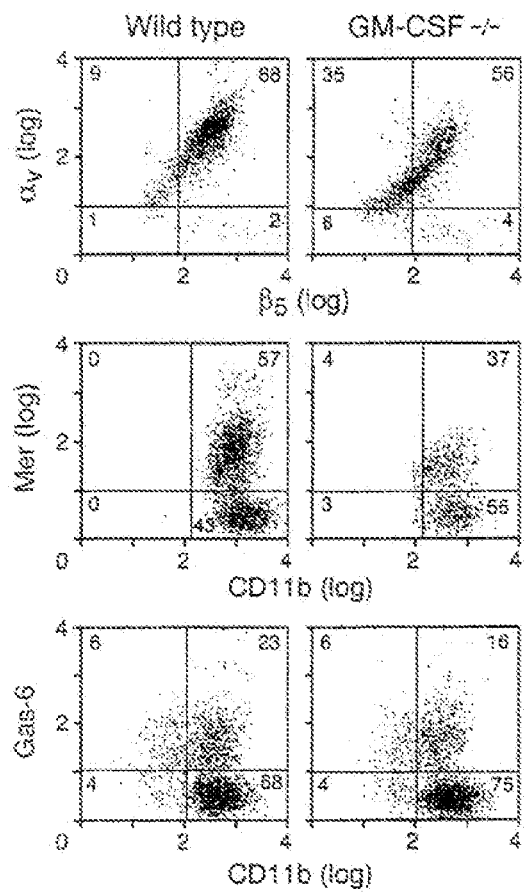
FIG. 8 depicts the results of an experiment demonstrating that GM-CSF deficient macrophages show reduced expression of multiple gene products involved in phosphatidylserine-mediated uptake of apoptotic cells. Wild type or GM-CSF deficient peritoneal macrophages were exposed to apoptotic cells and then assayed for $\alpha_v\beta_5$, Mer, and Gas-6 expression. Similar results were found in two experiments.

Real-time PCR analysis of GM-CSF deficient peritoneal macrophages disclosed minimal or no changes in the levels of MARCO, CD36, scavenger receptor-A, and the putative phosphatidylserine receptor, MFG-E8 transcripts were significantly reduced compared to wild type cells (not shown). Flow cytometry confirmed the marked decrease in MFG-E8 expression in macrophages isolated from the peritoneal cavity, spleen, liver, and lung of GM-CSF deficient mice (FIG. 2A). Splenic dendritic cells and Flt3-L generated bone marrow derived dendritic cells showed similar reductions in MFG-E8, underscoring the importance of endogenous GM-CSF for expression of this opsonin (FIG. 2B). Moreover, the efficient ingestion of apoptotic cells by Flt3-ligand induced dendritic cells (FIG. 1B) in the absence of MFG-E8 suggests that these cells may use multiple receptors for corpse clearance. Comparable decreases in MFG-E8 expression were observed with antigen presenting cells from GM-CSF/IL-3 and GM-CSF/IL-3/IFN-γ deficient mice (not shown). Since MFG-E8-mediated uptake of dying cells involves $\alpha_v\beta_3$ and $\alpha_v\beta_5$ integrins and intersects with the Gas-6/Mer pathway (Hanayama et al., 2002; Wu et al., 2005), we also assayed the expression of these molecules on GM-CSF deficient macrophages. Modest reductions were observed by flow cytometry (FIG. 8), suggesting that GM-CSF broadly regulates phosphatidylserine-based uptake of apoptotic cells.

To delineate the contribution of MFG-E8 deficiency to the impaired phagocytosis of apoptotic cells by GM-CSF deficient macrophages, we reconstituted MFG-E8 expression in vitro through retroviral transduction of replicating peritoneal macrophages, using M-CSF as a mitogen. For these experiments, we also generated a high titer virus encoding a previously described MFG-E8 mutant, in which the RGD sequence involved in integrin binding was modified to RGE (Asano et al., 2004). As this protein retains the capacity to bind phosphatidylserine on apoptotic cells, but cannot be internalized into phagocytes, this construct functions as a dominant negative inhibitor. Flow cytometry documented that transduced GM-CSF, GM-CSF/IL-3, and GM-CSF/IL-3/IFN-γ deficient macrophages achieved MFG-E8 levels comparable to wild type macrophages (not shown). MFG-E8 restoration increased the phagocytosis of apoptotic cells in GM-CSF deficient cells to wild type levels, whereas MFG-E8 over-expression in wild type cells further augmented corpse ingestion (FIG. 2C). MFG-E8 levels did not impact the uptake of necrotic cells (not shown). In contrast, the RGE mutant decreased apoptotic cell ingestion in wild type and cytokine deficient macrophages.

Modulation of the MFG-E8 pathway resulted in significant changes in cytokine production and immunogenicity. Enforced MFG-E8 expression in GM-CSF/IL-3/IFN-γ deficient macrophages restored TGF-β secretion and reduced IL-1, IL-6, IL-12p70, and IL-23p19 production to levels comparable to wild type controls (FIG. 2D). Conversely, the RGE mutant decreased TGF-β secretion and increased IL-1, IL-6, IL-12p70, and IL-23p19 production in wild type macrophages. Moreover, the RGE mutant abrogated the inhibitory effects of apoptotic cells on the allo-stimulatory activity of wild type peritoneal macrophages (FIG. 2E). Conversely, MFG-E8 transduction normalized the aberrant allo-stimulatory activity of GM-CSF/IL-3/IFN-γ deficient macrophages exposed to apoptotic cells. This suppression required TGF-β, as the addition of anti-TGF-β neutralizing antibodies antagonized the effects of MFG-E8 transduction, but did not those of the RGE mutant.

Example 4

Figure 3:
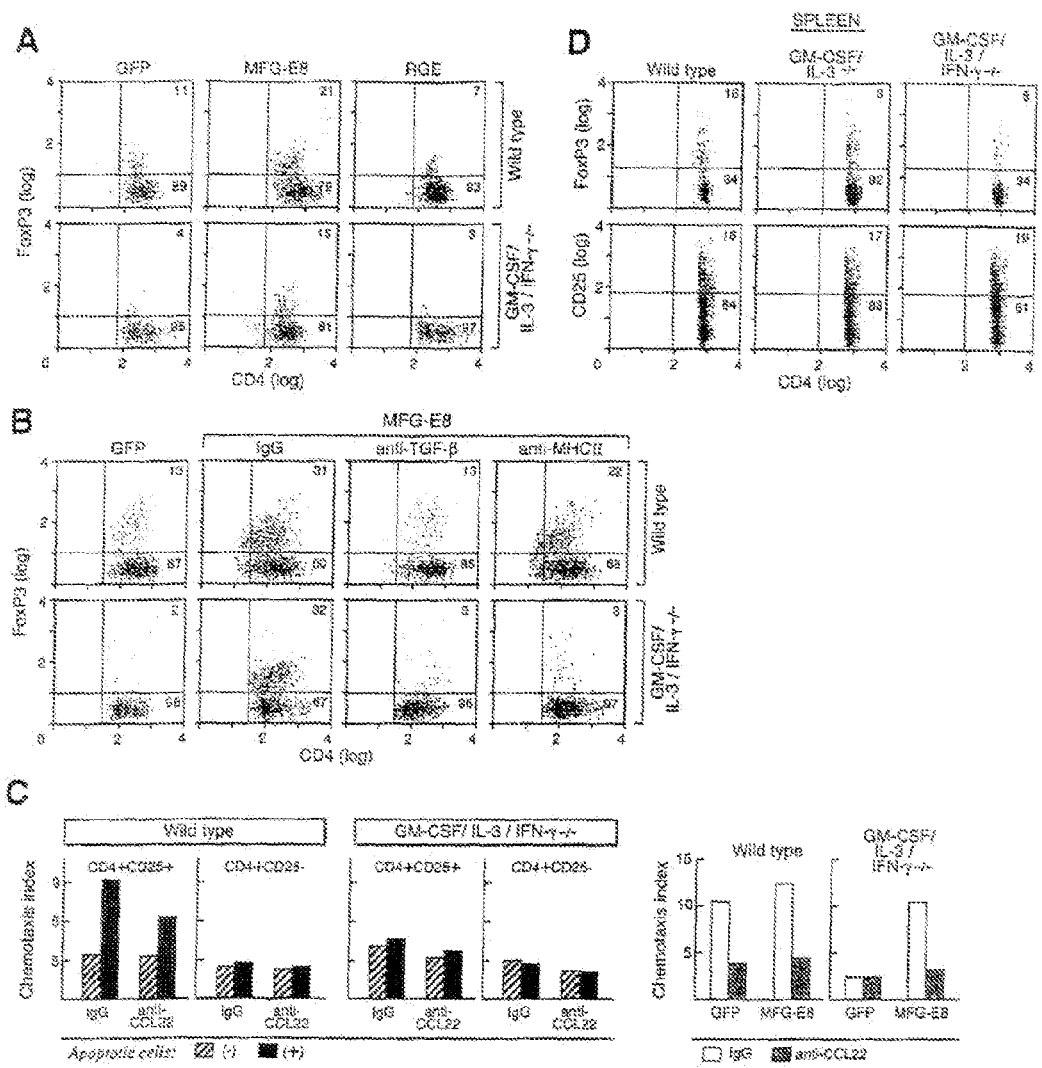
FIG. 3 depicts the results of an experiment demonstrating GM-CSF contributes to Treg homeostasis through MFG-E8. (A) Wild type or GM-CSF/IL-3/IFN-γ deficient peritoneal macrophages engineered to express MFG-E8, the RGE mutant or GFP were exposed to apoptotic thymocytes for two hours and then co-cultured for 72 hours with wild type syngeneic splenocytes. FoxP3 expressing Tregs were assayed by flow cytometry. (B) Blocking antibodies to TGF-β and MHC class II or control isotype were added to the co-culture of apoptotic cell-loaded macrophages and syngeneic splenocytes. (C) Culture supernatants from macrophages exposed to apoptotic cells were assayed for chemotactic activity against CD4$^+$25$^+$ and CD4$^+$CD25$^-$ T cells. Blocking antibodies against CCL22 or control isotype were added as indicated. (D) Splenocytes from wild type, GM-CSF/IL-3, or GM-CSF/IL-3/IFN-γ deficient mice were analyzed for CD4, CD25 and FoxP3 expression. Results are representative of two to five experiments.

GM-CSF is Required for Treg Homeostasis Through MFG-E8-Mediated Uptake of Apoptotic Cells To explore whether MFG-E8-mediated uptake of dying cells might contribute to Treg homeostasis under physiologic conditions, we first co-cultured syngeneic wild type CD4$^+$ T cells with apoptotic cell loaded peritoneal macrophages and then analyzed FoxP3 expression (FIG. 3A). Whereas wild type cells efficiently stimulated Tregs, GM-CSF/IL-3/IFN-γ macrophages were impaired. MFG-E8 transduction of both wild type and cytokine deficient macrophages resulted in increased FoxP3$^+$ cells, whereas the RGE mutant decreased Treg induction. Antibody blocking experiments established that MFG-E8-mediated expansion of Tregs required TGF-β and MHC class II (FIG. 3B). The FoxP3$^+$ cells proliferated during the co-culture and manifested typical suppressor activity in allogeneic mixed leukocyte reactions (not shown). Moreover, supernatants from apoptotic cell loaded wild type, but not GM-CSF/IL-3/IFN-γ deficient macrophages provoked selective migration of CD4$^+$CD25$^+$ T cells in a CCL22 dependent fashion (FIG. 3C). Reconstitution of MFG-E8 expression in GM-CSF/IL-3/IFN-γ deficient macrophages restored CCL22 dependent CD4$^+$CD25$^+$ T cell chemotaxis (Curiel et al., 2004).

Figure 9:
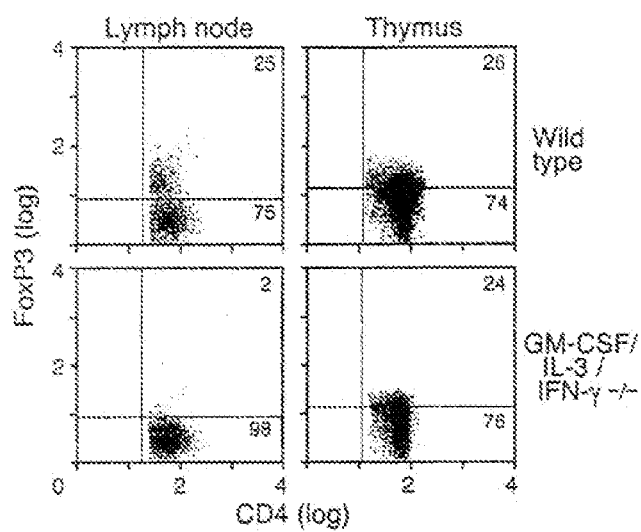
FIG. 9 depicts the results of an experiment demonstrating that GM-CSF regulates peripheral homeostasis of Tregs. Wild type or GM-CSF deficient lymph nodes and thymi were analyzed for FoxP3 expressing CD4$^+$ T cells. Gates CD3$^+$ T cells are shown. Similar results were obtained in two experiments.
Figure 10:
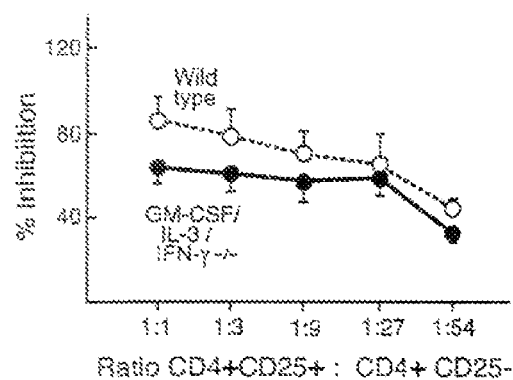
FIG. 10 depicts the results of an experiment demonstrating that GM-CSF deficient CD4$^+$CD25$^+$ cells show reduced suppressor activity. CD4$^+$CD25$^+$ T cells were purified from the spleens of wild type and GM-CSF/IL-3/IFN-γ deficient mice and assayed for suppression of anti-CD3 stimulated CD4$^+$CD25$^-$ T cell proliferation. Similar results were obtained in three experiments.

To determine whether the impaired induction of Tregs in vitro was indicative of altered Treg homeostasis in vivo, we quantified FoxP3$^+$ cells in the mutant mice. While no differences in the numbers of splenic CD4$^+$CD25$^+$ T cells were observed, the frequency of CD3$^+$CD4$^+$FoxP3$^+$ T cells in GM-CSF (not shown), GM-CSF/IL-3 and GM-CSF/IL-3/IFN-γ deficient mice were significantly decreased compared to wild type controls (FIG. 3D). The absolute numbers of FoxP3$^+$ cells were $3.5\pm1.8\times10^5$ cells/spleen for 5 wild type, $0.7\pm0.1\times10^5$ cells/spleen for 5 GM-CSF/IL-3 deficient, and $0.7\pm0.4\times10^5$ cells/spleen for 5 GM-CSF/IL-3/IFN-γ deficient mice (either knockout strain versus wild type, p=0.007). Similar reductions in Tregs were observed in lymph nodes, but not thymi of the mutant mice (FIG. 9), suggesting that peripheral maintenance rather than production might be the primary defect. CD4+CD25+ T cells from GM-CSF/IL-3/IFN-γ deficient mice showed weaker suppressor activity compared to CD4+CD25+ cells from wild type mice in standard in vitro assays (FIG. 10), although additional studies using purified FoxP3+ cells are required to evaluate regulatory function on an individual cell basis.

Example 5

GM-CSF Regulates CD4+ Effector T Cell Subsets Through MFG-E8

Figure 4:
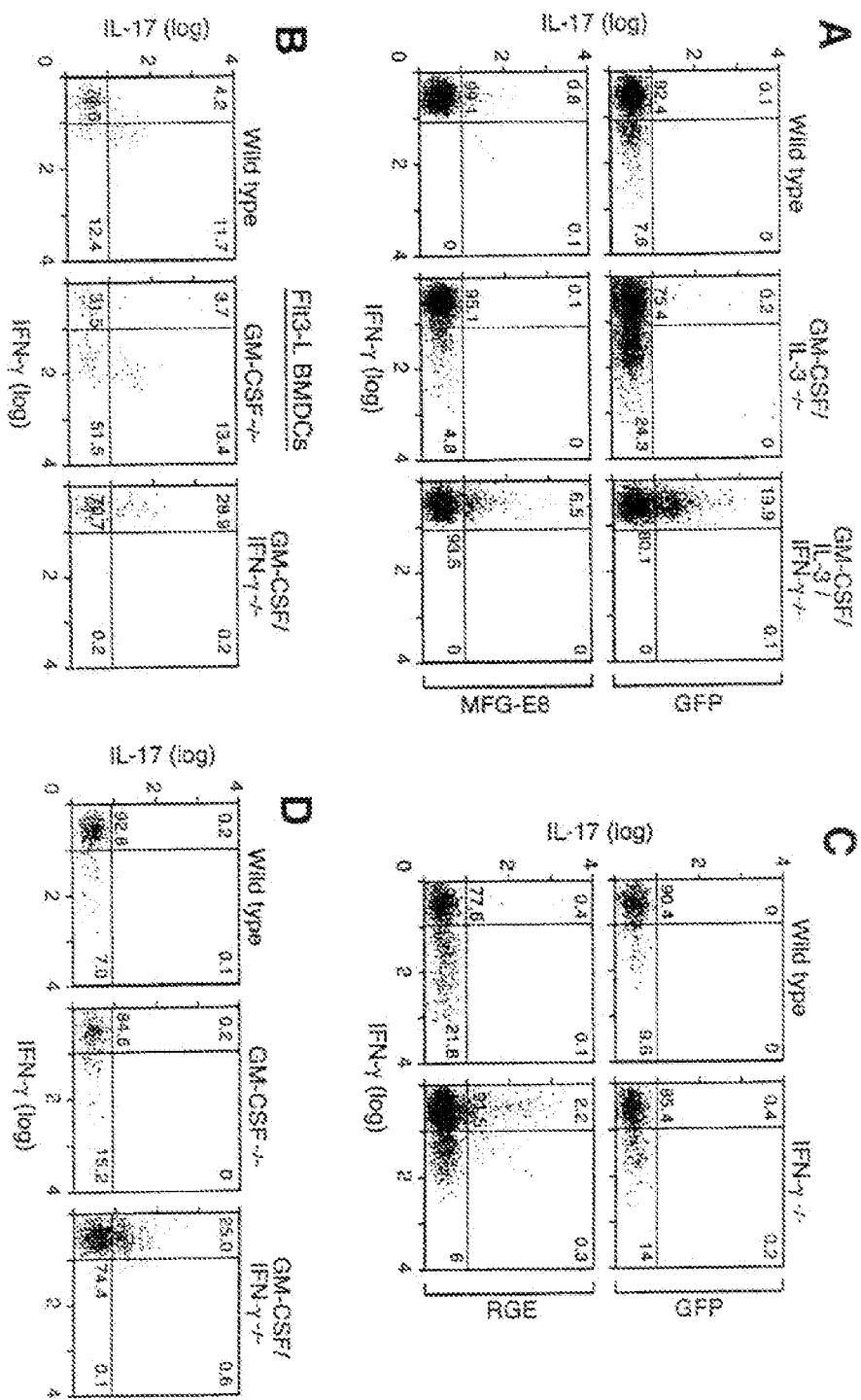
FIG. 4 depicts the results of an experiment demonstrating that GM-CSF regulates CD4$^+$ effector T cells through MFG-E8. (A) Wild type, GM-CSF/IL-3, or GM-CSF/IL-3/IFN-γ deficient peritoneal macrophages were exposed to apoptotic thymocytes for two hours and co-cultured for 72 hours with syngeneic wild type CD3$^+$CD45RA$^+$CD62$^{hi}$ naïve T cells. T cells were then analyzed for IL-17 and IFN-γ production. (B) Wild type, GM-CSF or GM-CSF/IFN-γ deficient Flt3-L generated bone marrow derived dendritic cells were exposed to apoptotic thymocytes for two hours and used to stimulate syngeneic wild type naïve T cells. (C) Wild type or IFN-γ deficient macrophages engineered to express the RGE mutant or GFP were exposed to apoptotic thymocytes for two hours, and used to stimulate syngeneic wild type naïve T cells. (D). Splenocytes from wild type, GM-CSF or GM-CSF/IFN-γ deficient mice were stimulated with PMA and ionomycin. Cytokine production for CD3$^+$CD4$^+$ gated cells is shown. Similar results were obtained in two experiments.

The increased production of inflammatory cytokines by apoptotic cell loaded GM-CSF deficient antigen presenting cells raised the possibility that CD4+ effector T cell subsets might be altered. To investigate this issue, we co-cultured syngeneic wild type CD3+CD45RA+CD62$^{hi}$ naïve T cells with apoptotic cell loaded peritoneal macrophages and then analyzed IL-17 and IFN-γ expression by flow cytometry (FIG. 4A). Consistent with the augmented IL-12 p70 secretion, GM-CSF/IL-3 deficient macrophages stimulated increased Th1 cells. The combination of augmented IL-23, IL-1, and IL-6 levels in GM-CSF/IL-3/IFN-γ deficient macrophages yielded increased Th17 cells. MFG-E8 transduction of cytokine deficient macrophages suppressed CD4+ effector cell development. Comparable findings were obtained using Flt3-L generated bone marrow derived dendritic cells (FIG. 4B). In accordance with these results, expression of the RGE mutant in wild type macrophages promoted Th1 cells, whereas transduction of IFN-γ deficient macrophages with the RGE mutant triggered Th17 cells (FIG. 4C). To determine whether similar CD4+ T cell subsets were generated in vivo, freshly isolated splenocytes were stimulated with PMA and ionomycin (FIG. 4D). Th1 skewing was evident in GM-CSF deficient mice, while Th17 cells were prominent in GM-CSF/IFN-γ deficient mice.

Example 6

MFG-E8 Reconstitution Normalizes CD4+ Subsets in GM-CSF Deficient Mice

Figure 5:
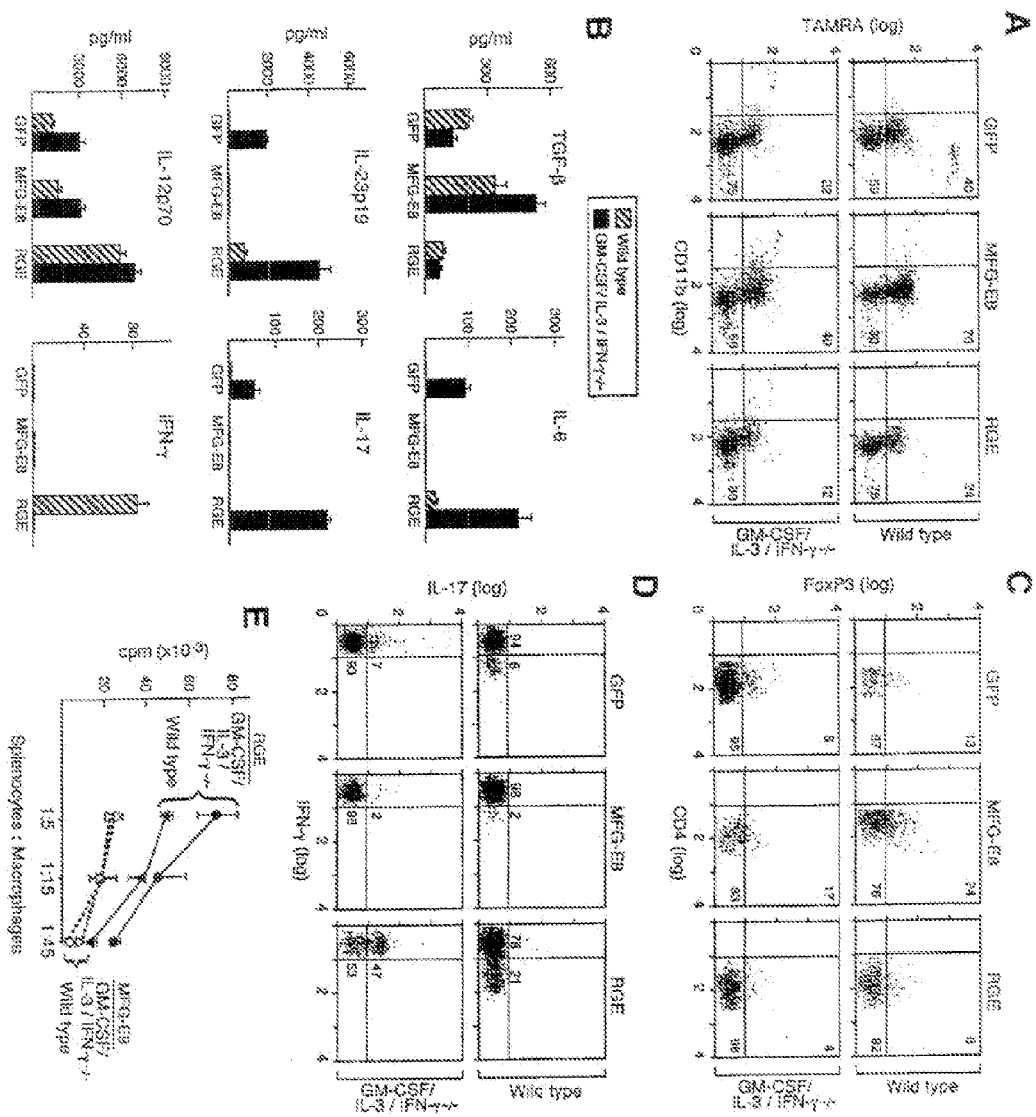
FIG. 5 depicts the results of an experiment demonstrating that MFG-E8 reconstitution restores CD4$^+$ T cell homeostasis in vivo. (A) Peritoneal macrophages recovered two months following transplantation with GFP, MFG-E8 or RGE transduced bone marrow (five mice per group) were assayed for phagocytosis of TAMRA labeled apoptotic thymocytes. (B) Cytokine levels measured by ELISA in sera obtained two months after transplant (n=4). (C) Splenocytes (n=4) were harvested two months after transplant and assayed for FoxP3 expression and (D) IL-17 and IFN-γ expression. Cytokine production for CD3$^+$CD4$^+$ gated cells is shown. (E) Peritoneal macrophages from transplanted mice were loaded with apoptotic cells and used to stimulate allogeneic Balb/c splenocytes. Proliferation was determined by $^3$H-thymidine uptake. Similar results were obtained with two independent transplant experiments.

To test further the role of MFG-E8 in GM-CSF dependent CD4+ T cell subset regulation, we performed bone marrow transplant experiments. Hematopoietic progenitors from wild type and GM-CSF/IL-3/IFN-γ deficient mice were transduced with retroviral vectors and infused into lethally irradiated 2-4 month old recipients. Mice were sacrificed two months after transplant, and GFP/MFG-E8 expression was documented in macrophages (not shown). MFG-E8 transduction resulted in the increased phagocytosis of apoptotic cells in both wild type and GM-CSF/IL-3/IFN-γ deficient macrophages, whereas the RGE mutant reduced corpse clearance in both strains (FIG. 5A). Enforced MFG-E8 expression resulted in increased levels of TGF-β and reduced levels of IL-6, IL-23p19, and IL-17 in the sera of wild type and GM-CSF/IL-3/IFN-γ deficient mice (FIG. 5B). No changes were evident in IL-12p70 concentrations. In contrast, the RGE mutant induced decreased levels of TGF-β, but increased levels of IL-6, IL-12p19, IL-17, and IL-12p70 in the sera of transplanted animals. The RGE mutant also triggered circulating levels of IFN-γ in wild type mice. This increased pro-inflammatory cytokine production might account for the low incidence of peri-transplant mortality observed only in animals that received RGE expressing bone marrow (not shown). Flow cytometry revealed that MFG-E8 transduction increased FoxP3+ Tregs in wild type and GM-CSF/IL-3/IFN-γ deficient splenocytes, whereas the RGE mutant decreased Tregs in wild type mice (FIG. 5C). MFG-E8 suppressed, but the RGE mutant increased Th17 cells in GM-CSF/IL-3/IFN-γ deficient mice, while the RGE mutant augmented Th1 cells in wild type recipients (FIG. 5D). MFG-E8 transduction also restored the immunosuppressive effects of apoptotic cells in GM-CSF/IL-3/IFN-γ deficient mice, as documented by the reduced allo-stimulatory activity (FIG. 5E). Taken together, these findings establish a requirement for MFG-E8 in the immunoregulatory activities of GM-CSF.

Example 7

Antigen Presenting Cell Maturation Involves MFG-E8 Down-Regulation

Figure 6:
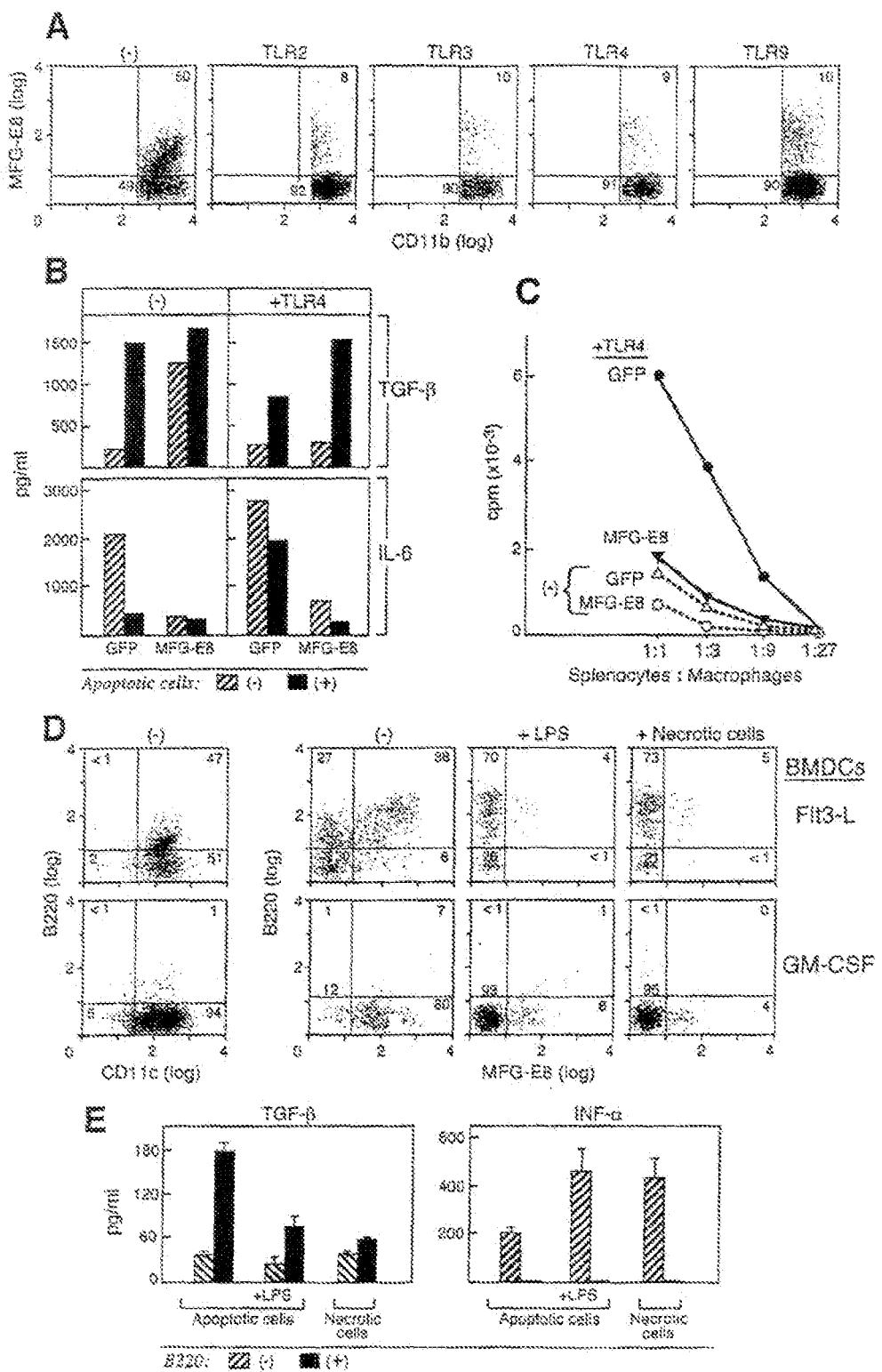
FIG. 6 depicts the results of an experiment demonstrating that MFG-E8 expression is down-regulated upon antigen presenting cell maturation. (A) Wild type peritoneal macrophages were exposed to apoptotic cells and peptidoglycan (TLR2), poly-IC (TLR3), LPS (TLR) or CpG (TLR9) and MFG-E8 expression determined. (B) Wild type peritoneal macrophages were engineered to express MFG-E8 or GFP and exposed to apoptotic cells with or without LPS. Culture supernatants were assayed for TGF-β and IL-6 production with ELISAs. (C) MFG-E8 or GFP expressing peritoneal macrophages were exposed to apoptotic cells with or without LPS and co-cultured with allogeneic Balb/c splenocytes. Proliferation was determined by $^3$H-thymidine uptake. (D) Flt3-L or GM-CSF generated bone marrow derived dendritic cells were assayed for B220 and MFG-E8 expression. LPS or freeze-thaw induced necrotic cells were added where indicated. (E) Flt3-L derived dendritic cells were sorted into B220$^+$ and B220$^-$ populations, exposed to apoptotic or necrotic cells, and assayed for TGF-β and IFN-α production by ELISA. Similar results were obtained in two independent experiments.

Since MFG-E8 plays a critical role in GM-CSF triggered tolerance, GM-CSF induced protective immunity might involve down-regulation of MFG-E8 function. Consistent with this idea, previous work showed that immature bone marrow derived dendritic cells generated with GM-CSF manifest high level MFG-E8 expression, whereas LPS induced maturation resulted in decreased MFG-E8 (Miyasaka et al., 2004). Here we extend these findings by showing that treatment of wild type peritoneal macrophages with multiple TLR agonists including peptidogycan (TLR2) poly-I-C (TLR3), LPS (TLR4), or CpG oligonucleotides (TLR9) suppressed MFG-E8 induction upon exposure to apoptotic cells (FIG. 6A). This inhibition proved functionally important, as enforced MFG-E8 expression (through retroviral transduction) antagonized the reduction in TGF-β and increase in IL-6 stimulated by LPS (FIG. 6B). MFG-E8 also suppressed the enhanced allo-stimulatory activity of apoptotic cell loaded macrophages treated with LPS (FIG. 6C).

Recent work established that B220−, but not B220+ Flt3-L generated bone marrow derived dendritic cells efficiently cross-present apoptotic cell antigens to stimulate CD8+ cytotoxic T cell responses (Janssen et al., 2006). We found that MFG-E8 expression was restricted to B220+ dendritic cells, whereas maturation with LPS or necrotic cells resulted in MFG-E8 down-regulation in these and GM-CSF derived dendritic cells (FIG. 6D). The sorted B220+, but not B220− Flt3-L generated dendritic cells secreted TGF-β upon exposure to apoptotic cells, though not necrotic cells. In contrast, the B220−, but not B220+ dendritic cells produced IFN-α in response to apoptotic cells, and this was increased with LPS, in accordance with the earlier report (Janssen et al., 2006). The B220−, but not B220+ dendritic cells also produced IFN-α in response to necrotic cells. Together, these findings support the idea that MFG-E8 contributes to the tolerogenic potential of specific dendritic cell subsets.

Example 8

MFG-E8 Regulates the Anti-Tumor Effects of GM-CSF Secreting Vaccines

Figure 7:
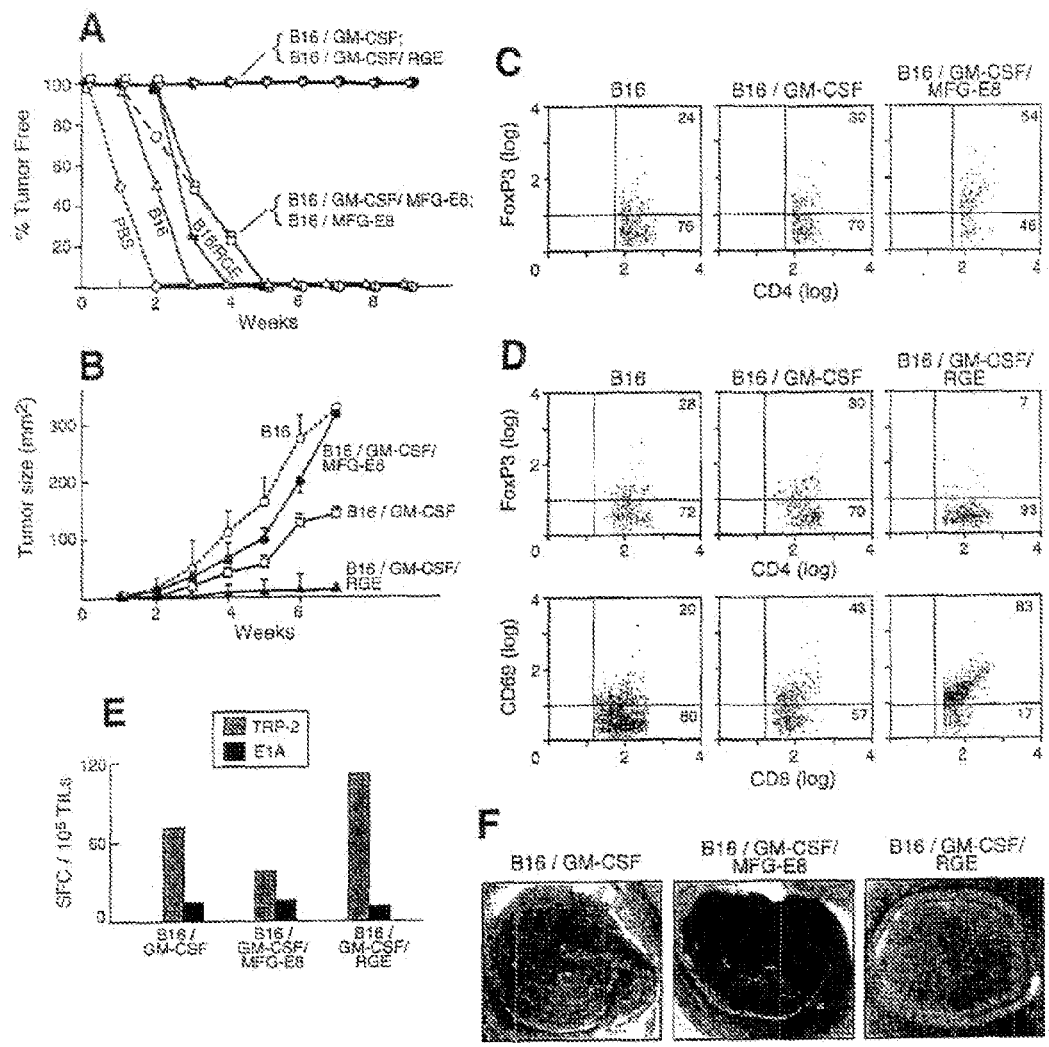
FIG. 7 depicts the results of an experiment demonstrating that MFG-E8 modulates the vaccination activity of irradiated, GM-CSF secreting B16 cells. (A) Wild type C57Bl/6 mice were vaccinated subcutaneously with 1×10$^6$ irradiated B16 cells as indicated and challenged on day seven with 1×10$^6$ live B16 cells (8 mice per group). (B) C57Bl/6 mice were injected with 1×10$^6$ live B16 cells and vaccines were administered as indicated on days 0, 7, and 14 (8 mice per group). (C) Tumor infiltrating lymphocytes were harvested from the B16 challenge sites of mice treated with the indicated vaccines and analyzed for FoxP3 expressing CD4$^+$ T cells. Results are representative of five experiments. (D) Tumor infiltrating lymphocytes were analyzed for FoxP3 expressing CD4$^+$ T cells and CD8$^+$ T cell activation. Similar results were obtained in two experiments. (E) Tumor infiltrating lymphocytes were analyzed for TRP-2 specific IFN-γ production with an ELISPOT. (F). Gross appearance of B16 challenge tumors in mice treated with the indicated vaccines (8 mice for B16-GM-CSF and B16-GM-CSF/MFG-E8 and 2 mice for B16-GM-CSF/RGE).

To examine directly the impact of MFG-E8 on GM-CSF stimulated protective responses, we utilized the B16 melanoma model (Dranoff et al., 1993). In this system, vaccination with irradiated, GM-CSF secreting tumor cells efficiently protects wild type syngeneic C57Bl/6 mice from subsequent challenge with live, wild type B16 cells, whereas vaccination with irradiated, parental B16 cells is ineffective (FIG. 7A). Immunization with B16 cells expressing the RGE mutant failed to protect against tumor challenge, indicating that blockade of phosphatidylserine was not sufficient for protective immunity in this system. Vaccines composed of B16 cells secreting MFG-E8 were similarly inactive. However, co-expression of MFG-E8 abrogated the protective immunity elicited with GM-CSF secreting tumor cells, whereas the RGE mutant did not.

To determine whether the RGE mutant might augment the anti-tumor effects of GM-CSF, we utilized a therapy model in which vaccination was begun on the same day as tumor challenge (FIG. 7B). Under these conditions, irradiated, GM-CSF secreting B16 cells evoke a modest delay in tumor growth, but all animals eventually succumb to progressive tumor. MFG-E8 co-expression also inhibited the impact of GM-CSF secreting tumor cells in this system. Nonetheless, the RGE mutant potentiated GM-CSF induced tumor destruction, as nearly all mice survived the wild type B16 challenge (7 of 8). When therapy was initiated three days after B16 injection, tumors grew initially, but the GM-CSF/RGE combination halted disease progression and induced regression in some animals (not shown). No toxicities of treatment were observed.

To analyze the mechanisms underlying these effects, we isolated tumor-infiltrating lymphocytes from wild type B16 challenge sites. The co-expression of MFG-E8 resulted in increased intra-tumoral Tregs (FIG. 7C), whereas the co-expression of the RGE mutant inhibited Treg recruitment compared to B16 cells secreting only GM-CSF (FIG. 7D). Moreover, the RGE mutant enhanced the activation of CD8$^+$ tumor infiltrating lymphocytes and increased the numbers of MHC class I restricted, tyrosinase related protein-2 (TRP-2) specific IFN-$\gamma$ secreting CD8$^+$ effector cells, whereas these were decreased with MFG-E8 (FIG. 7E).

The tumors harvested from treated mice showed striking differences in gross appearance. Melanomas arising in naïve mice (not shown) or in animals that received the GM-CSF/MFG-E8 vaccine were heavily pigmented, whereas those developing after the GM-CSF vaccine or the GM-CSF/RGE combination were not (FIG. 7F). Histopathologic examination confirmed the differences in melanin production (not shown). These findings suggest that MFG-E8-mediated modulation of immunity against melanocyte differentiation antigens, such as TRP-2, sculpts the phenotype of progressive tumors, consistent with the concept of immune editing (Dunn et al., 2004).

Figure 16:
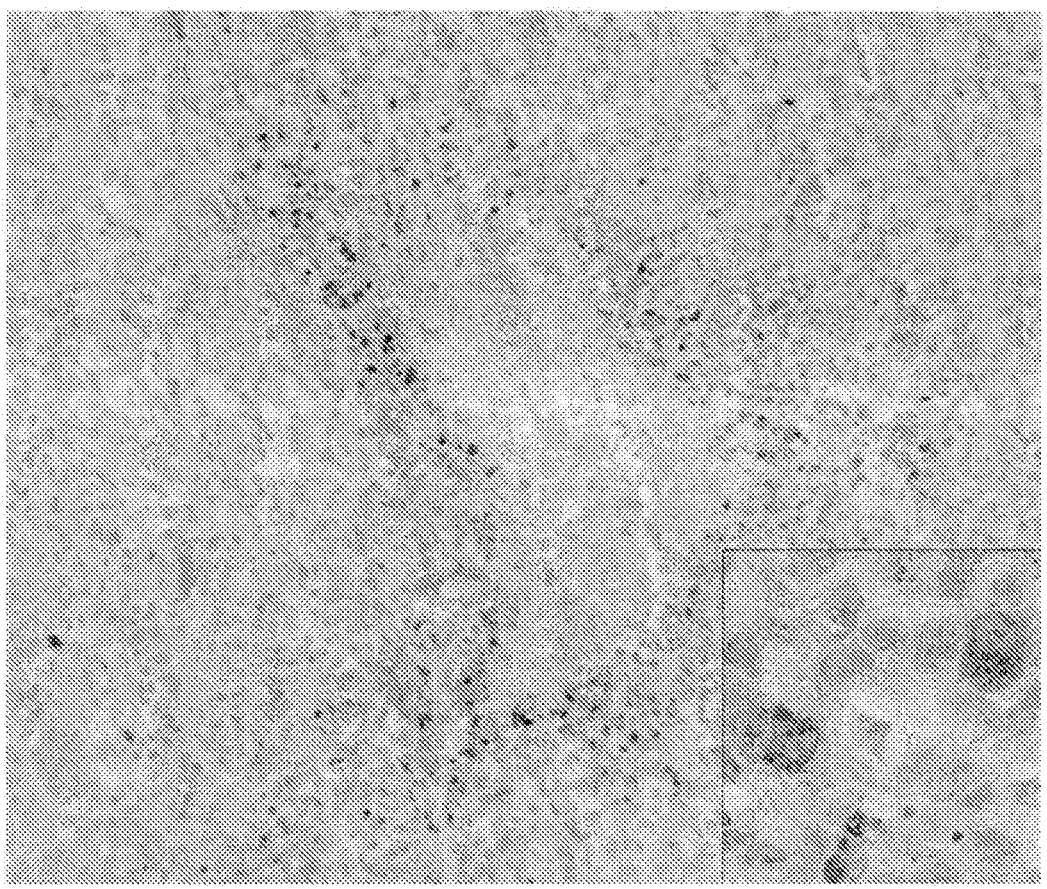
FIG. 16 depicts the results of a study showing that MFG-E8 is expressed in tumor-associated macrophages in human melanomas. Original magnification ×100, insert ×250.

Additional studies showed that tumor associated macrophages in diverse human malignancies display high levels of MFG-E8 by immunohistochemistry (FIG. 16 and data not shown).

Example 9

While MFG-E8 was detected by immunohistochemistry in germinal center macrophages and alveolar macrophages of wild type mice, consistent with previous reports, no staining was found in the spleens or lungs of GM-CSF deficient animals (FIG. 13) or in thymic macrophages from either strain. Splenic dendritic cells and Flt3-L derived bone marrow dendritic cells from GM-CSF deficient mice also showed reductions in MFG-E8 compared to wild type levels (described above), while similar decreases were observed with GM-CSF/IL-3 and GM-CSF/IL-3/IFN-$\gamma$ deficient antigen presenting cells. Modest reductions in $\alpha_v\beta_5$, Gas-6, and Mer were further detected (see above), suggesting that GM-CSF broadly regulates phosphatidylserine-based uptake of apoptotic cells.

To clarify the contribution of MFG-E8 deficiency, we used retroviral transduction to reconstitute MFG-E8 expression in peritoneal macrophages in vitro. A high titer virus encoding a previously described MFG-E8 mutant, in which the RGD sequence involved in integrin binding was modified to RGE, was also generated. This protein retains the capacity to bind phosphatidylserine on apoptotic cells, but cannot be internalized and thereby functions as a dominant negative inhibitor. Flow cytometry documented that transduced cytokine deficient macrophages achieved MFG-E8 levels comparable to wild type cells (not shown). MFG-E8 restoration increased the phagocytosis of apoptotic cells in GM-CSF deficient cells to wild type levels, whereas MFG-E8 over-expression in wild type cells further augmented corpse ingestion (above). Confocal microscopy demonstrated that MFG-E8 mediated engulfment of apoptotic cells, rather than simply surface binding to phagocytes (FIG. 15). MFG-E8 levels did not alter the uptake of necrotic cells (not shown). In contrast, the RGE mutant decreased apoptotic cell ingestion in wild type and cytokine deficient macrophages.

Example 10

A Model of the Dual Roles for GM-CSF in Tolerance and Protective Immunity

Figure 11:
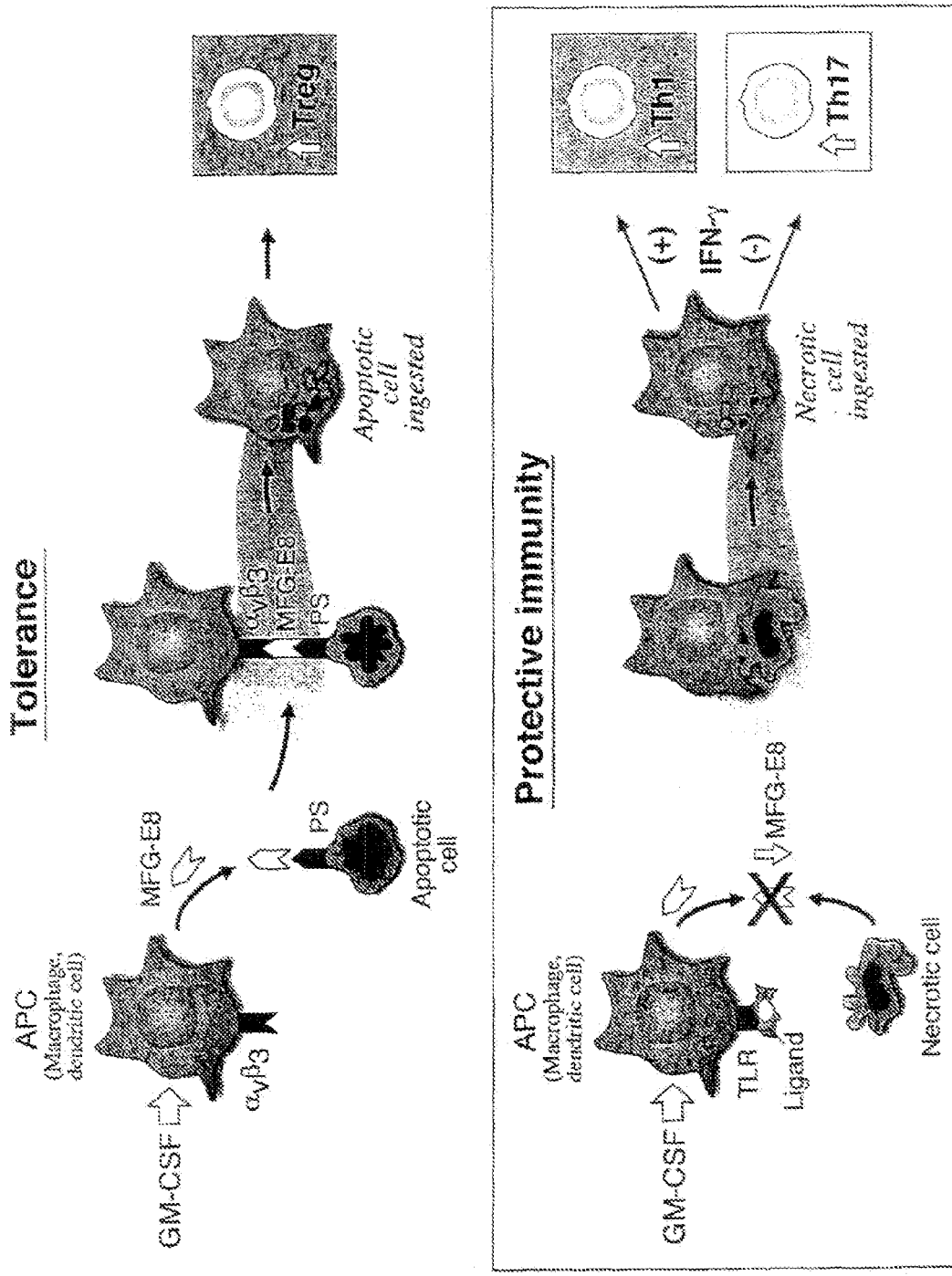
FIG. 11 depicts a model of the dual roles for GM-CSF in tolerance and protective immunity.

As shown in the examples above, we identified the phosphatidylserine binding protein MFG-E8 as a major determinant of GM-CSF function. Under steady-state conditions, GM-CSF induces MFG-E8 expression on antigen presenting cells, resulting in the efficient phagocytosis of apoptotic cells, the maintenance of Tregs in the periphery, and the suppression of autoreactive Th1 and Th17 cells. However, under conditions of stress, TLR agonists or necrotic cells down-regulate MFG-E8 expression whereby GM-CSF stimulates protective responses through an MFG-E8 independent mechanism. Together, these findings delineate a GM-CSF/MFG-E8 homeostatic circuit that regulates the balance of CD4$^+$ T cell subsets (FIG. 11).

In light of the immunoregulatory activities of MFG-E8, why does the provision of GM-CSF as cancer therapy increase anti-tumor responses? Our results indicate that diverse TLR agonists and necrotic cells down-regulate the expression of MFG-E8 on antigen presenting cells, and this suppression may be required for protective immunity. Indeed, enforced production of MFG-E8 antagonized the immunostimulatory impact of TLR agonists and irradiated, GM-CSF secreting tumor cell vaccines, whereas high levels of endogenous MFG-E8 were associated with tolerogenic dendritic cell subsets. While blockade of MFG-E8 function with the RGE mutant was insufficient to evoke protection in the B16 melanoma model, in conjunction with GM-CSF the strategy proved therapeutic against pre-existing lesions. This intensified activity suggests that irradiated, GM-CSF secreting tumor vaccines alone trigger only partial down-regulation of MFG-E8 in vivo. The enhanced immunity elicited by the combination treatment involved the inhibition of Tregs and the amplification of CD8+ cytotoxic T cells, resulting in a diversified host response capable of mediating regression of established tumors in the absence of toxicity. This mechanism of therapeutic synergy is distinct from that underlying CTLA-4 antibody blockade, which primarily targets effector cells, but also increases Tregs. Thus, the three approaches together might prove complementary and achieve even higher levels of protective tumor immunity.

Example 11

Nucleotide Sequence of the cDNA Encoding the Murine Wild-Type MFG-E8 Polypeptide (SEQ ID NO:1, NM_008594, GI:113865978)

This sequence was the wild-type sequence used for the retroviral mediated gene-transfer experiments.

```
    atgcaggtct cccgtgtgct ggccgcgctg tgcggcatgc tactctgcgc ctctggcctc
 61 ttcgccgcgt ctggtgactt ctgtgactcc agcctgtgcc tgaacggtgg cacctgcttg
121 acgggccaag acaatgacat ctactgcctc tgccctgaag gcttcacagg ccttgtgtgc
181 aatgagactg agagaggacc atgctcccca aacccttgct acaatgatgc caaatgtctg
241 gtgactttgg acacacagcg tggggacatc ttcaccgaat acatctgcca gtgccctgtg
301 ggctactcgg gcatccactg tgaaaccgag accaactact acaacctgga tggagaatac
361 atgttcacca cagccgtccc caatactgcc gtccccaccc cggccccac ccccgatctt
421 tccaacaacc tagcctcccg ttgttctaca cagctgggca tggaaggggg cgccattgct
481 gattcacaga tttccgcctc gtctgtgtat atgggtttca tgggcttgca gcgctgggc
541 ccggagctgg ctcgtctgta ccgcacaggg atcgtcaatg cctggacagc cagcaactat
601 gatagcaagc cctggatcca ggtgaacctt ctgcggaaga tgcgggtatc aggtgtgatg
661 acgcagggtg ccagccgtgc cgggagggcg gagtacctga agaccttcaa ggtggcttac
721 agcctgacg gacgcaagtt tgagttcatc caggatgaaa gcggtggaga caaggagttt
781 ttgggtaacc tggacaacaa cagcctgaag gttaacatgt tcaacccgac tctgaggca
841 cagtacataa agctgtaccc tgtttcgtgc caccgcggct gcaccctccg cttcgagctc
901 ctgggctgtg agttgcacgg atgttctgag cccctgggcc tgaagaataa cacaattcct
961 gacagccaga tgtcagcctc cagcagctac aagacatgga acctgcgtgc ttttggctgg
1021 tacccccact tgggaaggct ggataatcag ggcaagatca atgcctggac ggctcagagc
1081 aacagtgcca aggaatggct gcaggttgac ctgggcactc agaggcaagt gacaggaatc
1141 atcacccagg gggccgtga ctttggccac atccagtatg tggcgtccta caaggtagcc
1201 cacagtgatg atggtgtgca gtggactgta tatgaggagc aaggaagcag caaggtcttc
1261 cagggcaact tggacaacaa eteccacoag aagaacatct tcgagaaacc cttcatggct
1321 cgctacgtgc gtgtccttcc agtgtcctgg cataaccgca tcaccctgcg cctggagctg
1381 ctgggctgtt aa
```

Example 12

Amino Acid of the Wild-Type Murine MFG-E8 Polypeptide (SEQ ID NO:2, NM_008594, GI:113865978)

MQVSRVLAALCGMLLCASGLFAASGDFCDSSLCLNGGTGLTGQDNDIYGL
CPEGFTGLVCNETERGPCSPNPCYNDAKCLVTLDTQRGDIFTEYICQCPV
GYSGIHCETETNYYNLDGEYMFTTAVPNTAVPTPAPTPDLSNNLASRCST
QLGMEGGAIADSQISASSVYMGFMGLQRWGPELARLYRTGIVNAWTASNY
DSKPWIQVNLLRKMRVSGVMTQGASRAGRAEYLKTFKVAYSLDGRKFEFI
QDESGGDKEFLGNLDNNSLKVNMFNPTLEAQYIKLYPVSCHRGCTLRFEL
LGCELHGCSEPLGLKNNTIPDSQMSASSSYKTWNLRAFGWYPHLGRLDNQ
GKINAWTAQSNSAKEWLQVDLGTQRQVTGIITQGARDFGHIQYVASYKVA
HSDDGVQWTVYEEQGSSKVFQGNLDNNSHKKNIFEKPFMARYVRVLPVSW
HNRITLRLELLGC

Example 13

Nucleotide Sequence of the cDNA Encoding the Murine Mutant RGE MFG-ES Polypeptide (SEQ ID NO:3, NM_008594, GI:113865978)

This sequence was the RGE mutant sequence used for the retroviral mediated gene-transfer experiments. The location of the mutated residue (nucleotide 267) is shown in a bold-faced capital letter.

```
     atgcaggtct cccgtgtgct ggccgcgctg tgcggcatgc tactctgcgc ctctggcctc
 61  ttcgccgcgt ctggtgactt ctgtgactcc agcctgtgcc tgaacggtgg cacctgcttg
121  acgggccaag acaatgacat ctactgcctc tgccctgaag gcttcacagg ccttgtgtgc
181  aatgagactg agagaggacc atgctcccca aacccttgct acaatgatgc caaatgtctg
241  gtgactttgg acacacagcg tggggaAatc ttcaccgaat acatctgcca gtgccctgtg
301  ggctactcgg gcatccactg tgaaaccgag accaactact acaacctgga tggagaatac
361  atgttcacca cagccgtccc caatactgcc gtccccaccc cggccccac ccccgatctt
421  tccaacaacc tagcctcccg ttgttctaca cagctgggca tggaagggg cgccattgct
481  gattcacaga tttccgcctc gtctgtgtat atgggtttca tgggcttgca gcgctggggc
541  ccggagctgg ctcgtctgta ccgcacaggg atcgtcaatg cctggacagc cagcaactat
601  gatagcaagc cctggatcca ggtgaacctt ctgcggaaga tgcgggtatc aggtgtgatg
661  acgcagggtg ccagccgtgc cgggagggcg gagtacctga agaccttcaa ggtggcttac
721  agcctcgacg gacgcaagtt tgagttcatc caggatgaaa gcggtggaga caaggagttt
781  ttgggtaacc tggacaacaa cagcctgaag gttaacatgt tcaacccgac tctggaggca
841  cagtacataa agctgtaccc tgtttcgtgc caccgcggct gcaccctccg cttcgagctc
901  ctgggctgtg agttgcacgg atgttctgag ccctgggcc tgaagaataa cacaattcct
961  gacagccaga tgtcagcctc cagcagctac aagacatgga acctgcgtgc ttttggctgg
1021 tacccccact gggaaggct ggataatcag ggcaagatca tgcctggac ggctcagagc
1081 aacagtgcca aggaatggct gcaggttgac ctgggcactc agaggcaagt gacaggaatc
1141 atcacccagg gggccgtga ctttggccac atccagtatg tggcgtccta caaggtagcc
1201 cacagtgatg atggtgtgca gtggactgta tatgaggagc aaggaagcag caaggtcttc
1261 cagggcaact tggacaacaa ctcccacaag aagaacatct tcgagaaacc cttcatggct
1321 cgctacgtgc gtgtccttcc agtgtcctgg cataaccgca tcaccctgcg cctggagctg
1381 ctgggctgtt aa
```

Example 14

Amino Acid of the Mutant Murine MFG-E8 Polypeptide (SEQ ID NO:4, NM_008594, GI:113865978)

The location of the mutated residue (amino acid 89) is shown in a bold-faced lower case letter.

```
MQVSRVLAALCGMLLCASGLFAASGDFCDSSLCLNGGTCLTGQDNDIYCL
CPEGFTGLVCNETERGPCSPNPCYNDAKCLVTLDTQRGeIFTEYICQCPV
GYSGIHCETETNYYNLDGEYMFITAVPNTAVPTPAPTPDLSNNLASRCST
QLGMEGGAIADSQISASSVYMGFMGLQRWGPELARLYRTGIVNAWTASNY
DSKPWIQVNLLRKMRVSGVMTQGASRAGRAEYLKTFKVAYSLDGRKFEFI
QDESGGDKEFLGNLDNNSLKVNMFNPTLEAQYIKLYPVSCHRGCTLRFEL
LGCELHGCSEPLGLKNNTIPDSQMSASSSYKTWNLRAFGWYPHLGRLDNQ
GKINAWTAQSNSAKEWLQVDLGTQRQVTGIITQGARDFGHIQYVASYKVA
HSDDGVQWTVYEEQGSSKVFQGNLDNNSHKKNIFEKPFMARYVRVLPVSW
HNRITLRLELLGC"
```

Example 15

Nucleotide Sequence of the cDNA Encoding the Human Wild-Type MFG-E8 Polypeptide (SEQ ID NO:5, NM_005928, GI:5174556)

```
   1 atgccgcgcc cccgcctgct ggccgcgctg tgcggcgcgc tgctctgcgc ccccagcctc
  61 ctcgtcgccc tggatatctg ttccaaaaac ccctgccaca acggtggttt atgcgaggag
 121 atttcccaag aagtgcgagg agatgtcttc ccctcgtaca cctgcacgtg ccttaagggc
 181 tacgcgggca accactgtga gacgaaatgt gtcgagccac tgggcatgga gaatgggaac
 241 attgccaact cacagatcgc cgcctcatct gtgcgtgtga ccttcttggg tttgcagcat
 301 tgggtcccgg agctggcccg cctgaaccgc gcaggcatgg tcaatgcctg gacacccagc
 361 agcaatgacg ataacccctg gatccaggtg aacctgctgc ggaggatgtg ggtaacaggt
 421 gtggtgacgc agggtgccag ccgcttggcc agtcatgagt acctgaaggc cttcaaggtg
 481 gcctacagcc ttaatggaca cgaattcgat ttcatccatg atgttaataa aaaacacaag
 541 gagtttgtgg gtaactggaa caaaaacgcg gtgcatgtca acctgtttga ccccctgtg
 601 gaggctcagt acgtgagatt gtaccccacg agctgccaca cggcctgcac tctgcgcttt
 661 gagctactgg gctgtgagct gaacggatgc gccaatcccc tgggcctgaa gaataacagc
 721 atccctgaca agcagatcac ggcctccagc agctacaaga cctggggctt gcatctcttc
 781 agctggaacc cctcctatgc acggctggac aagcagggca acttcaacgc ctgggttgcg
 841 gggagctacg gtaacgatca gtggctgcag gtggacctgg gctcctcgaa ggaggtgaca
 901 ggcatcatca cccagggggc ccgtaacttt ggctctgtcc agtttgtggc atcctacaag
 961 gttgcctaca gtaatgacag tgcgaactgg actgagtacc aggacccag gactggcagc
1021 agtaagatct cccctggcaa ctgggacaac cactcccaca gaagaactt gtttgagacg
1081 cccatcctgg ctcgctatgt gcgcatcctg cctgtagcct ggcacaaccg catcgccctg
1141 cgcctggagc tgctgggctg ttag
```

Example 16

Amino Acid Sequence of the Wild-Type Human MFG-E8 Polypeptide (SEQ ID NO:6, NM_005928, GI:5174556)

MPRPRLLAALCGALLCAPSLLVALDICSKNPCHNGGLCEEISQEVRGDVF

PSYTCTCLKGYAGNHCETKCVEPLGMENGNLANSQIAASSVRVTFLGLQH

WVPELARLNRAGMVNAWTPSSNDDNPWIQVNLLRRMWVTGVVTQGASRLA

SHEYLKAFKVAYSLNGHEFDFIHDVNKKHKEFVGNWNKNAVHVNLFETPV

EAQYVRLYPTSCHTACTLRFELLGCELNGCANPLGLKINNSIPDKQITAS

SSYKTWGLHLFSWNPSYARLDKQGNFNAWVAGSYGNDQWLQVDLGSSKEV

TGIITQGARNFGSVQFVASYKVAYSNDSANWTEYQDPRTGSSKIFPGNWD

NHSHKKNLFETPILARYVRILPVAWHNRIALRLELLGC

Example 17

Nucleotide Sequence of the cDNA Encoding the Human RGE Mutant MFG-ES Polypeptide (SEQ ID NO:7, NM_OO5918, GI:5174556)

The location of the mutated residue (nucleotide 144) is shown in a bold-faced capital letter.

```
  1 atgccgcgcc cccgcctgct ggccgcgctg tgcggcgcgc tgctctgcgc ccccagcctc
 61 ctcgtcgccc tggatatctg ttccaaaaac ccctgccaca acggtggttt atgcgaggag
121 atttcccaag aagtgcgagg agaAgtcttc ccctcgtaca cctgcacgtg ccttaagggc
181 tacgcgggca accactgtga gacgaaatgt gtcgagccac tgggcatgga gaatgggaac
241 attgccaact cacagatcgc cgcctcatct gtgcgtgtga ccttcttggg tttgcagcat
301 tgggtcccgg agctggcccg cctgaaccgc gcaggcatgg tcaatgcctg gacaccoage
```

```
361 agcaatgacg ataaccoctg gatccaggtg aacctgctgc ggaggatgtg ggtaacaggt 421 gtggtgacgc agggtgccag ccgcttggcc agtcatgagt acctgaaggc cttcaaggtg 481 gcctacagcc ttaatggaca cgaattcgat ttcatccatg atgttaataa aaaacacaag 541 gagtttgtgg gtaactggaa caaaaacgcg gtgcatgtca acctgtttga gacccctgtg 601 gaggctcagt acgtgagatt gtaccccacg agctgccaca cggcctgcac tctgcgcttt 661 gagctactgg gctgtgagct gaacggatgc gccaatcccc tgggcctgaa gaataacagc 721 atccctgaca agcagatcac ggcctccagc agctacaaga cctggggctt gcatctcttc 781 agctggaacc cctcctatgc acggctggac aagcagggca acttcaacgc ctgggttgcg 841 gggagctacg gtaacgatca gtggctgcag gtggacctgg gctcctcgaa ggaggtgaca 901 ggcatcatca cccaggggcc ccgtaacttt ggctctgtcc agtttgtggc atcctacaag 961 gttgcctaca gtaatgacag tgcgaactgg actgagtacc aggacccag gactggcagc 1021 agtaagatct tccctggcaa ctgggacaac cactcccaca agaagaactt gtttgagacg 1081 cccatcctgg ctcgctatgt gcgcatcctg cctgtagcct ggcacaaccg catcgccctg 1141 cgcctggagc tgctgggctg ttag
```

Example 18

Amino Acid Sequence of the Mutant RGE Human MFG-E8 Polypeptide (SEQ ID NO:8, NM_005928, GI:5174556)

The location of the mutated residue (amino acid 48) is shown in a bold-faced lower case letter.

MPRPRLLAALCGALLGAPSLLVALDICSKNPCHNGGLCEEISQEVRGeVF
PSYTCTCLKGYAQNHCETKCVEPLGMENGNIANSQIAASSVRVTFLGLQH
WVPELARLNRAGMVNAWTPSSNDDNPWIQVNLLRRMWVTGVVTQGASRLA
SHEYLKAFKVAYSLNGHEFDFIHDVNKKHKEFVGNWNKNAVHVNLFETPV
EAQYVRLYPTSCHTACTLRFELLGCELNGCANPLGLKNNSIPDKQITASS
SYKTWGLHLFSWNPSYARLDKQGNFNAWVAGSYGNDQWLQVDLGSSKEVT
GIITQGARNFGSVQFVASYKVAYSNDSANWTEYQDPRTGSSKIFPGNWDN
HSHKKNLFETPILARYVRILPVAWHNRIALRLELLGC

A number of embodiments of the invention have been described. Nevertheless, it will be understood that various modifications may be made without departing from the spirit and scope of the invention. Accordingly, other embodiments are within the scope of the following claims.

---

The invention claimed is:

1. A method of treating a cancer or cancer symptom in a subject, the method comprising administering to the subject GM-CSF expressing autologous tumor cells and an MFG-E8 inhibitor selected from the group consisting of an anti-MFG-E8 antibody, an anti-phosphatidylserine antibody, and an MFG-E8 polypeptide that lacks the ability to bind integrins, wherein the autologous tumor cells and the MFG-E8 inhibitor are administered in amounts that, in combination, are effective for eliciting an anti-tumor immune response and, wherein, the anti-tumor immune response comprises the activation of CD8+ tumor infiltrating lymphocytes.

2. The method of claim 1, wherein the method comprises administering a single composition comprising the autologous tumor cells and the selected MFG-E8 inhibitor.

3. The method of claim 1, wherein the method comprises administering a first composition comprising the autologous tumor cells and administering a second composition comprising the selected MFG-E8 inhibitor.

4. The method of claim 1, wherein the autologous tumor cells are proliferation incompetent.

5. The method of claim 1, further comprising administering GM-CSF to the subject.

6. The method of claim 1, further comprising administering an anti-CTLA-4 antibody to the subject.

7. The method of claim 1 wherein the cancer is selected from the group consisting of melanoma, breast cancer, lung cancer, kidney cancer, ovarian cancer, colon cancer and leukemia.

8. The method of claim 1, wherein the autologous tumor cells are administered by injection, infusion or inhalation.

9. The method of claim 1, wherein the MFG-E8 inhibitor is an anti-MFG-E8 antibody.

10. The method of claim 1, wherein the MFG-E8 inhibitor is an MFG-E8 polypeptide that lacks the ability to bind integrins.

11. The method of claim 1, wherein the MFG-E8 inhibitor is an anti-phosphatidylserine antibody.

12. The method of claim 1, wherein the selected MFG-E8 inhibitor is administered by injection, infusion or inhalation.

13. The method of claim 1, wherein the autologous tumor cells are apoptotic.

* * * * *

UNITED STATES PATENT AND TRADEMARK OFFICE
CERTIFICATE OF CORRECTION

PATENT NO. : 9,492,518 B2  
APPLICATION NO. : 12/444047  
DATED : November 15, 2016  
INVENTOR(S) : Dranoff et al.

Page 1 of 1

It is certified that error appears in the above-identified patent and that said Letters Patent is hereby corrected as shown below:

Column 1, Lines 8-14, should read:
--GOVERNMENT SUPPORT CLAUSE
This invention was made with government support under grant number CA074886 awarded by The National Institute of Health. The government has certain rights in the invention.--

Signed and Sealed this
Tenth Day of April, 2018

Andrei Iancu
*Director of the United States Patent and Trademark Office*